(12) United States Patent
Seligmann et al.

(10) Patent No.: US 8,741,564 B2
(45) Date of Patent: Jun. 3, 2014

(54) QUANTITATIVE NUCLEASE PROTECTION ASSAY (QNPA) AND SEQUENCING (QNPS) IMPROVEMENTS

(75) Inventors: Bruce Seligmann, Tucson, AZ (US); Debrah Thompson, Tucson, AZ (US); Tom Vasicek, Minneapolis, MN (US); Debra A. Gordon, Tucson, AZ (US)

(73) Assignee: HTG Molecular Diagnostics, Inc., Tucson, AZ (US)

( * ) Notice: Subject to any disclaimer, the term of this patent is extended or adjusted under 35 U.S.C. 154(b) by 0 days.

(21) Appl. No.: 14/115,032

(22) PCT Filed: Apr. 26, 2012

(86) PCT No.: PCT/US2012/035260
§ 371 (c)(1),
(2), (4) Date: Oct. 31, 2013

(87) PCT Pub. No.: WO2012/151111
PCT Pub. Date: Nov. 8, 2012

(65) Prior Publication Data
US 2014/0087954 A1  Mar. 27, 2014

Related U.S. Application Data

(60) Provisional application No. 61/482,486, filed on May 4, 2011, provisional application No. 61/537,492, filed on Sep. 21, 2011, provisional application No. 61/576,143, filed on Dec. 15, 2011.

(51) Int. Cl.
*C12Q 1/68* (2006.01)
*C12P 19/34* (2006.01)

(52) U.S. Cl.
USPC ..................... 435/6.1; 435/6.12; 435/91.2

(58) Field of Classification Search
USPC ........................................ 435/6.1, 6.12, 91.2
See application file for complete search history.

(56) References Cited

U.S. PATENT DOCUMENTS

| | | | |
|---|---|---|---|
| 5,861,250 A | 1/1999 | Stanley et al. | |
| 6,090,589 A | 7/2000 | Dimond et al. | |
| 6,232,066 B1 | 5/2001 | Felder et al. | |
| 6,238,869 B1 | 5/2001 | Kris et al. | |
| 6,900,013 B1 | 5/2005 | Wang et al. | |
| 7,033,753 B1 | 4/2006 | Kool | |
| 2004/0086892 A1 | 5/2004 | Crothers et al. | |
| 2005/0100900 A1 | 5/2005 | Kawashima et al. | |
| 2006/0177841 A1 | 8/2006 | Wangh et al. | |
| 2007/0117121 A1 | 5/2007 | Hutchison et al. | |
| 2007/0172839 A1 | 7/2007 | Smith et al. | |
| 2007/0224174 A1 | 9/2007 | Kang et al. | |
| 2007/0224613 A1 | 9/2007 | Strathmann | |
| 2008/0268451 A1 | 10/2008 | Seligmann et al. | |
| 2009/0075276 A1 | 3/2009 | Lee et al. | |
| 2009/0137407 A1* | 5/2009 | Church et al. | 506/7 |
| 2010/0151470 A1 | 6/2010 | Zamore et al. | |
| 2011/0104693 A1 | 5/2011 | Seligmann | |
| 2012/0003657 A1 | 1/2012 | Myllykangas et al. | |
| 2012/0028814 A1 | 2/2012 | Toloue et al. | |

FOREIGN PATENT DOCUMENTS

| | | |
|---|---|---|
| GB | 2 285 445 A | 7/1995 |
| WO | WO 97/40189 A1 | 10/1997 |
| WO | WO 2008/121927 A1 | 10/2008 |
| WO | WO 2009/109753 A2 | 9/2009 |
| WO | WO 2011/032040 A1 | 3/2011 |
| WO | WO 2011/053987 A1 | 5/2011 |
| WO | WO 2012/149171 A1 | 11/2012 |

OTHER PUBLICATIONS

Agilent Technologies, "SureSelect RNA Target Enrichment for Illumina Paired-End Multiplexed Sequencing," Manual Part No. G7580-90010, Version 2.2.1, Agilent Technologies, Inc., Santa Clara, CA, Feb. 2012. 76 pages.
Agilent Technologies, "SureSelect$^{XT}$ Target Enrichment for Illumina Paired-End Sequencing Library, Illumina HiSeq and MiSeq Multiplexed Sequencing Platforms," Manual Part No. G7530-90000, Version 1.4.1, Agilent Technologies, Inc., Santa Clara, CA, Sep. 2012. 72 pages.
Bainér et al., "Parallel Gene Analysis With Allele-Specific Padlock Probes and Tag Microarrays," *Nucleic Acids Res. 31*:e103(1-7), 2003.
Coppee et al., "Do DNA Microarrays Have Their Future Behind Them?," *Microbes Infect. 10*:1067-1071, 2008.
Demidov et al., "Sequence Selective double Strand DNA Cleavage by peptide Nucleic Acid (PNA) Targeting Using Nuclease S1," *Nucleic Acids Res. 21*:2103- 2107, 1993.
Frank, D.N., "BARCRAWL and BARTAB: Software Tools for the Design and Implementation of Barcoded Primers for Highly Multiplexed DNA Sequencing," *BMC Bioinformatics 10*:362, 2009.
Illumina, Inc., "Multiplexed Sequencing with the Illumina Genome Analyzer System," Illumina Sequencing, No. 770-2008-011, pp. 1-4, 2008.
Kitazawa et al., "In situ Hybridization with Polymerase Chain Reaction-Derived Single-Stranded DNA Probe and S1 Nuclease," *Histochem. Cell Biol. 111*:7-12, 1999.
Li et al., "Multiplex Padlock Targeted Sequencing Reveals Human Hypermutable CpG Variations," *Genome Res. 19*:1606-1615, 2009.
Lutay et al., "The Nonenzyatic Template-Directed Ligation of Oligonucleotides. Biosciences," *Biogeociences 3*:243-249, 2006.
Mardis, E.R., "The Impact of Next-Generation Sequencing Technology on Genetics," *Trends Genet. 24*:133-141, 2007.

(Continued)

*Primary Examiner* — Ardin Marschel
(74) *Attorney, Agent, or Firm* — Klarquist Sparkman, LLP

(57) ABSTRACT

The present disclosure provides an improvement to quantitative Nuclease Protection Assay (qNPA) and quantitative Nuclease Protection Sequencing (qNPS) methods. The disclosed methods use nuclease protection probes (NPPs) that include 5'-end and/or 3-end flanking sequences, which provide a universal hybridization and/or amplification sequence. The disclosed methods can be used to sequence or detect target nucleic acid molecules, such as those present in fixed or insoluble samples.

20 Claims, 16 Drawing Sheets

(56) References Cited

OTHER PUBLICATIONS

Martel et al., "36. Multiplexed Molecular Profiling Transcription Assay in ArrayPlates™ for High-Throughput Measurement of Gene Expression," in *Gene Cloning and Expression Technologies*, Weiner and Lu (eds.), pp. 549-564, Eaton Publishing, Westborough, MA, 2002.

Martel et al., "Multiplexed Screening Assay for mRNA Combining Nuclease Protection with Luminescent Array Detection," Assay and Drug Development Technologies, Mary Ann Liebert, Inc., Publishers, U.S., vol. 1, No. 1-1, Nov. 1, 2002, pp. 61-71.

Morris et al., "Combination of a New Generation of PNAs with a Peptide-Based Carrier Enables Efficient Targeting of Cell Cycle Progression," *Gene Ther.* 11:757-764, 2004.

Nuovo et al., "Importance of Different Variables for Enhancing In Situ Detection of PCR-Amplified DNA," *Genome Res.* 2:305-312, 1993.

Pechhold et al., "Transcriptional Analysis of Intracytoplasmically Stained, FACS—Purified Cells by High-Throughput, Quantitative Nuclease Protection," *Nature Biotechnol.* Advance Online Publication, pp. 1-6, 2009.

Pellestor et al., "The Use of Peptide Nucleic Acids for In Situ Identification of Human Chromosomes," *J. Histochem. Cytochem.* 53:395-400, 2005.

Pino et al., "Nonenzymatic RNA Litgation in Water," *J. Biol. Chem.* 283:36494-36503, 2008.

Prins et al., "Optimised Padlock Probe Ligation and Microarray Detection of Multiple (Non-Authorised) GMOs in Single Reaction," *BMC Genomics* 9:584(112), 2008.

Rimsza et al., "Gene Expression Predicts Overall Survival in Paraffin Embedded Tissues of Diffuse Large B Cell Lymphoma Treated with R-CHOP," *Blood* 112:3425-3433, 2008.

Roberts et al., "Quantitative Nuclease Protection Assay in Paraffin-Embedded Tissue Replicates Prognostic Microarray Gene Expression in Diffuse Large-B-Cell Lymphoma," *Lab. Invest.* 87:979-997, 2007.

Seligmann et al., Quantitative Measurement of Gene Expression from Formalin-Fixed Tissue Providing Identical Results as Fresh Tissue: Biomarker Validation using Clinical Samples. *J. Biomolecular Tech.* 18:1&13, Poster P35-M, 2007. Association of Biomolecular Resource Facilities (ABRF), Abstract.

Shabarova et al., "Chemical Ligation of DNA: the First Non-Enzymatic Assembly of a Biologically Active Gene," *Nucleic Acids Res.* 19:4247-4251, 1991.

Teng et al., "Perspectives of DNA Microarray and Next-Generation DNA Sequencing Technologies," *Sci. China Ser. C-Life Sci.* 52:7-16, 2009.

Thompson et al., "Targeted Gene Expression Screening from FFPE: NPSeq™," Poster #4146, presented at AACR Annual Meeting, Washington, DC, Apr. 2013.

Wang et al., "RNA-Seq: A Revolutionary Tool for Transcriptomics," *Nat. Rev. Genet.* 10:57-63, 2009.

Zhang et al., "Digital RNA Allelotyping Reveals Tissue-Specific and Allele-Specific Gene Expression in Human," *Nature Methods* 6:613-618, 2009.

Banér et al., "Signal Amplification of Padlock Probes by Rolling Circle Replication," *Nucleic Acid Res.* 26:5073-5078, 1998.

\* cited by examiner

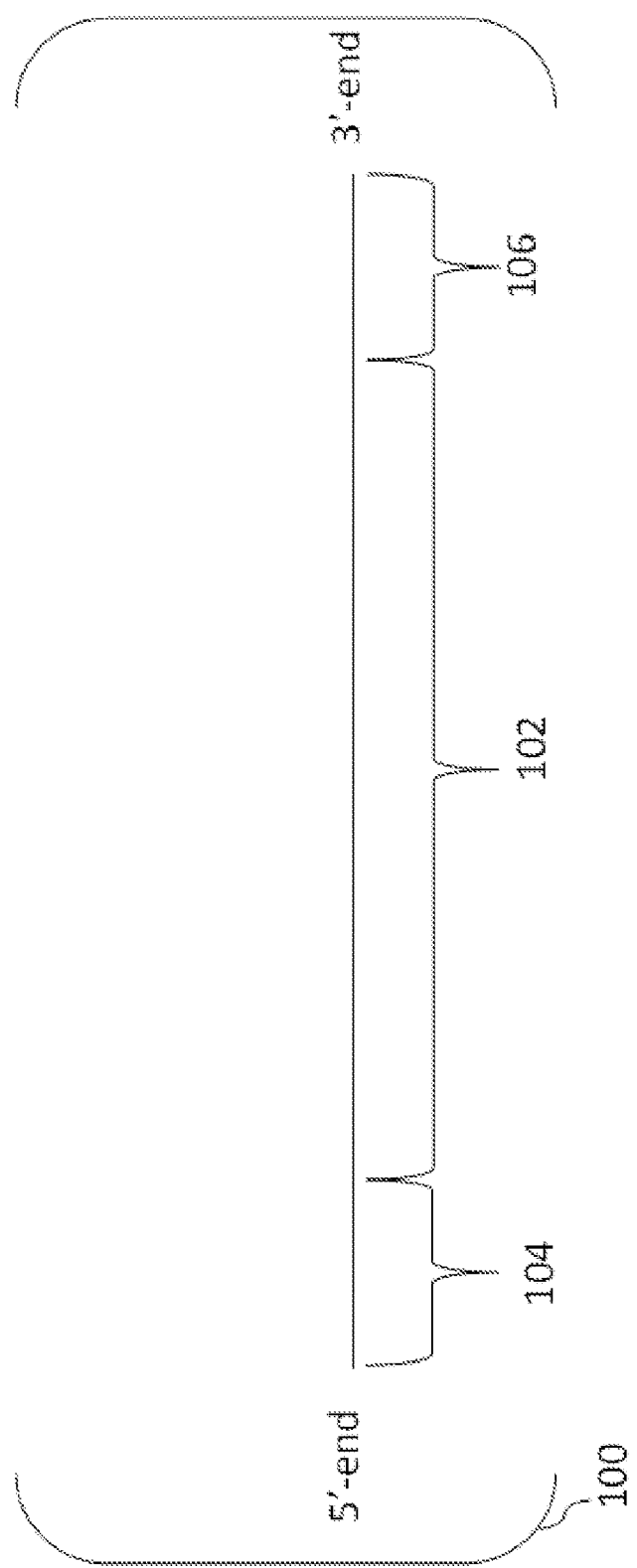

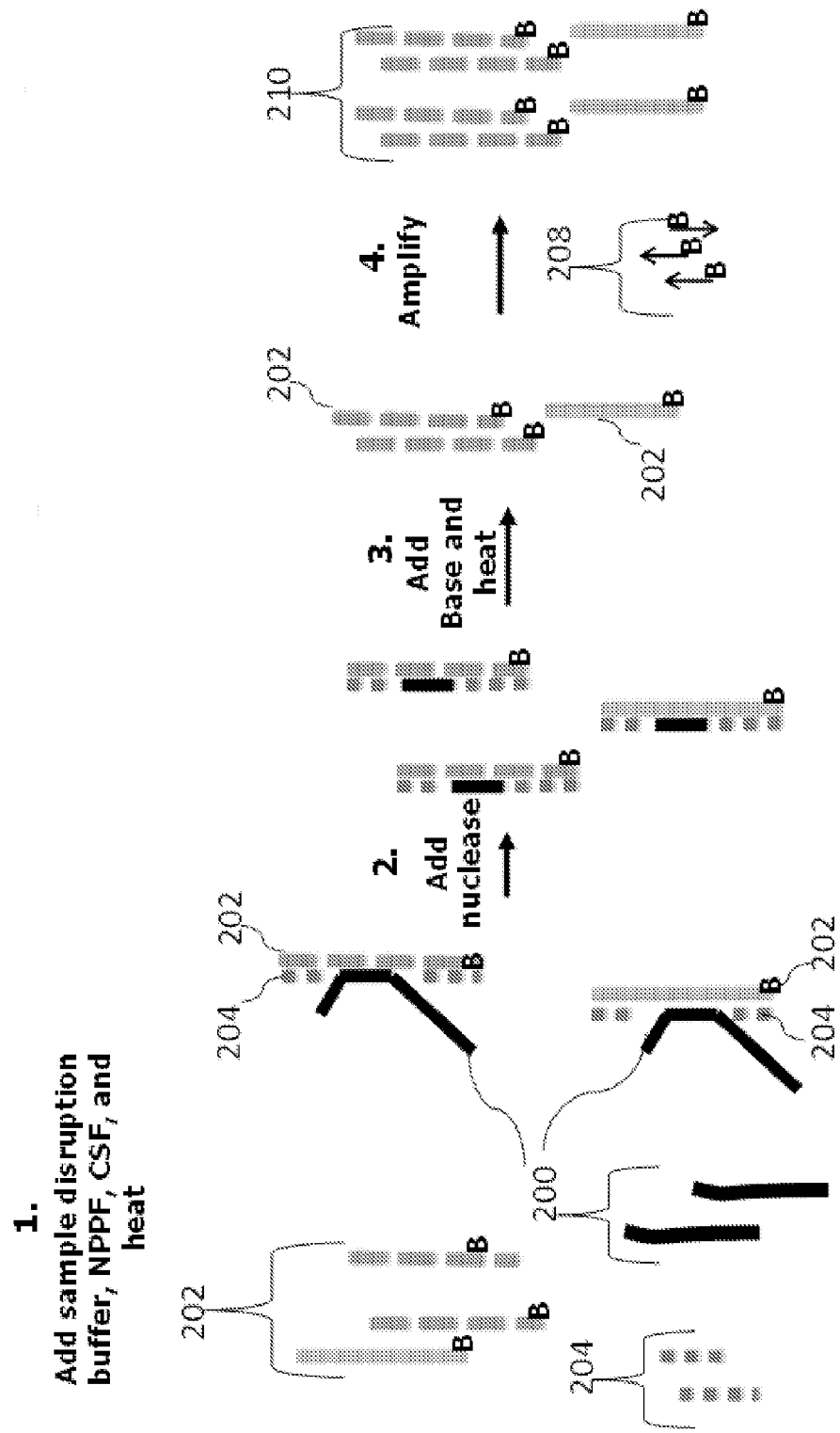

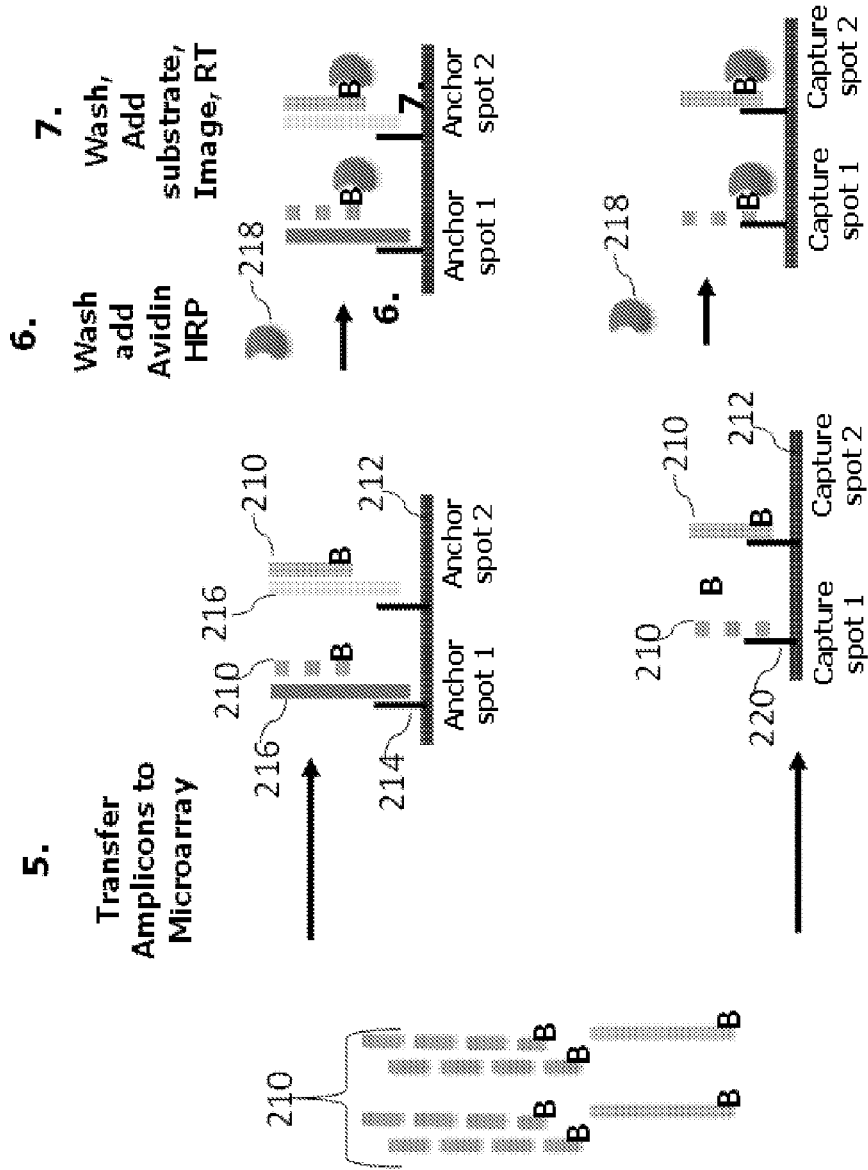

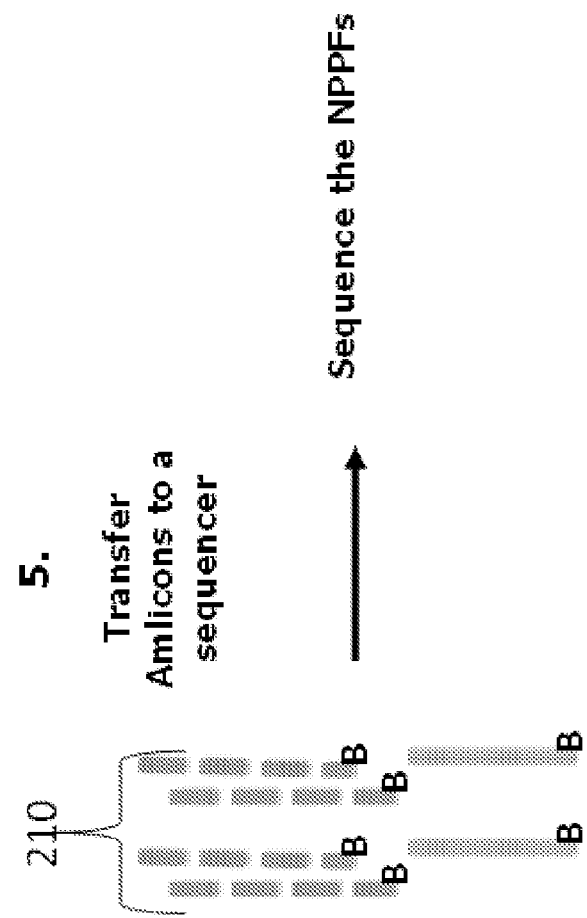

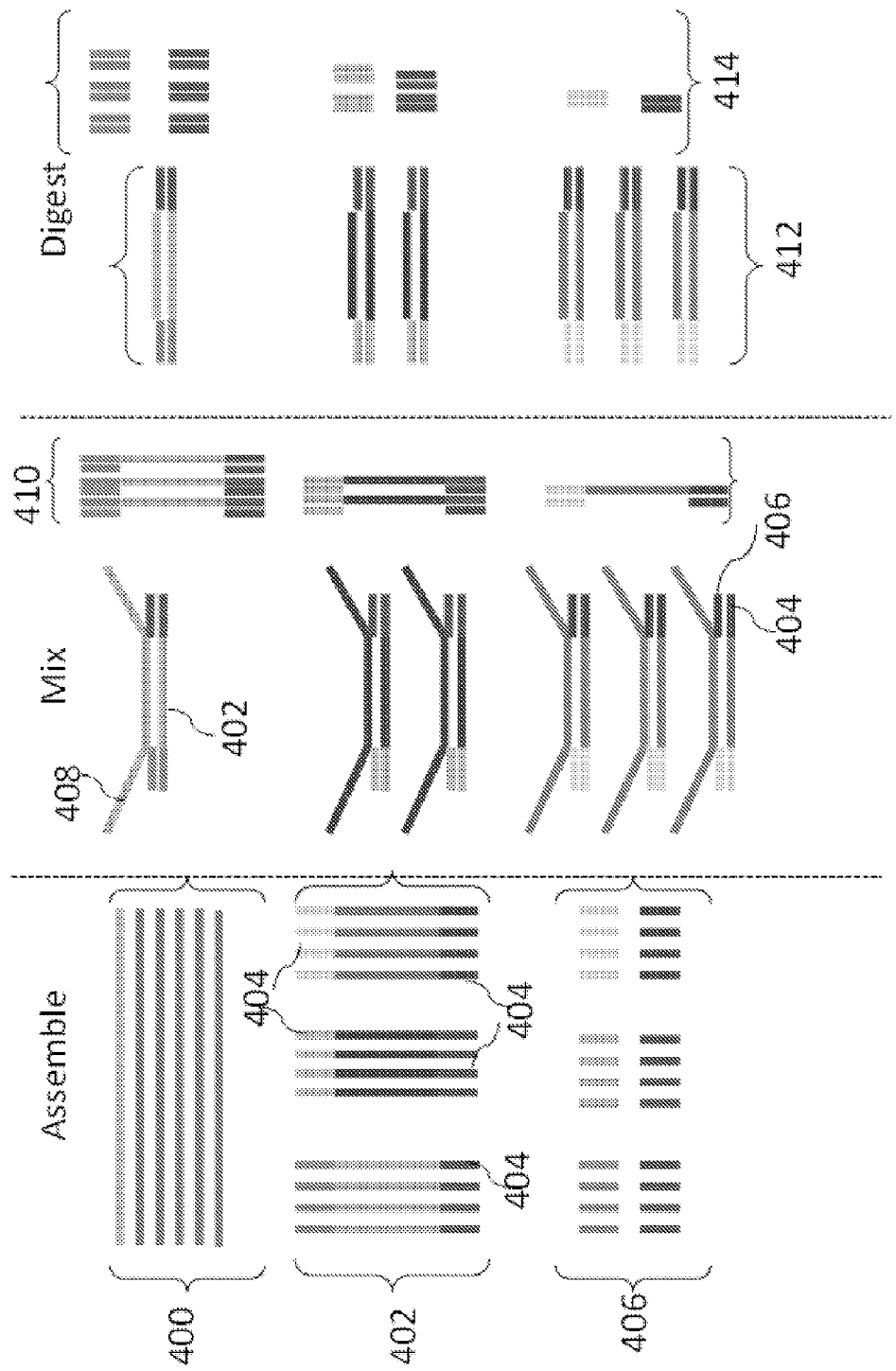

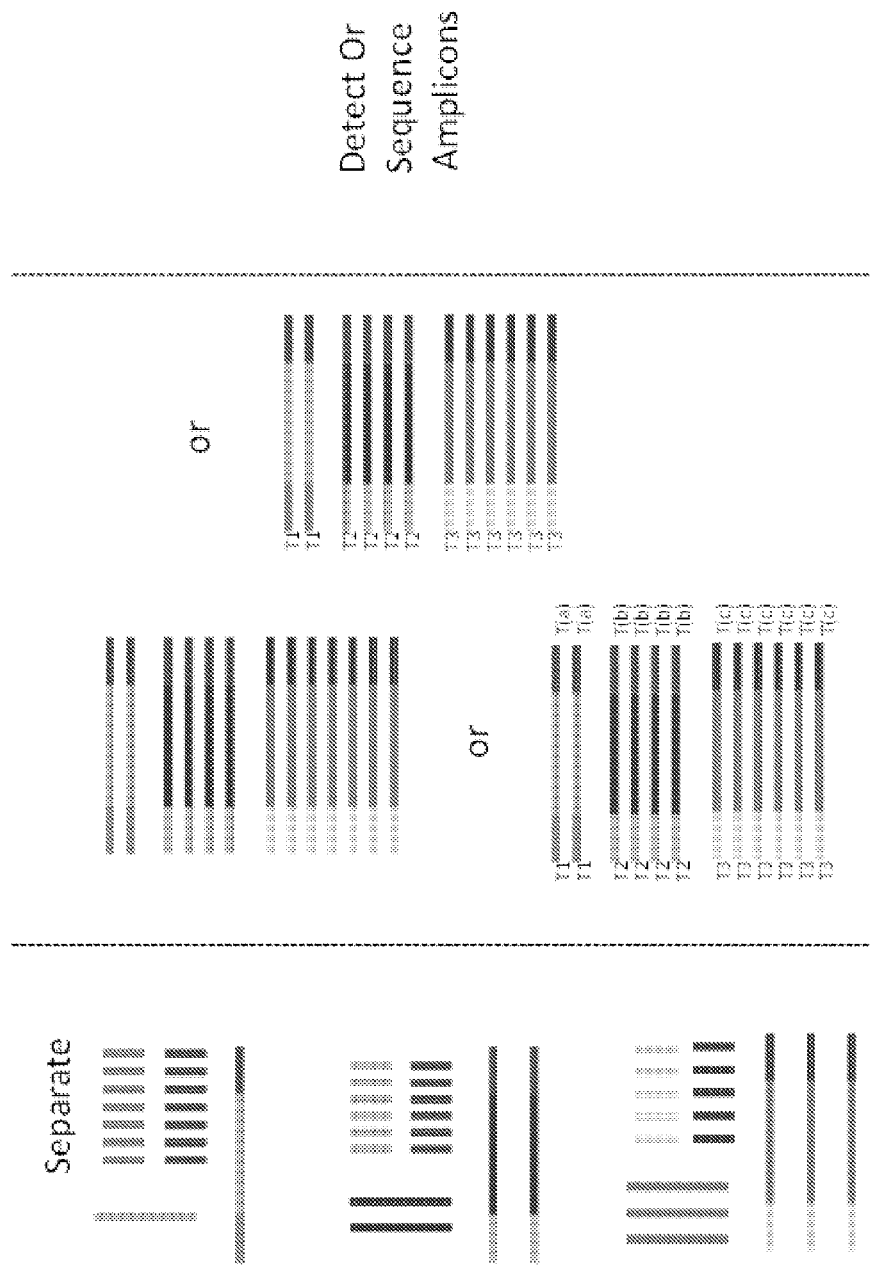

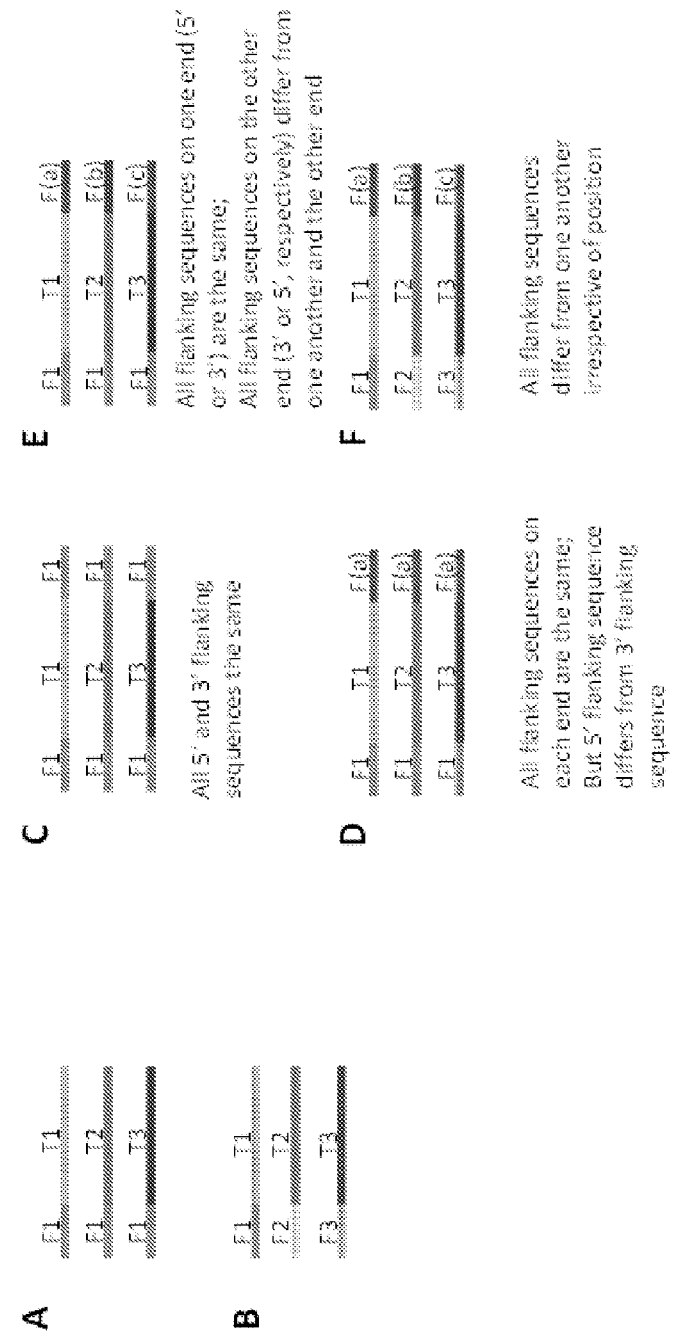

FIG. 10

| Tag(set1) | Tag(set2) | Tag(set3) | Lysate for qNPA reaction(mRNA) | Lysate for qNPA reaction(miRNA) |
|---|---|---|---|---|
| 1 | 9 | 17 | THP1, 50K | |
| 2 | 10 | 18 | THP1, 25K | HepG2, 50K |
| 3 | 11 | | THP1, 10K | HepG2, 10K |
| 4 | 12 | | THP1, 5K | HepG2, 5K |
| 5 | 13 | | HepG2, 50K | THP1, 50K |
| 6 | 14 | 22 | HepG2, 25K | THP1, 10K |
| 7 | 15 | | HepG2, 10K | THP1, 5K |
| 8 | 16 | | HepG2, 5K | |

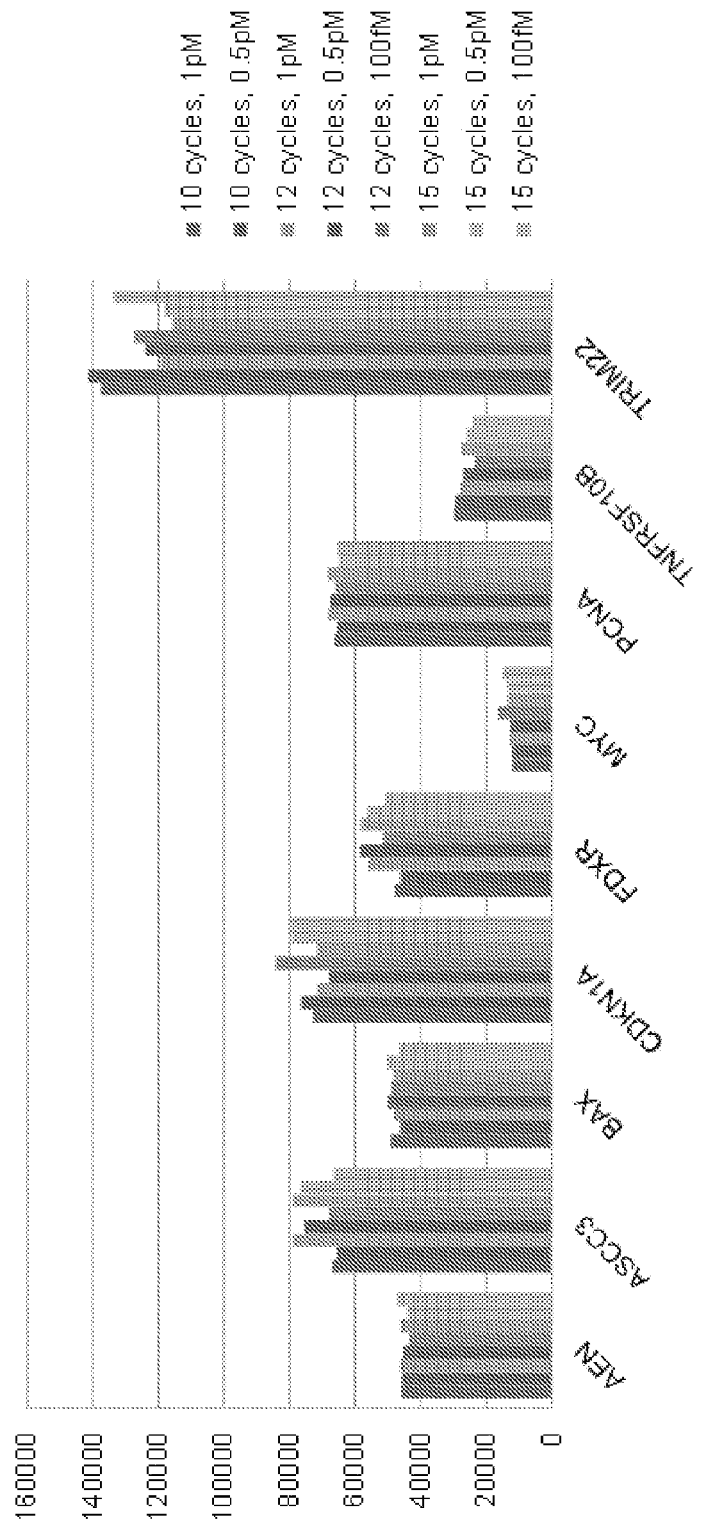

SEQUENCE LISTING

<160> NUMBER OF SEQ ID NOS: 44

<210> SEQ ID NO 1
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 1
tgattcagac cggccg                                                      16

<210> SEQ ID NO 2
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 2
cccggggcgt cttaac                                                      16

<210> SEQ ID NO 3
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 3
ggacgccata tgcgct                                                      16

<210> SEQ ID NO 4
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 4
tgagggctcc gccata                                                      16

<210> SEQ ID NO 5
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 5
aacccgtgac gtgtgc                                                      16

<210> SEQ ID NO 6
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 6
agcatcgccg gtcctg                                                      16

<210> SEQ ID NO 7
<211> LENGTH: 16
<212> TYPE: DNA

```
<213> ORGANISM: Artificial Sequence
<220> FEATURE:
<223> OTHER INFORMATION: exemplary anchor sequence

<400> SEQUENCE: 7
cctgcaaggc tgacgt                                                     16

<210> SEQ ID NO 8
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 8
cagttgtcga ccccgg                                                     16

<210> SEQ ID NO 9
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 9
cggcgcgtcc aattcg                                                     16

<210> SEQ ID NO 10
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 10
atcgatctga gggccc                                                     16

<210> SEQ ID NO 11
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 11
gtacatgcgg cctgca                                                     16

<210> SEQ ID NO 12
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 12
tagccgctcg ctagag                                                     16

<210> SEQ ID NO 13
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 13
cctagtgatg accggc                                                     16
```

```
<210> SEQ ID NO 14
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 14
gtctgagggc aacctc                                                     16

<210> SEQ ID NO 15
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 15
ctagctggct acgcag                                                     16

<210> SEQ ID NO 16
<211> LENGTH: 16
<212> TYPE: DNA
<213> ORGANISM: Artificial Sequence
<220> FEATURE:
<223> OTHER INFORMATION: exemplary anchor sequence

<400> SEQUENCE: 16
gccatccgct tggagc                                                     16

<210> SEQ ID NO 17
<211> LENGTH: 25
<212> TYPE: DNA
<213> ORGANISM: Artificial Sequence
<220> FEATURE:
<223> OTHER INFORMATION: exemplary 5'-end flanking sequence

<400> SEQUENCE: 17
agttcagacg tgtgctcttc cgatc                                           25

<210> SEQ ID NO 18
<211> LENGTH: 25
<212> TYPE: DNA
<213> ORGANISM: Artificial Sequence
<220> FEATURE:
<223> OTHER INFORMATION: exemplary 3'-end flanking sequence

<400> SEQUENCE: 18
gatcgtcgga ctgtagaact ctgaa                                           25

<210> SEQ ID NO 19
<211> LENGTH: 49
<212> TYPE: DNA
<213> ORGANISM: Artificial Sequence
<220> FEATURE:
<223> OTHER INFORMATION: PCR primer

<400> SEQUENCE: 19
aatgatacgg cgaccaccga caggttcaga gttctacagt ccgacgatc                 49

<210> SEQ ID NO 20
<211> LENGTH: 57
<212> TYPE: DNA
<213> ORGANISM: Artificial Sequence
<220> FEATURE:
<223> OTHER INFORMATION: PCR primer
<220> FEATURE:
```

```
<221> NAME/KEY: misc_feature
<222> LOCATION: (25)..(30)
<223> OTHER INFORMATION: nnnnnn at positions 25 to 30 is ATCACG; CGATGT;
      TTAGGC; TGACCA; ACAGTG; GCCAAT; CAGATC; ACTTGA; GATCAG; TAGCTT;
      GGCTAC; CTTGTA; AGTCAA; AGTTCC; ATGTCA; CCGTCC; GTAGAG; GTCCGC;
      GTGAAA; GTGGCC; GTTTCG; CGTACG; GAGTGG; or GGTAGC.

<400> SEQUENCE: 20
caagcagaag acggcatacg agatnnnnnn gtgactggag ttcagacgtg tgctctt      57

<210> SEQ ID NO 21
<211> LENGTH: 56
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 21
caagcagaag acggcatacg agattcacgg tgactggagt tcagacgtgt gctctt       56

<210> SEQ ID NO 22
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 22
caagcagaag acggcatacg agatcgatgt gtgactggag ttcagacgtg tgctctt      57

<210> SEQ ID NO 23
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 23
caagcagaag acggcatacg agatttaggc gtgactggag ttcagacgtg tgctctt      57

<210> SEQ ID NO 24
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 24
caagcagaag acggcatacg agattgacca gtgactggag ttcagacgtg tgctctt      57

<210> SEQ ID NO 25
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 25
caagcagaag acggcatacg agatacagtg gtgactggag ttcagacgtg tgctctt      57

<210> SEQ ID NO 26
<211> LENGTH: 57
<212> TYPE: DNA
```

```
<213> ORGANISM: Artificial Sequence
<220> FEATURE:
<223> OTHER INFORMATION: exemplary primer with a barcode sequence
      present at nucleotides 25-30

<400> SEQUENCE: 26
caagcagaag acggcatacg agatgccaat gtgactggag ttcagacgtg tgctctt          57

<210> SEQ ID NO 27
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 27
caagcagaag acggcatacg agatcagatc gtgactggag ttcagacgtg tgctctt          57

<210> SEQ ID NO 28
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 28
caagcagaag acggcatacg agatacttga gtgactggag ttcagacgtg tgctctt          57

<210> SEQ ID NO 29
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 29
caagcagaag acggcatacg agatgatcag gtgactggag ttcagacgtg tgctctt          57

<210> SEQ ID NO 30
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 30
caagcagaag acggcatacg agattagctt gtgactggag ttcagacgtg tgctctt          57

<210> SEQ ID NO 31
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 31
caagcagaag acggcatacg agatggctac gtgactggag ttcagacgtg tgctctt          57

<210> SEQ ID NO 32
<211> LENGTH: 57
<212> TYPE: DNA
<213> ORGANISM: Artificial Sequence
<220> FEATURE:
```

<223> OTHER INFORMATION: exemplary primer with a barcode sequence
      present at nucleotides 25-30

<400> SEQUENCE: 32
caagcagaag acggcatacg agatcttgta gtgactggag ttcagacgtg tgctctt    57

<210> SEQ ID NO 33
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 33
caagcagaag acggcatacg agatagtcaa gtgactggag ttcagacgtg tgctctt    57

<210> SEQ ID NO 34
<211> LENGTH: 59
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 34
agcaagcaga agacggcata cgagatagtt ccgtgactgg agttcagacg tgtgctctt    59

<210> SEQ ID NO 35
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 35
caagcagaag acggcatacg agatatgtca gtgactggag ttcagacgtg tgctctt    57

<210> SEQ ID NO 36
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 36
caagcagaag acggcatacg agatccgtcc gtgactggag ttcagacgtg tgctctt    57

<210> SEQ ID NO 37
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 37
caagcagaag acggcatacg agatgtagag gtgactggag ttcagacgtg tgctctt    57

```
<210> SEQ ID NO 38
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 38
caagcagaag acggcatacg agatgtccgc gtgactggag ttcagacgtg tgctctt        57

<210> SEQ ID NO 39
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 39
caagcagaag acggcatacg agatgtgaaa gtgactggag ttcagacgtg tgctctt        57

<210> SEQ ID NO 40
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 40
caagcagaag acggcatacg agatgtggcc gtgactggag ttcagacgtg tgctctt        57

<210> SEQ ID NO 41
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 41
caagcagaag acggcatacg agatgttcg gtgactggag ttcagacgtg tgctctt        57

<210> SEQ ID NO 42
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 42
caagcagaag acggcatacg agatcgtacg gtgactggag ttcagacgtg tgctctt        57

<210> SEQ ID NO 43
<211> LENGTH: 57
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 43
caagcagaag acggcatacg agatgagtgg gtgactggag ttcagacgtg tgctctt        57

<210> SEQ ID NO 44
<211> LENGTH: 57
```

```
-continued
<212> TYPE: DNA
<213> ORGANISM: Artificial Sequence
<220> FEATURE:
<223> OTHER INFORMATION: exemplary primer with a barcode sequence
      present at nucleotides 25-30

<400> SEQUENCE: 44
caagcagaag acggcatacg agatggtagc gtgactggag ttcagacgtg tgctctt        57
```

QUANTITATIVE NUCLEASE PROTECTION ASSAY (QNPA) AND SEQUENCING (QNPS) IMPROVEMENTS

CROSS REFERENCE TO RELATED APPLICATIONS

This is the U.S. National Stage of International Application No. PCT/US2012/035260, filed Apr. 26, 2012, which was published in English under PCT Article 21(2), which in turn claims the benefit of U.S. Provisional Application No. 61/482,486, filed May 4, 2011, U.S. Provisional Application No. 61/537,492, filed Sep. 21, 2011, and U.S. Provisional Application No. 61/576,143, filed Dec. 15, 2011, all herein incorporated by reference.

ACKNOWLEDGMENT OF GOVERNMENT SUPPORT

This invention was made with government support under Grant No. 5R43HG005949-02 awarded by The National Institutes of Health, National Human Genome Research Institute. The government has certain rights in the invention.

FIELD

The present disclosure provides improved quantitative nuclease protection assay (qNPA) and quantitative nuclease protection sequencing (qNPS) methods. Such methods can be used in the identification, detection and/or sequencing of nucleic acid targets.

BACKGROUND

Although methods of detecting and sequencing nucleic acid molecules are known, there is still a need for methods that permit analysis of multiple samples or multiple sequences simultaneously or contemporaneously. Methods of multiplexing nucleic acid molecule detection or sequencing reactions have not been realized at the most desired performance or simplicity levels.

SUMMARY

Methods are provided that greatly improve prior quantitative nuclease protection assay (qNPA) and quantitative nuclease protection sequencing (qNPS) methods and represent an improvement to current nucleic acid detection and sequencing methods. These methods can be used in the identification, detection and/or sequencing of nucleic acid molecule targets. The methods utilize a nuclease protection probe that includes one or more flanking sequences (NPPFs). The NPPFs include a sequence that is complementary to all or a portion of the target nucleic acid molecule, thus permitting specific binding or hybridization between the target nucleic acid molecule and the NPPF. For example, the region of the NPPF that is complementary to a region of the target nucleic acid molecule binds to or hybridizes to that region of the target nucleic acid molecule with high specificity (and in some examples can also bind to a region of a bifunctional linker). The NPPFs further include one or more flanking sequences at the 5'-end and/or 3'-end of the NPPF. Thus, the one or more flanking sequences are located 5', 3', or both, to the sequence complementary to the target nucleic acid molecule. If the NPPF includes a flanking sequence at both the 5'-end and 3'-end, in some examples the sequence of each NPPF is different and not complementary. The flanking sequence(s) includes several contiguous nucleotides having a sequence (such as a sequence of at least 12 nucleotides) not found in a nucleic acid molecule present in the sample, and provide a universal hybridization and/or amplification sequence. This universal hybridization and/or amplification sequence, when having a sequence complementary to at least a portion of an amplification primer, permits multiplexing, as the same amplification primers can be used to amplify NPPFs specific for different target nucleic acid molecules. It also provides a universal hybridization sequence for all NPPFs, which can be used to add a detectable label to the NPPF or to capture and concentrate NPPFs. For example, if the same flanking sequence is present on NPPFs specific for different target nucleic acid molecules, the same primer can be used to amplify any NPPF having the same flanking sequence, even if the NPPF targets a different nucleic acid molecule. For example, the flanking sequence can be used to capture NPPFs, such as onto a surface. The flanking sequence can contain a variable sequence, such as a sequence that is specific for each specific NPPF and can be used to either capture that NPPF on a surface or for other purposes, such as to identify the NPPF. Thus, in some examples, the disclosed methods are used to detect or sequence several different target nucleic acid molecules in a sample using a plurality of NPPFs, wherein each NPPF specifically binds to a particular target nucleic acid molecule. In one example, the disclosed methods are used to detect or sequence at least one target nucleic acid molecule in a plurality of samples simultaneously.

The disclosure provides methods for detecting or determining a sequence of at least one target nucleic acid molecule in a sample. The methods can include contacting the sample (such as one that has been heated to denature nucleic acid molecules in the sample) with at least one NPPF under conditions sufficient for the NPPF to specifically bind to the target nucleic acid molecule. The NPPF molecule includes a sequence complementary to all or a portion of the target nucleic acid molecule. This permits specific binding or hybridization between the NPPF and the target nucleic acid molecule. The method further includes contacting the sample with one or more nucleic acid molecules having a sequence that is complementary to all or a portion of a flanking sequence (such a molecule is referred to herein as a CFS) under conditions sufficient for the flanking sequence to specifically bind or hybridize to the CFS. More than one CFS can be used to hybridize to an entire flanking sequence (e.g., multiple individual CFSs can be hybridized to a single flanking sequence, such that the entire flaking sequence is covered). This results in the generation of NPPF molecules that have bound (hybridized) thereto the target nucleic acid molecule, as well as the CFS(s), thereby generating a double-stranded molecule, which can include at least four contiguous oligonucleotide sequences, with all bases engaged in hybridization to a complementary base After allowing the target nucleic acid molecule and the CFS(s) to bind to the NPPFs, the method can further include contacting the sample with a nuclease specific for single-stranded (ss) nucleic acid molecules (or ss regions of a nucleic acid molecule) under conditions sufficient to remove nucleic acid bases that are not hybridized to a complementary base. Thus for example, NPPFs that have not bound target nucleic acid molecule or CFSs, as well as unbound target nucleic acid molecules, other ss nucleic acid molecules in the sample, and unbound CFSs, will be degraded. This generates a digested sample that includes intact NPPFs present as double-stranded adducts with CFS(s) and target nucleic acid molecule. In some examples, the method further includes increasing the pH of the sample and/or heating it, to dissociate or remove target nucleic acid molecules and CFSs that are bound to the NPPFs.

The NPPFs that were bound to the target nucleic acid molecule and CFSs, and thus survived treatment with the nuclease, can be amplified and/or labeled. NPPFs in the digested sample can be amplified using one or more amplification primers, thereby generating NPPF amplicons. At least one amplification primer includes a region that is complementary to all or a portion of the flanking sequence of the NPPF. In some examples, the NPPF includes a flanking sequence at both the 5'-end and 3'-end, and two amplification primers are used, wherein one amplification primer has a region that is complementary to the 5'-end flanking sequence and the other amplification primer has a region that is complementary to the 3'-end flanking sequence.

Alternatively, instead of using the NPPFs that survived treatment with the nuclease, the target nucleic acid strand that was hybridized to the NPPF (such as a DNA strand) can be used directly, such as amplified, labeled, detected, sequenced, or combinations thereof. For example, the target nucleic acid strand can be amplified using one or more amplification primers, thereby generating target amplicons, which can be detected and/or sequenced. Thus, although NPPF amplicons are referred to herein, one will appreciated that target amplicons can be substituted therefor.

The resulting amplicons (or portion thereof, such as a 3'-portion) can then be sequenced or detected. In one example, amplicons are attached to a substrate. For example, the substrate can include at least one capture probe having a sequence complementary to all or a portion of a flanking sequence on the NPPF amplicon, thus permitting capture of the NPPF amplicons having the complementary flanking sequence. Alternatively, the substrate can include at least one anchor in association with a bifunctional linker, wherein the bifunctional linker includes a first portion which specifically binds to the anchor and a second portion which specifically binds to a portion of one of the NPPF amplicons. The captured NPPF amplicons can then be sequenced or detected, thereby determining the sequence of, or detecting, the at least one target nucleic acid molecule in the sample.

In other examples, the NPPF amplicons are detected or sequenced without capture onto an array. For example, the NPPF amplicons can be transferred to a sequencing platform.

The NPPF can be labeled with a detectable label, for example during amplification, or as a step without amplification. Alternatively, one or both flanking regions can be used to hybridize a detectable label to the NPPF.

The foregoing and other objects and features of the disclosure will become more apparent from the following detailed description, which proceeds with reference to the accompanying figures.

BRIEF DESCRIPTION OF THE DRAWINGS

FIG. 1 is a schematic diagram showing an exemplary nuclease protection probe having flanking sequences (NPPF), 100. The NPPF 100 includes a region 102 having a sequence that specifically binds to the target nucleic acid sequence and to a bifunctional (or programming) linker. The NPPF also includes a 5'-flanking sequence 104 and a 3'-flanking sequence 106.

FIG. 2 is a schematic diagram showing the initial steps of a method of using the NPPFs 202 to detect or sequence a nucleic acid molecule using the disclosed methods. The dashed bars represent an NPPF specific for a first target (in some examples the NPPF is labeled with biotin (B)), the solid gray bars represent an NPPF specific for a second target (in some examples the NPPF is labeled with B), the dotted green bars represent nucleic acid molecules that are complementary to the flanking sequences (CFS) 204 of the NPPF, and the solid black bars represent the target nucleic acid 200 (e.g., DNA or RNA). The biotin can be added during amplification by using a primer that is biotin (or digoxin) labeled. Alternatively, the primer can be labeled with another label (such as a fluorophore), resulting in an NPPF that is labeled. (1) A sample (such as cells or FFPE tissue) is contacted with sample disruption buffer (for example to permit lysis of cells and tissues in the sample) and incubated with the NPPFs and CFSs. (2) Unbound (e.g., single-stranded) nucleic acid is digested with a nuclease specific for ss nucleic acid molecules (such as S1 nuclease). (3) The nuclease can be inactivated and the NPPFs dissociated from bound target molecules and bound CFSs, for example by addition of base and heating. (4) The remaining NPPFs are amplified, for example by using PCR with appropriate primers 208. In some examples, the primers 208 include a detectable label, to permit labeling of the resulting amplicons 210. The resulting amplicons 210 can be detected (FIG. 3) or sequenced (FIG. 4).

FIG. 3 is a schematic diagram showing how NPPF amplicons 210 can be (5) captured on an array 212 that includes bifunctional linkers 216 associated with anchors 214 or that includes nucleic acid capture molecules 220. The bifunctional linker 216 includes a region that is complementary to a region of the NPPF amplicons 210 (such as complementary to a sequence that had been hybridized to the target nucleic acid), and a region that is complementary to a portion of the anchor. The nucleic acid capture molecules 220 include a region that is complementary to a region of the NPPF amplicons 210 (such as to a flanking sequence or portion thereof). (6) In one example, avidin-horseradish peroxidase (HRP) is used to detect the bound NPPFs and (7) the array is imaged following addition of substrate. The location of the signal on the array allows identification of signal generated by a target nucleic acid molecule.

FIG. 4 is a schematic diagram showing that NPPF amplicons 210 can be (5) sequenced.

FIGS. 5A-B are schematic diagrams showing details of the nucleic acid molecules as they are processed during the steps of a method of using the NPPFs 402 to detect or sequence a nucleic acid molecule using the disclosed methods. The longer solid colored bars represent target nucleic acid molecules 400, the bars with lighter and darker colors on their ends are NPPFs 402 specific for a target, with the different colored ends 404 representing the flanking sequences. The color of the target is matched to the color of its corresponding NPPF. The shorter solid color bars represent nucleic acid molecules that are complementary to the flanking sequences (CFS) 406 of the NPPF.

FIGS. 6A-F are schematic drawings showing exemplary embodiments of NPPF molecules, including embodiments with (A and B) a flanking sequence only on one end of the NPPF or (C-F) with flanking sequences on both ends of the NPPF.

FIG. 10 is a table showing input material, NPPF types, and the experiment tags used to sequence cell line lysates. Each experiment was performed in duplicate or triplicate.

FIG. 14 is a bar graph of sequencing counts from NPPFs that were amplified using a range of PCR cycle numbers and input amounts. Each bar represents one qNPA experiment using one of three different input concentrations and one of three PCR cycle numbers. All experiments were normalized so that the total number of reads was set equal, to facilitate comparing the results.

SEQUENCE LISTING

Figure 7:
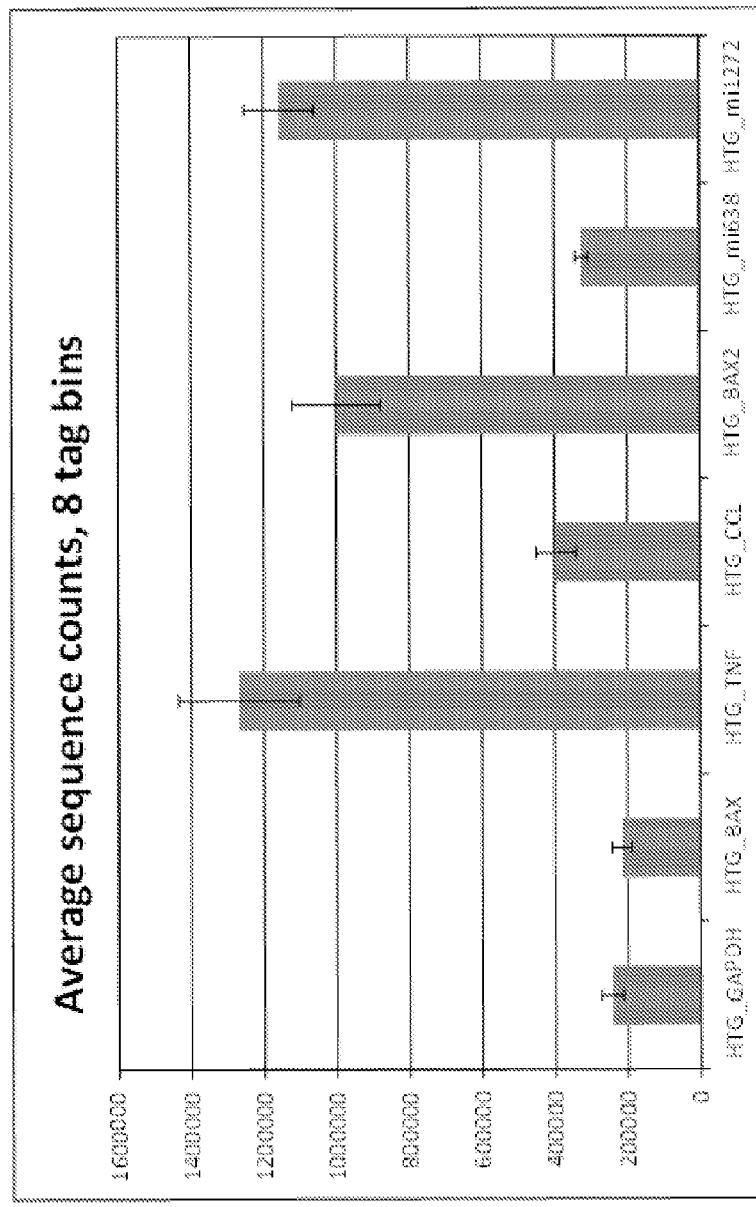
FIG. 7 is a bar graph showing the number of amplicons detected for each of seven unique NPPFs. Error bars represent one standard deviation from the mean.
Figure 8:
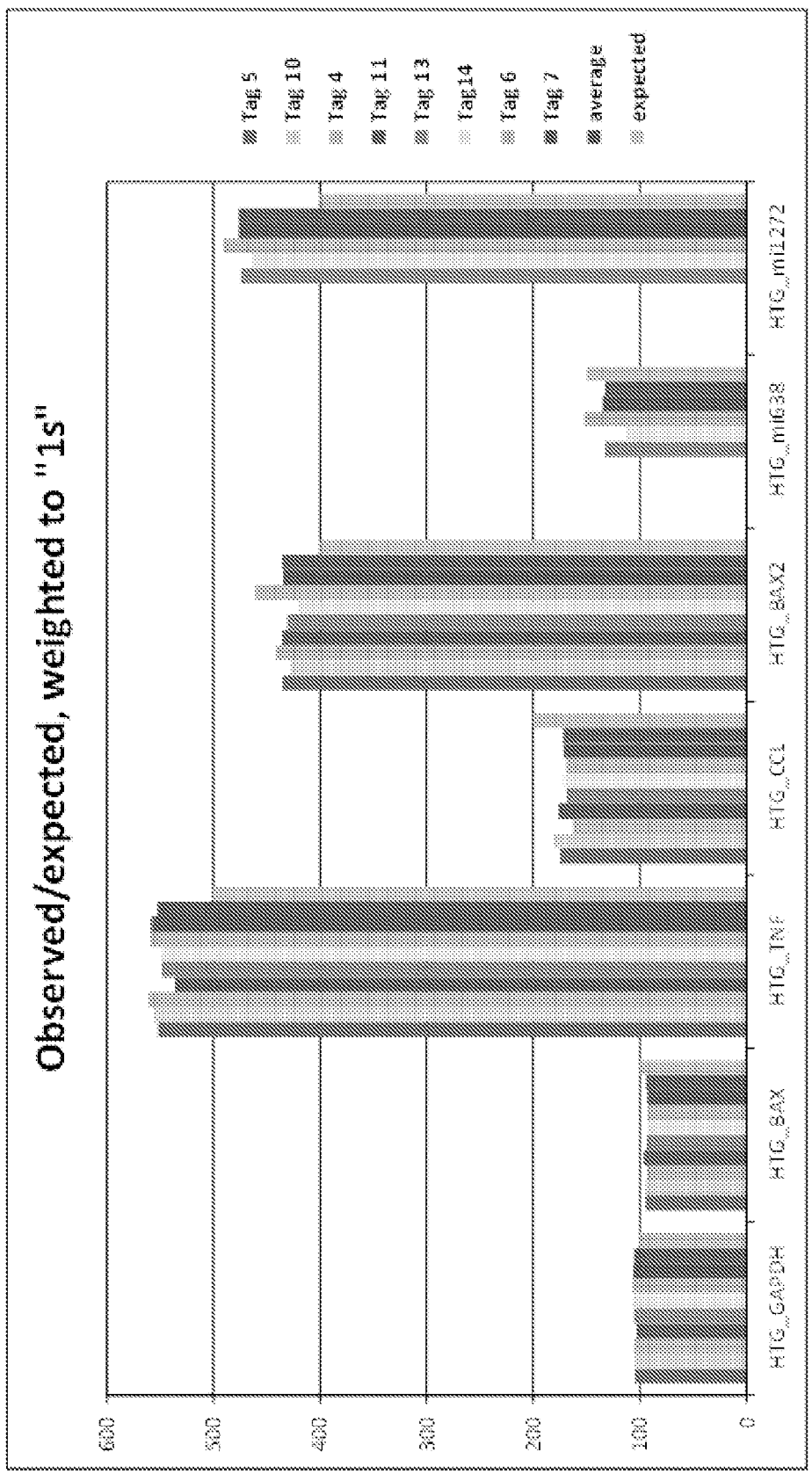
FIG. 8 is a bar graph comparing the observed ratios for each of the 7 unique NPPFs, to the ratios expected based on the amount of NPPF added to the original PCR reaction.
Figure 9:
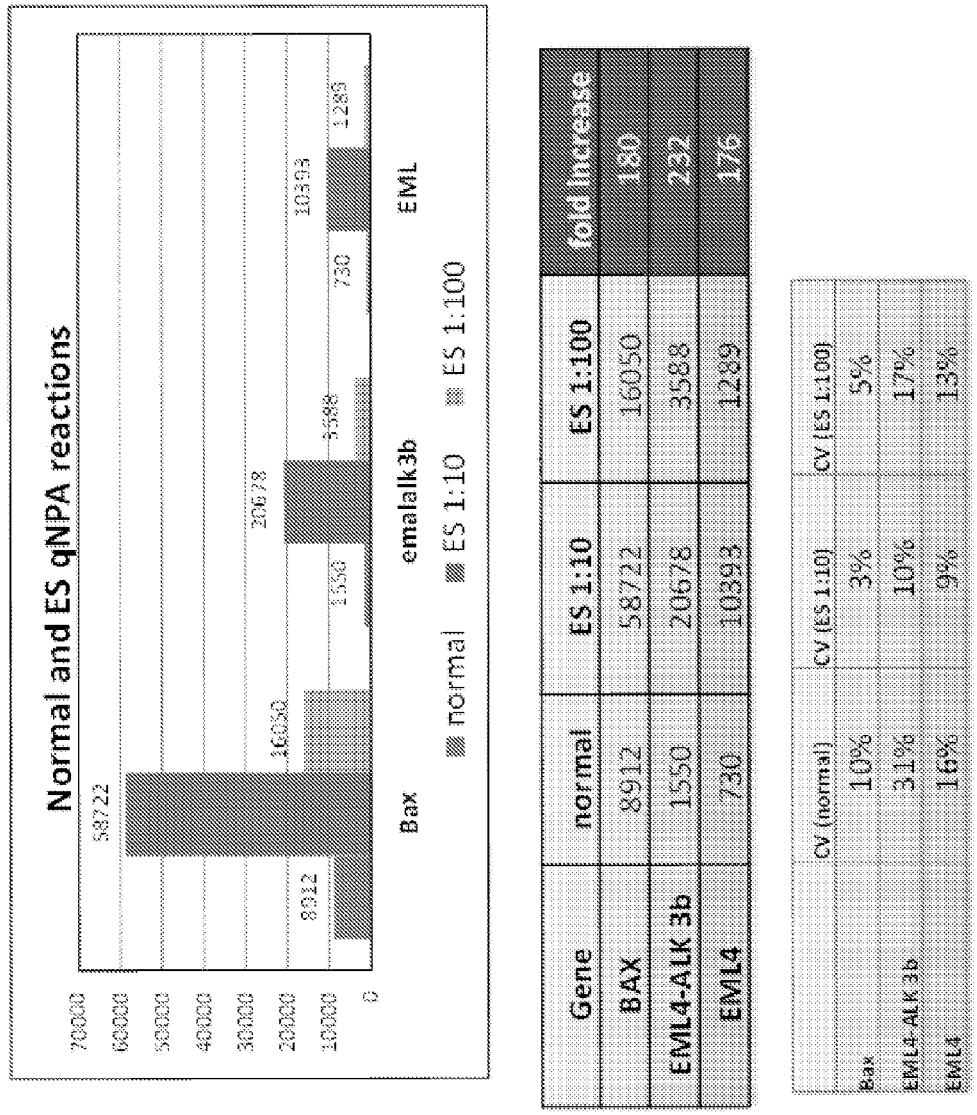
FIG. 9 is a bar graph and tables comparing the detected NPPF probes without (normal) or with amplification (extreme sensitivity, ES). Each experiment was performed in triplicate. The PCR amplified reactions were diluted before capture and measurement.

The nucleic acid sequences listed herein are shown using standard letter abbreviations for nucleotide bases, as defined in 37 C.F.R. 1.822. Only one strand of each nucleic acid sequence is shown, but the complementary strand is understood as included by any reference to the displayed strand. In the provided sequences:

SEQ ID NOS: 1-16 provide exemplary anchor nucleic acid sequences that can be used with the disclosed methods.

SEQ ID NOS: 17 and 18 provide exemplary 5'- and 3'-flanking sequences, respectively, which can be used with an NPPF.

SEQ ID NOS: 19 and 20 provide exemplary PCR primers.

SEQ ID NOS 21-44 provide exemplary primers containing barcode sequences present at nucleotides 25-30.

DETAILED DESCRIPTION

I. Overview

The present disclosure provides improved methods of detecting or sequencing a target nucleic acid molecule, which permits multiplexing. The disclosed methods provide several improvements over currently available sequencing and detection methods. For example, because the methods require less processing of the target nucleic acid molecules, bias introduced by such processing can be reduced or eliminated. For example, in current methods, for example when the target is an RNA, methods typically employ steps to isolate or extract the RNA from a sample, subject it to RT-PCR, ligate the RNA, or combinations thereof. In the disclosed methods, such steps are not required. As a result, the methods permit one to analyze a range of sample types not otherwise amenable to detection sequencing. In addition, this results in less loss of the RNA from the sample, providing a more accurate result. It also reduces enzyme bias. The disclosed methods also provide for targeted detection and sequencing of a desired nucleic acid molecule. This greatly simplifies data analysis. Current whole genome sequencing methods are challenged by the large amount of data generated, and the need for complicated bioinformatics. Although costs of sequencing have decreased, the ability to determine sequences is outrunning the ability of researchers to store, transmit and analyze the data. As a result, there is commonly more data generated than can be analyzed in a reasonable amount of time. Because the disclosed methods are targeted, it can overcome these obstacles. For example, the amount of data generated is simplified, as only a portion of the target needs to be detected or sequenced. Long reads of nucleotides are not required, nor do fragments of sequences need to be properly aligned to a reference sequence. In addition, the results can be simply counted, without the need for complicated bioinformatics analysis.

For example, the method can be used to detect DNA or RNA, mutations such as gene fusions, insertions or deletions, tandem repeats, single nucleotide polymorphisms (SNPs), and DNA methylation. The method uses a probe, referred to herein as a nuclease protection probe comprising a flanking sequence (NPPF). The use of NPPF permits multiplexing, and conserves the stoichiometry of the detected or sequenced target nucleic acid molecule, because the flanking sequences on the probe permit universal primer binding sites for amplification and permit addition of sequencing adapters and experimental tags (at either the 3'- or the 5'-end, or at both ends for example to increase multiplexing), without destroying the stoichiometry. As the flanking sites can be universal, the same primers can be used to amplify any NPPF for any target sequence, thus allowing for multiplexing and conservation of stoichiometry. In one example, by amplifying from both ends of the NPPF, the disclosed methods provide greater specificity than prior qNPA and qNPS methods. Only NPPFs with intact 3'- and 5'-flanking sequences will be amplified exponentially, while NPPFs cleaved by the nuclease will not be amplified sufficiently to be sequenced or detected.

In addition, the primers permit addition of tags (such as experiment tags to permit the identification of the target without necessitating the sequencing of the entire NPPF itself or to permit samples from different patients to be combined into a single run, at either the 3'- or the 5'-end, or at both ends for example to increase multiplexing, as well as sequencing adapters to permit attachment of a sequence needed for a particular sequencing platform and formation of colonies for some sequencing platforms). The use of NPPFs also simplifies the complexity of the sample that is analyzed (e.g., sequenced), as it reduces the sample containing for example whole genes to the NPPFs (or NPPF or target amplicons). The sequencing of NPPFs (or the target hybridized to the NPPF) simplifies data analysis compared to that required for other sequencing methods, reducing the algorithm to simply count the matches to the NPPFs that were added to the sample, rather than having to match sequences to the genome and deconvolute the multiple sequences/gene that are obtained from standard methods of sequencing. In some examples, the disclosed methods increase the signal obtained as compared to prior qNPA and qNPS methods, such as an increase of at least 10-fold, at least 100-fold, at least 125-fold, at least 150-fold, or at least 200-fold without substantial dilution of the NPPF product before performing the amplification.

In one example, the disclosure provides methods for detecting at least one target nucleic acid molecule in a sample (such as at least 2, at least 3, at least 4, at least 5, at least 10, at least 20, at least 30, at least 40, at least 50, or at least 100 target nucleic acid molecules) or a determining a sequence of at least one target nucleic acid molecule in a sample. In some examples, the sample is heated to denature nucleic acid molecules in the sample, for example to permit subsequent hybridization between the NPPF and the target nucleic acid molecules in the sample. In some examples, the sample is a lysed sample. In some examples, the sample is a fixed sample (such as a paraffin-embedded formalin-fixed (FFPE) sample, hematoxylin and eosin stained tissues, or glutaraldehyde fixed tissues). For example, the target nucleic acid molecules can be fixed, cross-linked, or insoluble.

The methods can include contacting the sample with at least one nuclease protection probe comprising a flanking sequence (NPPF) under conditions sufficient for the NPPF to specifically bind to the target nucleic acid molecule. In some examples, the disclosed methods sequence or detect at least one target nucleic acid molecule in a plurality of samples simultaneously or contemporaneously. In some examples, the disclosed methods sequence or detect two or more target nucleic acid molecules in a sample (for example simultaneously or contemporaneously). In such an example, the sample is contacted with a plurality of NPPFs, wherein each NPPF specifically binds to a particular target nucleic acid molecule. For example, if there are 10 target nucleic acid molecules, the sample can be contacted with 10 different NPPFs each specific for one of the 10 targets. In some examples, at least 10 different NPPFs are incubated with the sample. However, it is appreciated that in some examples, more than one NPPF (such as 2, 3, 4, 5, 10, 20, or more) specific for a single target nucleic acid molecule can be used, such as a population of NPPFs that are specific for different regions of the target, or a population of NPPFs that can bind to the target and variations thereof (such as those having mutations or polymorphisms).

The NPPF molecule includes a 5'-end and a 3'-end, as well as a sequence in between that is complementary to all or a part of the target nucleic acid molecule. This permits specific binding or hybridization between the NPPF and the target nucleic acid molecule. For example, the region of the NPPF that is complementary to a region of the target nucleic acid molecule binds to or hybridizes to that region of the target nucleic acid molecule with high specificity. The NPPF can be complementary to all of, or a portion of, the target nucleic acid sequence. The NPPF molecule further includes one or more flanking sequences, which are at the 5'-end and/or 3'-end of the NPPF. Thus, the one or more flanking sequences are located 5', 3', or both, to the sequence complementary to the target nucleic acid molecule. Each flanking sequence includes several contiguous nucleotides, generating a sequence that is not found in a nucleic acid molecule present in the sample (such as a sequence of at least 12 contiguous nucleotides). If the NPPF includes a flanking sequence at both the 5'-end and 3'-end, in some examples the sequence of each NPPF is different and not complementary to each other.

The flanking sequence(s) provide a universal hybridization/amplification sequence, which is complementary to at least a portion of an amplification primer. In some examples, the flanking sequence can include (or permit addition of) an experimental tag, sequencing adapter, or combinations thereof. For example, the experimental tag can be a sequence complementary to a capture probe that permits capture NPPFs, for example onto a surface (such as at a specific spot on the surface, or to a specific bead). In some examples, the experimental tag can be a sequence that identifies an NPPF, such as a tag specific for a particular patient or target sequence, for example to permit one to distinguish or group such tagged NPPFs. In some examples, the sequencing adapter a sequence that permits an NPPF NPPF amplicon to be used with a particular sequencing platform.

The NPPF can be any nucleic acid molecule, such as a DNA or RNA molecule, and can include unnatural bases. In some examples the NPPF is at least 35 nucleotides, such as 40 to 80 or 50 to 150 nucleotides. The portion of the NPPF that is complementary to a region of the target nucleic acid molecule can be at least 6 nucleotides in length, such as at least 10, at least 25, or at least 60, such as 6 to 60 nucleotides in length. The flanking sequence(s) of the NPPF can be at least 6 nucleotides, at least 12 nucleotides, or at least 25 nucleotides, such as 12 to 50 nucleotides in length. In some examples, the NPPF includes two flanking sequences: one at the 5'-end and the other at the 3'-end. In some examples, the flanking sequence at the 5'-end differs from the flanking sequence at the 3'-end. In addition, if the NPPF includes two flanking sequences, ideally the two flanking sequences have a similar melting temperature (Tm), such as a Tm of +/−5° C.

The method further includes contacting the sample with a nucleic acid molecule having a sequence that is complementary to the flanking sequence (such a molecule is referred to herein as a CFS) under conditions sufficient for the flanking sequence to specifically bind or hybridize to the CFS. One skilled in the art will appreciate that instead of using a single CFS to protect a flanking sequence, multiple CFSs can be used to protect a flanking sequence. This results in the generation of NPPF molecules that have bound thereto the target nucleic acid molecule, as well as the CFS, thereby generating a double-stranded molecule that includes at least three contiguous oligonucleotide sequences, with all bases engaged in hybridization to a complementary base, which bases of the NPPF and CFSs can include unnatural bases. The CFS hybridizes to and thus protects its corresponding flanking sequence from digestion with the nuclease in subsequent steps. In some examples, each CFS is the exact length of its corresponding flanking sequence. In some examples, the CFS is completely complementary to its corresponding flanking sequence. However, one skilled in the art will appreciate that the 3'-end of a CFS that protects a 5'-end flanking sequence or the 5'-end of a CFS that protects the 3'-end flanking sequence can have had a difference, such as one nucleotide at each of these positions.

After allowing the target nucleic acid molecule, as well as the CFS(s), to bind to the NPPFs, the method can further include contacting the sample with a nuclease specific for single-stranded (ss) nucleic acid molecules or ss regions of a nucleic acid molecule, such as S1 nuclease, under conditions sufficient to remove nucleic acid bases that are not hybridized to a complementary base. Thus for example, NPPFs that have not bound target nucleic acid molecule or CFSs, as well as unbound target nucleic acid molecules, other ss nucleic acid molecules in the sample, and unbound CFSs, will be degraded. This generates a digested sample that includes intact NPPFs present as double stranded adducts hybridized to CFSs and target nucleic acid. In some examples, for example if the NPPF is composed of DNA, the nuclease can include an exonuclease, an endonuclease, or a combination thereof.

In some examples, the method further includes increasing the pH of the sample and/or heating it, for example to inactivate the nuclease, to remove target nucleic acid molecule and CFSs that are bound to the NPPFs, or combinations thereof. In some examples, the method includes releasing the target nucleic acid (such as a DNA) from the NPPF, and then further analyzing the released target (such as detecting or sequencing the target). In some examples the target nucleic acid is DNA, and the DNA is amplified prior to its detection or sequencing.

The NPPFs that were bound to the target nucleic acid molecule and CFSs and thus survived treatment with the nuclease can be amplified, for example using PCR amplification. NPPFs in the digested sample can be amplified using one or more amplification primers, thereby generating NPPF amplicons. At least one amplification primer includes a region that is complementary to an NPPF flanking sequence. In some examples, the NPPF includes a flanking sequence at both the 5'-end and 3'-end, and two amplification primers are used, wherein one amplification primer has a region that is complementary to the 5'-end flanking sequence and the other amplification primer has a region that is complementary to the 3'-end flanking sequence. One or both of the amplification primers can include a sequence that permits attachment of an experimental tag or sequencing adapter to the NPPF amplicon during the amplification, and one or both primers can be labeled to permit labeling of the NPPF amplicon. In some examples, both an experimental tag and a sequencing adapter are added, for example at opposite ends of the NPPF amplicon. For example, the use of such primers can generate an experimental tag or sequence tag extending from the 5'-end or 3'-end of the NPPF amplicon, or from both the 3'-end and 5'-end to increase the degree of multiplexing possible. The experimental tag can include a unique nucleic acid sequence that permits identification of a sample, subject, or target nucleic acid sequence. In some examples, the amplification primer contains an experimental tag that permits capture of the NPPF amplicon onto a substrate (for example by hybridization to a probe on the substrate having a sequence complementary to the capture sequence on the NPPF amplicon). The sequencing adapter can include a nucleic acid sequence that permits capture of the resulting NPPF onto a sequencing platform. For example, the amplification primer can include a sequence that permits attachment of a poly-A or poly T sequence tag which can facilitate amplification once captured onto the sequencing chip. In some examples, the amplification primer is used to label the NPPF amplicon. In other examples, one or both flanking regions are used to hybridize a detectable label to the NPPF, such as with a labeled probe (for example without amplification).

The resulting NPPF (or target) amplicons (or portion thereof, such as a 3'-portion) can then be sequenced or detected, thereby determining the sequence of, or detecting, the at least one target nucleic acid molecule in the sample.

In one example, the NPPF amplicons (or portion thereof) is sequenced. Any method can be used to sequence the NPPF amplicons, and the disclosure is not limited to particular sequencing methods. In some examples, the sequencing method used is Solexa® sequencing, 454® sequencing, chain termination sequencing, dye termination sequencing, or pyrosequencing. In some examples, single molecule sequencing is used. In some examples where the NPPF amplicons are sequenced, the method also includes comparing the obtained NPPF sequence to a reference sequence database; and determining the number of each identified NPPF sequence.

In some examples, the NPPF amplicons are detected. In such examples, the method can include contacting the NPPF amplicons with a surface, such as one having multiple spatially discrete regions. In one example, the NPPF amplicons are captured by one or more nucleic acid capture molecules on the surface, wherein the sequences of the nucleic acid capture molecules on the surface are complementary to at least a portion of a flanking sequence on the NPPF amplicon. This complementarity permits hybridization and binding of the NPPF amplicons to the capture molecules on the surface. Such capture molecules can be directly conjugated to the surface. The NPPF amplicons are incubated or contacted with the surface under conditions sufficient for the NPPF amplicons to specifically bind to the capture molecules on the surface. In some examples, the NPPF amplicons are contacted with a population of surfaces, wherein the population of surfaces includes subpopulations of surfaces (such as a population of beads), and wherein each subpopulation of surfaces comprises at least one nucleic acid capture molecule complementary to at least a portion of a flanking sequence on the NPPF amplicon. Thus, this permits capture of all NPPFs having a sequence complementary to the capture molecules on the surface, regardless of the sequence targeted by the NPPF. The bound NPPF amplicons can then be detected. In some examples, this step is used to purify or concentrate NPPF amplicons (for example from a mixture containing primers), and the NPPF amplicons can be subsequently released from the surface, for example by reversing hybridization (such as by increasing temperature to melt off the captured NPPFs or by changing pH and the temperature), and the NPPF amplicons analyzed.

In another example, the NPPF amplicons are captured onto a surface by using anchors and bifunctional linkers. The surface can include a plurality of regions, each region including at least one anchor in association with a bifunctional linker. The bifunctional linker includes a first portion which specifically binds to the anchor and a second portion which specifically binds to or hybridizes to at least a portion of one of the NPPF amplicons. The NPPF amplicons are incubated or contacted with the surface under conditions sufficient for the NPPF amplicons to specifically bind to the second portion of the bifunctional linker. In some examples, the NPPF amplicons are contacted with a population of surfaces, wherein the population of surfaces includes subpopulations of surfaces (such as a population of beads), and wherein each subpopulation of surfaces comprises at least one anchor in association with a bifunctional linker. The bound NPPF amplicons can then be detected.

In addition, the NPPF amplicon can include a detectable label thereby permitting its detection. In some examples, such a label is introduced during amplification. In specific examples, the detectable label is a hapten, a fluorescent molecule, an enzyme, or a radioisotope. For example, biotin present on an NPPF amplicon can be detected by contacting the NPPF amplicons with avidin or streptavidin conjugated to horseradish peroxidase or alkaline phosphatase.

II. Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics,* 2nd Edition, 2003 (ISBN: 0-471-26821-6).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

To facilitate review of the various embodiments of this disclosure, the following explanations of specific terms are provided:

3' end: The end of a nucleic acid molecule that does not have a nucleotide bound to it 3' of the terminal residue.

5' end: The end of a nucleic acid sequence where the 5' position of the terminal residue is not bound by a nucleotide.

Amplifying a nucleic acid molecule: To increase the number of copies of a nucleic acid molecule, such as an NPPF or portion thereof. The resulting products are called amplification products or amplicons. An example of in vitro amplification is the polymerase chain reaction (PCR), in which a sample (such as a sample containing NPPFs) is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule.

Binding or stable binding (of a nucleic acid): A first nucleic acid molecule (such as an NPPF) binds or stably binds to another nucleic acid molecule (such as a target nucleic acid molecule) if a sufficient amount of the first nucleic acid molecule forms base pairs or is hybridized to the other nucleic acid molecule, for example the binding of a NPPF to its complementary target nucleic acid sequence.

Binding can be detected by either physical or functional properties. Binding between nucleic acid molecules can be detected by any procedure known to one skilled in the art, including both functional (for example reduction in expression and/or activity) and physical binding assays.

Complementary: Ability to from base pairs between nucleic acids. Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acids or two distinct regions of the same nucleic acid.

"Specifically hybridizable" and "specifically complementary" are terms that indicate a sufficient degree of complementarity such that stable and specific binding occurs between the probe (for example, an NPPF) or its analog and the nucleic acid target (such as DNA or RNA target). The probe or analog need not be 100% complementary to its target sequence to be specifically hybridizable. A probe or analog is specifically hybridizable when there is a sufficient degree of complementarity to avoid non-specific binding of the probe or analog to non-target sequences under conditions where specific binding is desired, for example in the methods disclosed herein.

Conditions sufficient for: Any environment that permits the desired activity, for example, that permit specific binding or hybridization between two nucleic acid molecules (such as an NPPF and a target nucleic acid, an NPPF and a CFS, or between an NPPF and a bifunctional linker) or that permit a nuclease to remove (or digest) unbound nucleic acids.

Contact: Placement in direct physical association; includes both in solid and liquid form. For example, contacting can occur in vitro with a nucleic acid probe (e.g., an NPPF) and biological sample in solution.

Detect: To determine if an agent (such as a signal, particular nucleotide, amino acid, nucleic acid molecule, and/or organism) is present or absent. In some examples, this can further include quantification. For example, use of the disclosed methods permit detection of target nucleic acid molecules in a sample.

Detectable label: A compound or composition that is conjugated directly or indirectly to another molecule (such as a nucleic acid molecule, for example an NPPF or an amplification primer/probe) to facilitate detection of that molecule. Specific, non-limiting examples of labels include fluorescent and fluorogenic moieties, chromogenic moieties, haptens, affinity tags, and radioactive isotopes. The label can be directly detectable (e.g., optically detectable) or indirectly detectable (for example, via interaction with one or more additional molecules that are in turn detectable). Exemplary labels in the context of the probes disclosed herein are described below. Methods for labeling nucleic acids, and guidance in the choice of labels useful for various purposes, are discussed, e.g., in Sambrook and Russell, in *Molecular Cloning: A Laboratory Manual*, $3^{rd}$ Ed., Cold Spring Harbor Laboratory Press (2001) and Ausubel et al., in *Current Protocols in Molecular Biology*, Greene Publishing Associates and Wiley-Intersciences (1987, and including updates).

Hybridization: The ability of complementary single-stranded DNA, RNA, or DNA/RNA hybrids to form a duplex molecule (also referred to as a hybridization complex). Nucleic acid hybridization techniques can be used to form hybridization complexes between a nucleic acid probe, and the gene it is designed to target.

"Specifically hybridizable" and "specifically complementary" are terms that indicate a sufficient degree of complementarity such that stable and specific binding occurs between a first nucleic acid molecule (or its analog) and a second nucleic acid molecule (such as a nucleic acid target, for example, a DNA or RNA target). The first and second nucleic acid molecules need not be 100% complementary to be specifically hybridizable. Specific hybridization is also referred to herein as "specific binding."

Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, N.Y. (chapters 9 and 11).

Nuclease: An enzyme that cleaves a phosphodiester bond. An endonuclease is an enzyme that cleaves an internal phosphodiester bond in a nucleotide chain (in contrast to exonucleases, which cleave a phosphodiester bond at the end of a nucleotide chain). Endonucleases include restriction endonucleases or other site-specific endonucleases (which cleave DNA at sequence specific sites), DNase I, Bal 31 nuclease, S1 nuclease, Mung bean nuclease, Ribonuclease A, Ribonuclease T1, RNase I, RNase PhyM, RNase U2, RNase CLB, micrococcal nuclease, and apurinic/apyrimidinic endonucleases. Exonucleases include exonuclease III and exonuclease VII. In particular examples, a nuclease is specific for single-stranded nucleic acids, such as S1 nuclease, Mung bean nuclease, Ribonuclease A, or Ribonuclease T1.

Nucleic acid: A deoxyribonucleotide or ribonucleotide polymer in either single or double stranded form, and unless otherwise limited, encompassing analogs of natural nucleotides that hybridize to nucleic acids in a manner similar to naturally occurring nucleotides. The term "nucleotide" includes, but is not limited to, a monomer that includes a base (such as a pyrimidine, purine or synthetic analogs thereof) linked to a sugar (such as ribose, deoxyribose or synthetic analogs thereof), or a base linked to an amino acid, as in a peptide nucleic acid (PNA). A nucleotide is one monomer in a polynucleotide. A nucleotide sequence refers to the sequence of bases in a polynucleotide.

A target nucleic acid (such as a target DNA or RNA) is a nucleic acid molecule whose detection, amount, or sequence is intended to be determined (for example in a quantitative or qualitative manner). In one example, the target is a defined region or particular portion of a nucleic acid molecule, for example a DNA or RNA of interest. In an example where the target nucleic acid sequence is a target DNA or a target RNA, such a target can be defined by its specific sequence or function; by its gene or protein name; or by any other means that uniquely identifies it from among other nucleic acids.

In some examples, alterations of a target nucleic acid sequence (e.g., a DNA or RNA) are "associated with" a disease or condition. That is, detection of the target nucleic acid sequence can be used to infer the status of a sample with respect to the disease or condition. For example, the target nucleic acid sequence can exist in two (or more) distinguishable forms, such that a first form correlates with absence of a disease or condition and a second (or different) form correlates with the presence of the disease or condition. The two different forms can be qualitatively distinguishable, such as by nucleotide polymorphisms or mutation, and/or the two different forms can be quantitatively distinguishable, such as by the number of copies of the target nucleic acid sequence that are present in a sample.

Nucleotide: The fundamental unit of nucleic acid molecules. A nucleotide includes a nitrogen-containing base attached to a pentose monosaccharide with one, two, or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al. (herein incorporated by reference). Includes nucleotides containing other modifications, such as found in locked nucleic acids (LNAs). Thus, the NPPFs, primers, CFSs, bifunctional linkers, and anchors disclosed herein can include natural and unnatural bases.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, and 2,6-diaminopurine.

Examples of modified sugar moieties which may be used to modify nucleotides at any position on its structure include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Primer. A short nucleic acid molecule, such as a DNA oligonucleotide 9 nucleotides or more in length, which in some examples is used to initiate the synthesis of a longer nucleic acid sequence. Longer primers can be about 10, 12, 15, 20, 25, 30 or 50 nucleotides or more in length. Primers can be annealed to a complementary nucleic acid strand by nucleic acid hybridization to form a hybrid between the primer and the complement strand, and then the primer extended along the complement strand by a polymerase enzyme. Primer pairs can be used for amplification of a nucleic acid sequence, for example by PCR or other nucleic-acid amplification methods.

In one example, a primer includes a label, which can be referred to as a probe.

Probe: A nucleic acid molecule capable of hybridizing with a target nucleic acid molecule (e.g., a target DNA or RNA) and, when hybridized to the target, is capable of being detected either directly or indirectly. Thus probes permit the detection, and in some examples quantification, of a target nucleic acid molecule, such as a DNA or RNA. In some examples, a probe includes a detectable label.

Nuclease protection probe (NPP): A nucleic acid molecule having a sequence that is complementary to a target DNA or RNA and is capable of hybridizing to the target DNA or RNA. The NPP protects the complementary target DNA or RNA nucleic acid molecule from cleavage by a nuclease, such as a nuclease specific for single-stranded nucleic acids. A nuclease protection probe comprising a flanking sequence (NPPF) is an NPP that further includes one or more flanking sequences at the 5'-end, 3'-end, or both, wherein the flanking sequence includes a sequence of contiguous nucleotides not found in a nucleic acid molecule present in the sample, and which can provide a universal amplification sequence point that can be used as an attachment point for an amplification primer. In one example the flanking sequence is used to capture the NPPF to a substrate, wherein a nucleic acid capture sequence on the substrate and at least a portion of the flanking sequence are complementary to one another, thereby permitting capture of the NPPF onto the substrate.

Sample: A biological specimen containing DNA (for example, genomic DNA or cDNA), RNA (including mRNA or miRNA), protein, or combinations thereof, obtained from a subject (such as a human or other mammalian subject). Examples include, but are not limited to cells, cell lysates, chromosomal preparations, peripheral blood or fractions thereof, urine, saliva, tissue biopsy (such as a tumor biopsy or lymph node biopsy), surgical specimen, bone marrow, amniocentesis samples, fine needle aspirates, circulating tumor cells, and autopsy material. In one example, a sample includes RNA or DNA. In particular examples, samples are used directly (e.g., fresh or frozen), or can be manipulated prior to use, for example, by fixation (e.g., using formalin) and/or embedding in wax (such as FFPE tissue samples).

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *Comput. Appl. Biosci.* 5:151-3, 1989; Corpet et al., *Nucl. Acids Res.* 16:10881-90, 1988; Huang et al. *Comput. Appl. Biosci.* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

One indication that two nucleic acid molecules are closely related is that the two molecules hybridize to each other under stringent conditions. Stringent conditions are sequence-dependent and are different under different environmental parameters. The nucleic acid probes disclosed herein are not limited to the exact sequences shown, as those skilled in the art will appreciate that changes can be made to a sequence, and not substantially affect the ability of a probe to function as desired. For example, sequences having at least 80%, at least 85%, at least 90%, at least 91%, at least 92%, at least 93%, at least 94%, at least 95%, at least 96%, at least 97%, at least 98%, or at least 99%, such as 100% sequence identity to the disclosed probes are provided herein (e.g., SEQ ID NOS: 1-16). One of skill in the art will appreciate that these sequence identity ranges are provided for guidance only; it is possible that probes can be used that fall outside these ranges.

Sequencing: To determine the primary structure (or primary sequence) of an unbranched biopolymer. Sequencing results in a symbolic linear depiction known as a sequence which succinctly summarizes much of the atomic-level structure of the sequenced molecule, for example, a polynucleotide. When the molecule is a polynucleotide, such as, for example, RNA or DNA, sequencing can be used to obtain information about the molecule at the nucleotide level, which can then be used in deciphering various secondary information about the molecule itself and/or the polypeptide encoded thereby. DNA sequencing is the process of determining the nucleotide order of a given DNA molecule and RNA sequencing is the process of determining the nucleotide order of a given RNA molecule. In some examples, sequencing of a nucleic acid molecule is done indirectly, for example by determining the sequence of at least a portion of a nuclease protection probe comprising a flanking sequence (NPPF), which bound to the target nucleic acid molecule.

Simultaneous: Occurring at the same time or substantially the same time and/or occurring in the same sample or the same reaction (for example, contemporaneous). In some examples, the events occur within 1 microsecond to 120 seconds of one another (for example within 0.5 to 120 seconds, 1 to 60 seconds, or 1 to 30 seconds, or 1 to 10 seconds).

Subject: Any multi-cellular vertebrate organism, such as human and non-human mammals (e.g., veterinary subjects). In one example, a subject is known or suspected of having a tumor or an infection.

Surface (or substrate): Any solid support or material which is insoluble, or can be made insoluble by a subsequent reaction. Numerous and varied solid supports are known to those in the art and include, without limitation, nitrocellulose, the walls of wells of a reaction tray, multi-well plates, test tubes, polystyrene beads, magnetic beads, membranes, and microparticles (such as latex particles). Any suitable porous material with sufficient porosity to allow access by detector reagents and a suitable surface affinity to immobilize capture reagents (e.g., oligonucleotides) is contemplated by this term. For example, the porous structure of nitrocellulose has excellent absorption and adsorption qualities for a wide variety of reagents, for instance, capture reagents. Nylon possesses similar characteristics and is also suitable. Microporous structures are useful, as are materials with gel structure in the hydrated state.

Further examples of useful solid supports include natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

All publications, patent applications, patents, and other references mentioned herein are incorporated by reference in their entirety for all purposes. All sequences associated with the GenBank Accession Nos. mentioned herein are incorporated by reference in their entirety as were present on Dec. 15, 2011, to the extent permissible by applicable rules and/or law. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

III. Methods of Detecting or Sequencing Nucleic Acid Molecules

Disclosed herein are methods of detecting and/or sequencing nucleic acid molecules present in a sample. In some examples, at least two different nucleic acid molecules are detected in the same sample or same assay (for example, in the same well of an assay plate or array). In some examples, the same nucleic acid molecule or molecules is detected in at least two different samples or assays (for example, in samples from different patients).

The disclosed methods provide improvements to a quantitative nuclease protection assay (qNPA), for example as described in International Patent Publications WO 99/032663; WO 00/037683; WO 00/037684; WO 00/079008; WO 03/002750; and WO 08/121927; and U.S. Pat. Nos. 6,232,066, 6,238,869; 6,458,533; and 7,659,063, all of which are incorporated herein by reference in their entirety. See also, Martel et al., *Assay and Drug Development Technologies.* 2002, 1 (1-1):61-71; Martel et al., *Progress in Biomedical Optics and Imaging,* 2002, 3:35-43; Martel et al., *Gene Cloning and Expression Technologies*, Q. Lu and M. Weiner, Eds., Eaton Publishing, Natick (2002); Seligmann *PharmacoGenomics*, 2003, 3:36-43; Martel et al., "Array Formats" in "Microarray Technologies and Applications," U. R. Muller and D. Nicolau, Eds, Springer-Verlag, Heidelberg (2005); Sawada et al., *Toxicology in Vitro,* 20:1506-1513, 2006; Bakir, et al., *Bioorg. & Med. Chem Lett,* 17:3473-3479, 2007; Kris et al., *Plant Physiol.* 144:1256-1266, 2007; Roberts et al., *Laboratory Investigation,* 87:979-997, 2007; Rimsza et al., *Blood,* 2008 Oct. 15, 112 (8):3425-3433; Pechhold et al., *Nature Biotechnology,* 27:1038-1042, 2009. For example, the disclosed qNPA methods have enhanced sensitivity as compared to prior qNPA methods, such as an increase in detectable signal of at least 10-fold, at least 25-fold, at least 100-fold, at least 125-fold, at least 150-fold, at least 170-fold, or at least 200-fold. That is, at least 10-fold, or even as much as 200-fold less sample is required, or conversely, rare genes that were 10-times below the sensitivity, or even up to 20-times below the sensitivity of currently available methods are detectable with the disclosed methods. Consequently, sample types such as fine needle aspirates which provide very small amounts of FFPE, or circulating tumor cells, where as few as 10, 50, or 100 cells may be recovered from a patient, can be tested and rare genes detected using the disclosed methods.

In addition, the disclosed methods provide improvements to a quantitative nuclease protection sequencing (qNPS) method, for example as described in US Patent Publication No. US-2011-0104693. qNPS is a sequencing method that uses a qNPA to convert target nucleic acid molecules present in a sample, even when cross linked, into stable single-stranded nucleic acid targets (nuclease protection probes, NPPs) that can be recovered in solution without capture or separation, by use of the nuclease protection step and (as necessary) treatment with base to dissociate the nuclease protection probes from protecting target molecules, and in the case of RNA, hydrolyze the RNA target. The amounts of the NPPs remaining after nuclease hydrolysis are then determined by sequencing which can include sequencing of the probes themselves. The improved methods disclosed herein use a variation of a NPP, a nuclease protection probe comprising a flanking sequence (NPPF). The use of NPPF permits multiplexing, as well as conserving the stoichiometry of the detected or sequenced target nucleic acid molecule, because the flanking sequences on the probe permit universal primer binding sites for amplification. As the primer binding sites are universal, the same primers can be used to amplify any NPPF for any target sequence, thus allowing for multiplexing and conservation of stoichiometry. In one example, amplifying from flanking sequences on both ends of the NPPF provides an unexpected and greater specificity than prior qNPA and qNPS methods. NPPFs with intact 3'- and 5'-flanking sequences will be amplified exponentially; nuclease-cleaved NPPFs will not be amplified sufficiently to be sequenced or detected. In contrast, NPPs processed using prior qNPA methods can be partially cleaved at either the end of the sequence that is involved in capture onto the array or at the end of the sequence that is involved in detection on the array, or at both due to weak or incorrect hybridization to incorrect target nucleic acids, and yet still be captured and detected, leading to a loss of specificity for the correct target nucleic acid. This does not occur with the disclosed NPPF probes. The disclosed methods conserve the original nucleic acid molecule stoichiometry such that the detected or sequenced nucleic acid molecules retain the same relative quantities of the nucleic acid molecules as in the test sample, such as a variation of no more than 20%, no more than 15%, no more than 10%, no more than 9%, no more than 8%, no more than 7%, no more than 6%, no more than 5%, no more than 4%, no more than 3%, no more than 2%, no more than 1%, no more than 0.5%, or no more than 0.1%, such as 0.001%-5%, 0.01%-5%, 0.1%-5%, or 0.1%-1%.

The disclosed methods also permit multiplexing experiments, such as multiple reactions within the same assay (such as multiple samples from different patients in the same reaction well), and multiple reactions analyzed within the same run/channel of the sequencer.

Specifically, in contrast to prior qNPA and qNPS methods, the disclosed methods use modified nucleic acid protection probes (NPPs), which include flanking sequences on one or both ends of the NPPs. These modified NPPs with 5'-end and/or 3'-end flanking sequences are referred to herein as nucleic acid protection probes with flaking sequences (NP-PFs). The presence of the one or both flanking sequences, which serve as universal primer points for hybridization and/or amplification (and can be used for other purposes including capture or tagging of NPPFs), conserve the original nucleic acid stoichiometry in the sample as the flanking sequences are part of the NPPF. In addition, this eliminates the need for ligation to add priming sites, tags, and the like to the NPPFs, which can incorporate artifacts which skew the nucleic acid stoichiometry in the sample, and provide an additional source of variability. Eliminating the need for ligation eliminates both potential artifact skewing stoichiometry and degrading reproducibility.

FIG. 1 is a schematic diagram showing an exemplary NPPF. The nuclease protection probe having at least one flanking sequence (NPPF) 100 includes a region 102 that includes a sequence that specifically binds to the target nucleic acid sequence (and can also specifically binds to a bifunctional linker). The target nucleic acid sequence can be DNA (e.g., genomic DNA or cDNA) or RNA (such as mRNA, miRNA, tRNA, siRNA), or both. The NPPF includes one or more flanking sequences 104 and 106. FIG. 1 shows an NPPF 100 with both a 5'-flanking sequence 104 and a 3'-flanking sequence 106. However, NPPFs can in some examples have only one flanking sequence.

FIG. 2 is a schematic diagram showing the initial steps of an exemplary method of using the NPPFs to detect or sequence a nucleic acid molecule using the disclosed methods. As shown in step 1, a sample (such as one known or suspected of containing a target nucleic acid, 200) that has been treated with a sample disruption buffer (e.g., lysed or otherwise treated to make nucleic acids accessible) is contacted or incubated with a plurality of nuclease protection probes having one or more flanking sequences (NPPFs) 202 including at least one NPPF which specifically binds to a first target nucleic acid (such as a target DNA or RNA). The reaction can also include other NPPFs which specifically bind to a second target nucleic acid, and so on. For example, the method can use one or more different NPPFs designed to be specific for each unique target nucleic acid molecule. Thus, the measurement of 100 genes requires the use of at least 100 different NPPFs, with at least one NPPF specific per gene (such as several different NPPFs/gene). Thus, for example, the method can use at least 2 different NPPFs, at least 3, at least 4, at least 5, at least 10, at least 25, at least 50, at least 75, at least 100 or even at least 200 different NPPFs (such as 2 to 500, 2 to 100, 5 to 10, 2 to 10, or 2 to 20 different NPPFs). However, one will appreciate that in some examples, the plurality of NPPFs can include more than one (such as 2, 3, 4, 5, 10, 20, 50 or more) NPPFs specific for a single target nucleic acid molecule. The dashed bars in FIG. 2 represent an NPPF specific for a first target and the solid gray bars represent an NPPF specific for second target. In some examples, the NPPFs include a detectable label, such as biotin (B), but one skilled in the art will appreciate that a label can be added at other steps, such as during amplification. Thus, the biotin shown in FIG. 2 is optional, and other labels can be used. The reaction also includes nucleic acid molecules that are complementary to the flanking sequences (CFS), 204, that are specific for the flanking sequences of the NPPF 202. FIG. 2 shows the dotted green bars 204 as the CFSs specific for a flanking sequence(s) of the NPP. One skilled in the art will appreciate that the sequence of the CFSs will vary depending on the flanking sequence present. In addition, more than one CFS can be used to ensure a flanking region is protected (e.g., at least two CFSs can use that bind to different regions of a single flanking sequence). The CFS can include natural or unnatural bases. Although FIG. 2 shows NPPFs with flanking sequences on both ends of the NPPF; one skilled in the art will appreciate that a single flanking sequence can be used. The sample, NPPFs and CFSs are incubated under conditions sufficient for NPPFs to specifically bind to their respective target nucleic acid molecule, and for CFSs to bind to its their complementary sequence on the NPPF flanking sequence. In some examples, the CFSs 204 are added in excess of the NPPFs 202, for example at least 5-fold more CFSs than NPPFs (molar excess), such as at least 6-fold, at least 7-fold, at least 8-fold, at least 9-fold, at least 10-fold, at least 20-fold, at least 40-fold, at least 50-fold, or at least 100-fold more CFSs than the NPPFs. In some examples, the NPPFs 202 are added in excess of the total nucleic acid molecules in the sample, for example at least 50-fold more NPPF than total nucleic acid molecules in the sample (molar excess), such as at least 75-fold, at least 100-fold, at least 200-fold, at least 500-fold, or at least 1000-fold more NPPF than the total nucleic acid molecules in the sample. For experimental convenience a similar concentration of each NPPF can be included to make a cocktail, such that for the most abundant nucleic acid target measured there will be at least 50-fold more NPPF for that nucleic acid target, such as an at least 100-fold excess. The actual excess and total amount of all NPPFs used is limited only by the capacity of the nuclease (e.g., S1 nuclease) to destroy all NPPF's that are not hybridized to target nucleic acid targets. In some examples the reaction is heated, for example incubated for overnight at 50° C.

As shown in step 2 in FIG. 2, after allowing the binding/hybridization reactions to occur, the sample is contacted with a nuclease specific for single-stranded (ss) nucleic acid molecules under conditions sufficient to remove (or digest) ss nucleic acid molecules, such as unbound nucleic acid molecules (such as unbound NPPFs, CFSs, and target nucleic acid molecules, or portions of such molecules that remain single stranded). As shown in FIG. 2, incubation of the sample with a nuclease specific for ss nucleic acid molecules results in degradation of any ss nucleic acid molecules, leaving intact double-stranded nucleic acid molecules, including NPPFs that have bound thereto and CFSs and target nucleic acid molecule. For example, the reaction can be incubated at 50° C. for 1.5 hours with S1 nuclease (though hydrolysis can occur at other temperatures and be carried out for other periods of time, and in part that the time and temperature required will be a function of the amount of nuclease, and on the amount of nucleic acid required to be hydrolyzed, as well as the Tm of the double-stranded region being protected).

After this reaction, the samples can optionally be treated to otherwise remove or separate non-hybridized material and/or to inactivate or remove residual enzymes (e.g., by heat, phenol extraction, precipitation, column filtration, etc.). For example, as shown in step 3 the pH of the reaction can be increased to inactivate the nuclease, and the reaction heated to destroy the nuclease. In addition, heating the reaction will also dissociate the target nucleic acid (such as target DNA or target RNA) and the CFSs from the complementary regions on the NPPF. This leaves behind the intact NPPFs that previously bound the target nucleic acid molecules and CFSs, wherein the intact NPPFs are in direct proportion to how much NPPF had been hybridized to the target. In some examples, the hybridized target nucleic acid and CFSs can be degraded, e.g., by nucleases or by chemical treatments. Alternatively, the sample can be treated so as to leave the (single strand) hybridized portion of the target nucleic acid molecules, or the duplex formed by the hybridized target nucleic acid molecules and CPSs to the NPPF, to be further analyzed (for example the target hybridized to the NPPF can be sequenced). In one example, the pH increased to about pH 8, and the reaction is incubated at 95° C. for 10 minutes and the causing the target nucleic acid and the CFSs to dissociate (and if the target nucleic acid is RNA, hydrolyzing said target nucleic acids).

As shown in step 4 in FIG. 2, either after step 2 or step 3, the NPPFs are amplified, for example using PCR. FIG. 2 shows the PCR primers or probes 208 as arrows. The PCR primers or probes can include a label, such as biotin, thereby resulting in the production of amplicons that are labeled. At least a portion of the PCR primers/probes 208 are specific for the flanking sequences of the NPPFs 202. The resulting amplicons 210 can then be detected, for example by binding to an array (see FIG. 3) or sequenced (see FIG. 4). In some examples, the concentration of the primers 208 are in excess of the CPSs 204, for example in excess by at least 10,000-fold, at least 50,000-fold, at least 100,000-fold, at least 150,000-fold, at least 200,000-fold, or at least 400,000-fold. In some examples, the concentration of primers 208 in the reaction is at least 200 nM (such as at least 400 nM, at least 500 nM, or at least 1000 nM), and the concentration of CPSs 204 in the reaction is less than 1 pM, is less than 0.5 pM, or is less than 0.1 pM.

As shown in step 5 in FIG. 3, the amplicons 210, which are the amplified NPPFs, can be contacted with a surface 212 including multiple spatially discrete regions. Two different versions are shown. In one example (top), the surface includes at least one anchor 214 in association with a bifunctional linker 216. In some examples the amplicons 210 are added to a 2× buffer prior to contact with the surface 212. The bifunctional linker 216 includes a first portion which specifically binds to the anchor and a second portion which specifically binds to one of the plurality of NPPF amplicons 210. The amplicons 210 are incubated with the surface 212 under conditions sufficient for each of the plurality of NPPF amplicons 210 to specifically bind to the second portion of a bifunctional linker 216. As shown in FIG. 1, the region of the NPPF 102 that specifically binds to a bifunctional linker is complementary in sequence to the bifunctional linker (and is also complementary to the target nucleic acid sequence). The NPPF amplicons 210 bound to the second portion of the bifunctional linker 216 are detected utilizing the detectable label included in the NPPF amplicons 210, thereby detecting the target nucleic acid in the sample.

In other example (bottom), the surface includes at least one nucleic acid capture molecule 220, which can be directly attached to the surface through a covalent bond. In some examples the amplicons 210 are added to a 2× buffer prior to contact with the surface 212. The nucleic acid capture molecule 220 includes a sequence that is complementary to a least a portion of one of the plurality of NPPF amplicons 210, such as at least a portion of a flanking sequence region of the NPPF (or a region added to the flanking sequence during amplification for example). The amplicons 210 are incubated with the surface 212 under conditions sufficient for each of the plurality of NPPF amplicons 210 to specifically bind to the nucleic acid capture molecule 220.

The NPPF amplicons 210 bound to the nucleic acid capture molecule 220 are detected utilizing the detectable label included in the NPPF amplicons 210, thereby detecting the target nucleic acid in the sample. For example, the NPPF amplicons can be incubated with the surface overnight at 50° C. to allow binding of the NPPF amplicons to the nucleic acid capture molecule 220. In one example, the NPPF amplicons are labeled with biotin. As shown in step 6 of FIG. 3, the biotin can be detected using avidin-HRP 218 (for example incubating with the avidin-HRP for 1 hour at 37° C.). As shown in step 7 of FIG. 3, excess unbound avidin-HRP 218 is removed, an appropriate substrate is added, and the surface imaged to detect the bound NPPFs. Although biotin is shown as an example, one skilled in the art will appreciate that other detection methods can be used, for example by detecting a fluorophore or antibody on the NPPF amplicons.

In some examples, if the NPPF amplicons 210 are not labeled (for example no label is added during amplification in step 4 of FIG. 2), the NPPF amplicons 210 can include a region (such as the flanking sequence or portion thereof) that is complementary to the sequence of a labeled probe (wherein this region is not complementary to the bifunctional linker 216). This complementary probe can then be hybridized to the NPPF amplicons 210 prior to attaching them to a substrate as shown in step 5 of FIG. 3.

In some examples, the NPPF amplicons are contacted with a plurality of surfaces (such as a population of beads or other particles). In one example, each surface (such as each bead or sub-population of beads within a mixed bead population) includes at least one anchor in association with a bifunctional linker including a first portion which specifically binds to the anchor and a second portion which specifically binds to one of the plurality of NPPF amplicons, under conditions sufficient for each of the plurality of NPPF amplicons to specifically bind to the second portion of a bifunctional linker. The NPPF amplicons bound to the second portion of the bifunctional linker can be detected utilizing the detectable label that is associated with the NPPF amplicons, thereby detecting the target nucleic acid molecule in the sample. In another example, each surface (such as each bead or sub-population of beads within a mixed bead population) includes at least one nucleic acid capture molecule having a sequence complementary to a least a portion of the NPPF amplicons (such as a flanking sequence or portion thereof), under conditions sufficient for each of the plurality of NPPF amplicons to specifically bind to the nucleic acid capture molecule. The NPPF amplicons bound to the nucleic acid capture molecule can be detected utilizing the detectable label that is associated with the NPPF amplicons, thereby detecting the target nucleic acid molecule in the sample.

As shown in step 5 in FIG. 4, the amplicons 210, which are the amplified NPPFs, can be sequenced. For example, one or both of the flanking sequences of the amplified NPPFs can include (or have added thereto) a sequence adapter, or a primer that is complementary to and is hybridized to the flanking sequence, can include a sequence adapter sequence, which is complementary to capture sequences on the sequencing chip, and permits sequencing of the NPPF using a particular sequencing platform. In some examples, a plurality of NPPFs are sequenced in parallel, for example simultaneously or contemporaneously. This method can thus be used to sequence a plurality of NPPF sequences.

FIGS. 5A and 5B are schematic diagrams providing a further a summary of the method, with more details of the nucleic acid molecules. As shown in the left panel of FIG. 5A, target nucleic acids 400 in a sample (such as a sample that has been treated with a sample disruption buffer) is contacted or incubated with a plurality of nuclease protection probes having one or more flanking sequences (NPPFs) 402 (wherein each NPPF is specific for a particular target nucleic acid 400), and with nucleic acid molecules that are complementary to the flanking sequences (CFS) 406, that are specific for the flanking sequences 404 on the ends of the NPPFs. Three different target nucleic acids 400 are shown: one copy of target 1 (green) two copies of target 2 (red), and three copies of target 3 (blue). This example shows equal amounts of each NPPF 402 are added. Although FIG. 5A shows NPPFs with flanking sequences on both ends of the NPP; one skilled in the art will appreciate that a single flanking sequence can be used. The middle panel of FIG. 5A shows the reaction products after allowing the binding/hybridization reactions to occur between the target nucleic acids 400, NPPFs 402, and CFSs 406. The target nucleic acids 400 hybridize to a central region of the NPPFs, and the CFSs 406 hybridize to the 3'- and 5'-flanking sequences 404. The right panel of FIG. 5A shows the reaction products after the sample is contacted with a nuclease specific for single-stranded (ss) nucleic acid molecules under conditions sufficient to remove (or digest) ss nucleic acid molecules. As shown, regions of the target nucleic acids that did not hybridize to an NPPF 408 are digested away, as are ss regions of NPPFs that did not bind to a target nucleic acid or a CFS (e.g., 410). This leaves intact double-stranded nucleic acid molecules, including NPPFs that have bound thereto and CFSs and target nucleic acid molecule (e.g., 412) and well as regions of the NPPF that hybridized to target only (but not CFS), or that hybridized to CFS only (but not target) (e.g., 414).

The left panel of FIG. 5B shows the reaction products after separating the double-stranded nucleic acid molecules (for example using heat and increasing the pH). The resulting NPPFs that survive, which are in direct proportion to the target nucleic acid molecules that protected them during the nuclease step, can then be amplified. The middle panel of FIG. 5B shows the reaction products after they are amplified. The right panel of FIG. 5B shows that after amplification, the resulting NPPF amplicons can be detected or sequenced (e.g., see FIGS. 2-4).

In some embodiments, the methods can include contacting a sample from a subject (such as a sample including nucleic acids, such as DNAs or RNAs) with plurality of NPPFs including at least one NPPF which specifically binds to a first target (such as a first RNA) and optionally at least one NPPF which specifically binds to a second target (such as a second RNA). In some examples, the plurality of NPPFs includes more than one (such as 2, 3, 4, 5, or more) NPPFs specific for a single target nucleic acid molecule. For example, the plurality of NPPFs can include at least one NPPF (such as at least 1, 2, 3, 4, 5, 10, 15, 20, 25, 50, 75, 100, 200, 300, 500, 1000, 2000, 3000, or more), wherein each NPPF specifically binds to a single target nucleic acid molecule. In another or additional example, the plurality of NPPFs include at least two different NPPF populations (such as 2, 3, 4, 5, 10, 20, or 50 different NPPF sequences), wherein each NPPF population (or sequence) specifically binds to a different target nucleic acid molecule.

In some examples, several NPPFs hybridize to different portions of the same target nucleic acid, and the number of NPPFs hybridizing to different portions of each target nucleic acid can be the same or different. For example, a low expressed nucleic acid target may have more NPPFs that hybridize to it relative to a nucleic acid target expressed at a higher level, such as four NPPFs hybridizing to a low expressed nucleic acid target and a single NPPF hybridizing to a high expressed nucleic acid target. In some examples, some of the NPPFs specific for some target nucleic acids may not have flanking sequences (e.g., NPPs), and thus may not be amplified, or labeled, or have the appropriate adapters attached, and thus this portion of NPPFs will not be detected or sequenced. Using such a mixture, which can be about 1 to 5, or about 1 to 10, or about 1 to 100, or about 1 to 1,000 NPPFs with flanking sequence to NPPs without flanking sequence, the signal measured, or the number of NPPFs sequenced, can be "attenuated", such that if there are 10,000 copies of target nucleic acid, and a ratio of 1 to 5 is used, then after amplification only $\frac{1}{5}^{th}$ the number of NPPFs will be sequenced as would have been sequenced had every NPPF contained flanking sequences.

In some examples, the plurality of NPPFs include at least 2, at least 5, at least 10, at least 20, at least 100 or at least 1000 (such as 2 to 5000, 2 to 3000, 10 to 1000, 50 to 500, 25 to 300, 50 to 300, 10 to 100, or 50 to 100) unique NPPF sequences. The plurality of NPPs can include any combination of NPPFs specific for one or more target nucleic acid molecules The plurality of NPPFs, along with the CFSs, are incubated with the sample under conditions sufficient for the NPPFs to specifically hybridize to their respective target nucleic acids and their respective CFSs. In some examples, the CFSs are added in excess of the NPPFs, such as an at least 2-fold, at least 3-fold, at least 4-fold, at least 5-fold or at least 10-fold molar excess of CFS to NPPF. In some examples, the NPPFs are added in excess of the nucleic acid molecules in the sample, such as an at least 10-fold, at least 50-fold, at least 75-fold, at least 100-fold, at least 250-fold, at least 1,000 fold, at least 10,000 fold, or at least 100,000 fold molar excess or more of NPPF to nucleic acid molecules in the sample. It will be appreciated that if the NPPF for a highly abundant nucleic acid target is in excess of 1,000 fold, and the same concentration of each different NPPF is the same, then the excess of NPPF for a low abundant gene can be many times greater, such as 1,000 times greater for a gene that is 1,000 fold lower abundance than the high abundant nucleic acid target.

The hybridized sample can then be contacted with a nuclease specific for single-stranded nucleic acids (for example, S1 nuclease). The resulting NPPFs that survive, which are in direct proportion to the target nucleic acid molecules that protected them during the nuclease step, can then be amplified. For example, amplification primers that include a sequence complementary to the flanking sequence of the NPPF can be used. The resulting NPPF amplicons can then be detected by methods known in the art, for example by binding them to an array or other substrate, or sequenced. The target nucleic acid molecule(s) are identified as present in the sample when their respective NPPF is detected or sequenced.

A. Exemplary Hybridization Conditions

Disclosed herein are conditions sufficient for a plurality of NPPFs to specifically hybridize to target nucleic acid molecule(s), such as DNAs and RNAs present in a sample from a subject, as well as specifically hybridize to CFS complementary to the flanking sequence(s). For example, the features (such as length, base composition, and degree of complementarity) that will enable a nucleic acid (e.g., an NPPF) to hybridize to another nucleic acid (e.g., a target DNA or target RNA or CFS) under conditions of selected stringency, while minimizing non-specific hybridization to other substances or molecules can be determined based on the present disclosure. Characteristics of the NPPFs are discussed in more detail in Section IV, below. Typically, a region of an NPPF will have a nucleic acid sequence (e.g., FIG. 1, 102) that is of sufficient complementarity to its corresponding target nucleic acid molecule to enable it to hybridize under selected stringent hybridization conditions, as well as a region (e.g., FIG. 1, 104, 106) that is of sufficient complementarity to its corresponding CFS to enable it to hybridize under selected stringent hybridization conditions. Exemplary hybridization conditions include hybridization at about 37° C. or higher (such as about 37° C., 42° C., 50° C., 55° C., 60° C., 65° C., 70° C., 75° C., or higher). Among the hybridization reaction parameters which can be varied are salt concentration, buffer, pH, temperature, time of incubation, amount and type of denaturant such as formamide. For example, nucleic acid (e.g., a plurality of NPPFs) can be added to a sample at a concentration ranging from about 10 pM to about 10 nM (such as about 30 pM to 5 nM, about 100 pM to about 1 nM), in a buffer (such as one containing NaCl, KCl, $H_2PO_4$, EDTA, 0.05% Triton X-100, or combinations thereof) such as a lysis buffer.

In one example, each NPPF is added to the sample at a final concentration of at least 10 pM, such as at least 20 pM, at least 30 pM, at least 50 pM, at least 100 pM, at least 150 pM, at least 200 pM, at least 500 pM, at least 1 nM, or at least 10 nM. In one example, each NPPF is added to the sample at a final concentration of about 30 pM. In another example, each NPPF is added to the sample at a final concentration of about 167 pM. In a further example, each NPPF is added to the sample at a final concentration of about 1 nM. In one example, each CFS is added to the sample at a final concentration of about at least 6-times the amount of probe, such as at least 10-times or at least 20-times the amount of probe (such as 6 to 20 times the amount of probe). In one example, each CFS is added at least 1 nM, at least 5 nM, at least 10 nM, at least 50 nM, at least 100 nM, or at least 200 nm, such as 1 to 100, 5 to 100 or 5 to 50 nM. For example if there are six probes, each at 166 pM, each CFSs can be added at 5 to 50 nM.

The nucleic acids in the sample are denatured, rendering them single stranded and available for hybridization (for example at about 95° C. to about 105° C. for about 5-15 minutes). By using different denaturation solutions, this denaturation temperature can be modified, so long as the combination of temperature and buffer composition leads to formation of single stranded target DNA or RNA or both. The nucleic acids in the sample and the CFSs are then hybridized to the plurality of NPPFs for between about 10 minutes and about 72 hours (for example, at least about 1 hour to 48 hours, about 6 hours to 24 hours, about 12 hours to 18 hours, or overnight) at a temperature ranging from about 4° C. to about 70° C. (for example, about 37° C. to about 65° C., about 42° C. to about 60° C., or about 50° C. to about 60° C.). Of course the hybridization conditions will vary depending on the particular NPPFs and CFSs used, but are set to ensure hybridization of NPPFs to the target molecules and the CFSs. In some examples, the plurality of NPPFs and CFSs are incubated with the sample at a temperature of at least about 37° C., at least about 40° C., at least about 45° C., at least about 50° C., at least about 55° C., at least about 60° C., at least about 65° C., or at least about 70° C. In one example, the plurality of NPPFs and CFSs are incubated with the sample at about 37° C., at about 42° C., or at about 50° C.

In some embodiments, the methods do not include nucleic acid purification (for example, nucleic acid purification is not performed prior to contacting the sample with the NPPFs and/or nucleic acid purification is not performed following contacting the sample with the NPPFs). In some examples, no pre-processing of the sample is required except for cell lysis. In some examples, cell lysis and contacting the sample with the plurality of NPPFs and CFSs occur sequentially. In other examples, cell lysis and contacting the sample with the plurality of NPPFs and CFSs occur concurrently, in some non-limiting examples without any intervening steps.

When the NPPFs are subsequently subjected to PCR (e.g., universal amplification or NPPF-specific amplification such as for real time PCR), the buffers and reagents used for lysis, hybridization of NPPFs to their target nucleic acids, nuclease digestion, and base hydrolysis can be compatible with the polymerase used for amplification.

B. Treatment with Nuclease

Following hybridization of the NPPFs to target nucleic acids in the sample and to CFSs, the sample is subjected to a nuclease protection procedure. NPPFs which have hybridized to a target nucleic acid molecule and (when used) CFS (one or two CFSs, depending if there are both 5'- and 3'-flanking sequence on the NPPF or just one, or no CFS where flanking sequences are not required for amplification or measurement) are not hydrolyzed by the nuclease and can be subsequently amplified, and then detected or sequenced (or both).

Treatment with one or more nucleases will destroy all ss nucleic acid molecules (including RNA and DNA in the sample that is not hybridized to (thus not protected by) NPPFs, NPPFs that are not hybridized to target nucleic acid, and (when used) CFSs not hybridized to an NPPF), but will not destroy ds nucleic acid molecules such as NPPFs which have hybridized to CFSs and a target nucleic acid molecule present in the sample. For example, if the sample includes a cellular extract or lysate, unwanted nucleic acids, such as non-target genomic DNA, tRNA, rRNA, mRNA, miRNA, and portions of the target nucleic acid molecule(s) that are not hybridized to complementary NPPF sequences (such as overhangs), which in the case of mRNA or DNA nucleic acid targets will constitute the majority of the nucleic target sequence, can be substantially destroyed in this step. This leaves behind a stoichiometric amount of target nucleic acid/CFS/NPPF duplex. If the target molecule is cross-linked to tissue that occurs from fixation, the NPPFs hybridize to the cross-linked target molecule without the need to reverse cross-linking, or otherwise release the target nucleic acid from the tissue to which it is cross-linked.

Conditions can be selected such that single nucleotide differences leading to an unpaired base is not cleaved, or a nuclease can be used which just cleaves unpaired bases up to the ends of the hybridized nuclease protection probe, such as an exonuclease. Conditions can also be selected which will hydrolyze the NPPF sequence at the point of a single unpaired base, and similarly hydrolyze the target nucleic acid at that position.

Examples of nucleases include endonucleases, exonuclease, and combinations thereof. Any of a variety of nucleases can be used, including, DNAase, pancreatic RNAse, mung bean nuclease, S1 nuclease, RNAse A, Ribonuclease T1, Exonuclease III, Exonuclease VII, RNAse CLB, RNAse PhyM, RNAse U2, or the like, depending on the nature of the hybridized complexes and of the remainder of nucleic acids and non-target nucleic acid sequences present in the sample. One of skill in the art can select an appropriate nuclease. In a particular example, the nuclease is specific for single-stranded (ss) nucleic acids, for example S1 nuclease. One advantage of using a nuclease specific for ss nucleic acids, in addition to hydrolyzing excess NPPFs and conferring the stoichiometry of target nucleic acid to the NPPFs, is to remove such single-stranded ("sticky") molecules from subsequent reaction steps where they may lead to undesirable background or cross-reactivity. However, one skilled in the art will appreciate that if the target nucleic acid is to be sequenced, this is not necessary, as only the NPPFs with the appropriate sequencing adapters will hybridize to the sequencing chips, at which point the ss molecules from the sample can be washed away. S1 nuclease is commercially available from for example, Promega, Madison, Wis. (cat. no. M5761); Life Technologies/Invitrogen, Carlsbad, Calif. (cat. no. 18001-016); Fermentas, Glen Burnie, Md. (cat. no. EN0321), and others. Reaction conditions for these enzymes are well-known in the art and can be optimized empirically.

In some examples, S1 nuclease diluted in a buffer (such as one containing sodium acetate NaCl, KCl, $ZnSO_4$, KATHON, or combinations thereof) is added to the hybridized probe/sample mixture and incubated at about 37° C. to about 60° C. (such as about 50° C.) for 10-120 minutes (for example, 10-30 minutes, 30 to 60 minutes, 60-90 minutes, or 120 minutes) to digest non-hybridized nucleic acid from the sample and non-hybridized NPPFs.

The samples can optionally be treated to otherwise remove non-hybridized material and/or to inactivate or remove residual enzymes (e.g., by heating, phenol extraction, precipitation, column filtration, addition of proteinase k, addition of a nuclease inhibitor, chelating divalent cations required by the nuclease for activity, or combinations thereof). In some examples, the samples are optionally treated to dissociate the target nucleic acid and the CFS(s) from its complementary NPPF (e.g., using base hydrolysis and heat). In some examples, after hybridization and nuclease treatment, the target RNA molecule hybridized to the NPPF can be degraded, e.g., by dissociating the duplex with NPPF in base and then destroying the RNA by nucleases or by chemical/physical treatments, such as base hydrolysis at elevated temperature, leaving the NPPF in direct proportion to how much had been hybridized to target nucleic acid. Alternatively, the sample can be treated so as to leave the (single strand) hybridized portion of the target nucleic acid, or the duplex formed by the hybridized target nucleic acid and the probe, to be further analyzed.

In some examples following incubation with a nuclease, base (such as NaOH or KOH) is added to increase the pH to about 9 to 12 and the sample heated (for example to 95° C. for 10 minutes). This dissociates the target molecule/CFS/NPPFs dimers, leaving the NPPF in a single stranded state, and in the case of RNA, hydrolyzes the RNA target molecules. This step can also neutralize or deactivate the nuclease, such as by raising the pH above about 6.

In some examples the sample is treated to adjust the pH to about 7 to about 8, for example by addition of acid (such as HCl). In some examples the pH is raised to about 7 to about 8 in Tris buffer. Raising the pH can prevent the depurination of DNA and also prevents many ss-specific nucleases (e.g., S1) from functioning fully.

In some examples, the sample is purified or separated to remove undesired nucleic acid or other molecules, prior to amplification, for example by gel purification or other separation method.

C. Amplification

The resulting NPPF molecules (or resulting target nucleic acid molecules that have been separated from the NPPF), which are in direct proportion to how much target nucleic acid molecules were present in the sample tested, can be amplified, for example using routine methods such as PCR or other forms of enzymatic amplification or ligation based methods of amplification.

Examples of in vitro amplification methods that can be used include, but are not limited to, quantitative real-time PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134). In one example, a ligation-based method of amplification is used, wherein the primers are NPPF specific and butt-up together so that they can be ligated together, melted off, and then fresh primers ligated together for a series of cycles. Ligation can be enzymatic or non-enzymatic. If the NPPF flanking sequences are used for hybridization of the primers, the amplification can be universal.

Quantitative real-time PCR is another form of in vitro amplifying nucleic acid molecules, enabled by Applied Biosystems (TaqMan PCR). The 5' nuclease assay provides a real-time method for detecting only specific amplification products. During amplification, annealing of the probe to its target sequence generates a substrate that is cleaved by the 5' nuclease activity of Taq DNA polymerase when the enzyme extends from an upstream primer into the region of the probe. This dependence on polymerization ensures that cleavage of the probe occurs only if the target sequence is being amplified. The use of fluorogenic probes makes it possible to eliminate post-PCR processing for the analysis of probe degradation. The probe is an oligonucleotide with both a reporter fluorescent dye and a quencher dye attached. While the probe is intact, the proximity of the quencher greatly reduces the fluorescence emitted by the reporter dye by Förster resonance energy transfer (FRET) through space. For real time PCR, the sample of NPPFs can be divided into separate wells or reaction locations, and a different NPPF-specific set of primers is added to each well or reaction location. Using probes (each having a different label permits multiplexing of real time PCR to measure multiple different NPPFs within a single well, or reaction location.

During amplification of the NPPF, an experiment tag, and/or sequencing adapter can be incorporated as, for instance, part of the primer and extension constructs, for example at the 3'- or 5'-end or at both ends. For example, an amplification primer, which includes a first portion that is complementary to all or part of NPPF flanking sequence, can include a second portion that is complementary to a desired experiment tag and/or sequencing adapter. One skilled in the art will appreciate that different combinations of experiment tags and/or sequencing adapters can be added to either end of the NPPF. In one example, the NPPF is amplified using a first amplification primer that includes a first portion complementary to all or a portion of the 3'-NPPF flanking sequence and a second portion complementary to (or comprising) a desired sequencing adapter, and the second amplification primer includes a first portion complementary to all or a portion of the 5'-NPPF flanking sequence and a second portion complementary to (or comprising) a desired experiment tag. In another example, the NPPF is amplified using a first amplification primer that includes all or a portion of a first portion complementary to the 3'-NPPF flanking sequence and a second portion complementary to (or comprising) a desired sequencing adapter and a desired experiment tag, and the second amplification primer includes a first portion complementary to all or a portion of the 5'-NPPF flanking sequence and a second portion complementary to (or comprising) a desired experiment tag.

It will be appreciated that NPPF-specific primers can be used to add sequencing adapters, experiment tags (including tags that permit capture of an NPPF by a substrate), and NPPF tags. The sample of NPPFs can be separated into separate wells or locations containing one or more different NPPF-specific primers, amplified, and then either sequenced separately or combined for sequencing (or detected).

Amplification can also be used to introduce a detectable label into the generated NPPF amplicons (for example if the NPPF was originally unlabeled or if additional labeling is desired), or other molecule that permits detection or quenching. For example, the amplification primer can include a detectable label, haptan, or quencher which is incorporated into the NPPF during amplification. Such a label, haptan, or quencher can be introduced at either end of the NPPF amplicon (or both ends), or anywhere in between.

In some examples, the resulting NPPF amplicons are cleaned up before detection or sequencing. For example, the amplification reaction mixture can be cleaned up before detection or sequencing using methods well known in the art (e.g., gel purification, biotin/avidin capture and release, capillary electrophoresis). In one example, the NPPF amplicons are biotinylated (or include another haptan) and captured onto an avidin or anti-haptan coated bead or surface, washed, and then released for detection or sequencing. Likewise, the NPPF amplicons can be captured onto a complimentary oligonucleotide (such as one bound to a surface), washed and then released for detection or sequencing. The capture of amplicons need not be particularly specific, as the disclosed methods eliminate most of the genome or transcriptome, leaving behind the NPPF that had been hybridized to target nucleic acid molecule. Other methods can be used to clean up the amplified product, if desired.

The amplified products can also be cleaned up after the last step of amplification, while still double stranded, by a method which uses a nuclease that hydrolyzes single stranded oligonucleotides (such as Exonuclease I), which nuclease can in turn be inactivated before continuing to the next step such as hybridization to a surface.

D. Detection of NPPF Amplicons

In some examples, the resulting amplicons are detected by any suitable means, for example based upon the detectable label present on the NPPF amplicons. In a specific, non-limiting example, the NPPF amplicons include a biotin label. In this example, the NPPF amplicons can be detected by incubating the amplicons (such as on a support, e.g., array or bead, containing the NPPF amplicons) with avidin-HRP, strepavidin-HRP, or a conjugate with another suitable enzyme such as alkaline phosphatase, and then contacting the support with chromogenic-, chemiluminescence-, or fluorescence-generating substrate. In one non-limiting example, the substrate is TMA-3 (Lumigen, Southfield, Mich.). Additional chemiluminescent substrates are commercially available, such as LumiGlo® (KPL, Gaithersburg, Md.), SuperSignal® (Pierce, Rockford, Ill.), and ECL™ (Amersham/GE Healthcare, Piscataway, N.J.). Signal produced by the substrate is detected, for example utilizing a microarray imager (such as an OMIX, OMIX HD, CAPELLA, or SUPERCAPELLA imager, HTG Molecular Diagnostics, Tucson, Ariz.) scanner, or visually such as in a lateral flow device. Europium-based luminescence can be used, as well as electroluminescence or light scatter, or electrical (e.g., conductivity or resistance). In another example, the NPPFs include a fluorescent label, such as Cy-3 or Cy-5. The NPPF amplicons can be detected utilizing a standard microarray imager (such as a Typhoon™ imager (GE Life Sciences, Piscataway, N.J.), a GenePix® microarray scanner (Molecular Devices, Sunnyvale, Calif.), GeneChip® scanner (Affymetrix, Santa Clara, Calif.), flow cytometry methods, or fluorescent microscopy methods. One of skill in the art can select suitable detection methods and reagents for these or other detectable labels.

E. Detection of NPPFs Utilizing Capture Molecules

In some embodiments, following hybridization, nuclease treatment, and amplification, the sample containing NPPF amplicons is contacted with a surface that includes multiple spatially discrete regions, each including a capture molecule, or is contacted with a plurality of surfaces, each including a capture molecule. For example, the surface can be a population of beads, wherein subpopulations of the beads each include at least one capture molecule. For example a first subpopulation could include at least one capture molecule, while a second subpopulation could include at least one capture molecule having a different sequence than the first, and so on. In some examples, the capture molecule includes at least one anchor associated with a bifunctional linker (also referred to as a "programming linker"). Alternatively, the capture molecule includes a nucleic acid capture probe, having a sequence that is complementary to at least a portion of an NPPF amplicon, such as complementary to all or a portion of a flanking region of an NPPF amplicon.

In an example where the capture molecule includes at least one anchor associated with a bifunctional linker, the anchor and the bifunctional linker are associated by hybridization, annealing, covalent linkage, or other binding. The bifunctional linker includes a first portion which specifically binds to (for example, is complementary to) the anchor and a second portion which specifically binds to (for example, is complementary to) one of the plurality of NPPF amplicons (such as complementary to all or a portion of region 102 of the NPPF 100 shown in FIG. 1)

In some embodiments, the disclosed methods include an anchor on a surface (for example on an array), which is associated with a bifunctional linker which is utilized to capture the NPPF amplicons following the amplification step. In some examples, an anchor is an oligonucleotide of about 8 to 150 nucleotides in length (for example, about 8 to 100, 15 to 100, 20 to 80, 25 to 75, or 25 to 50, such as about 15, 20, 25, 30, 35, 40, 45, 50, 55, 60, 65, 70, 75, 80, 85, 90, 95, 100, 110, 120, 130, 140, or 150 nucleotides). In one non-limiting example, the anchor is about 25 nucleotides in length. In some examples, the anchor includes a first portion that specifically binds to the first portion of the bifunctional linker and a second portion that acts as a spacer between the surface and the first portion of the anchor. In some examples, the second portion of the anchor is about 6 to 60 carbon atoms or nucleotides in length (such as about 6, 12, 24, 30, 36, 42, 48, 54, or 60 carbon atoms or nucleotides). In other examples, the second portion of the anchor is about 5 to 100 carbon atoms or nucleotides in length (such as about 10 to 50, 15 to 40, 20 to 30, or about 25 carbon atoms or nucleotides).

The base composition for anchors for the disclosed methods is such that the thermodynamic stability of the anchor and bifunctional linker pairing is high. In some examples, the percentage base composition for the anchors is about 30-40% G, 30-40% C, 10-20% A, and 10-20% T. In some examples, nearest neighbor frequency in the anchors minimizes G-G or C-C nearest neighbors to reduce side reactions mediated via G-quartet formation. In other examples, unnatural bases, or peptide nucleic acids, can be incorporated in the anchor or the bifunctional linker to modify its properties.

Methods of designing and synthesizing anchors of use in the disclosed methods are described, e.g., in PCT Publication No. WO 98/24098, incorporated herein by reference. In some examples, a set of anchors which are substantially dissimilar from one other is desirable. An exemplary algorithm for obtaining a set of dissimilar anchors is as follows:

1) The set size is defined. In some embodiments, 16, 24, 36, 48, 49, 64, 81, 96, and 100 constitute useful sizes.

2) The overall sequence structure of the anchor set is defined. The length and base composition as described above are used to define such parameters. In general, the number of G bases and C bases are held equal as are the number of A bases and T bases. This equality optimizes the configurational diversity of the final sets. Thus, such sets will be described by the equation $G_n C_n A_m T_m$.

3) For a set structure defined by m and n, a random number generator is employed to produce a set of random sequence isomers.

4) One member of the random sequence set is selected to be used as element #1 of the set.

5) The maximum similarity allowable among set members is defined. Similarity is defined in terms of local pair-wise base comparison. For example, when two oligomer strands of identical length n are aligned such that 5' and 3' ends are in register, the lack of mismatches refers to the situation where at all positions 1-n, bases in the two strands are identical. Complete mismatching refers to the situation wherein at all positions 1-n, bases in the two strands are different. For example, a useful maximum similarity might be 10 or more mismatches within a set of 16, 16 mer capture probes.

6) A second member of the random sequence set is selected and its similarity to element #1 is determined. If element #2 possesses less than the maximum allowable similarity to element #1, it will be kept in the set. If element #2 possesses greater than the maximum allowable similarity, it is discarded and a new sequence is chosen for comparison. This process is repeated until a second element has been determined.

7) In a sequential manner, additional members of the random sequence set are chosen which satisfy the dissimilarity constraints with respect to all previously selected elements.

One non-limiting example of a set of 16 anchors which can be utilized in the disclosed methods is shown in Table 1.

TABLE 1

Exemplary anchor sequences

| Anchor Sequence (5'->3') | SEQ ID NO: |
|---|---|
| TGATTCAGACCGGCCG | 1 |
| CCCGGGGCGTCTTAAC | 2 |
| GGACGCCATATGCGCT | 3 |
| TGAGGGCTCCGCCATA | 4 |
| AACCCGTGACGTGTGC | 5 |
| AGCATCGCCGGTCCTG | 6 |
| CCTGCAAGGCTGACGT | 7 |
| CAGTTGTCGACCCCGG | 8 |
| CGGCGCGTCCAATTCG | 9 |
| ATCGATCTGAGGGCCC | 10 |
| GTACATGCGGCCTGCA | 11 |
| TAGCCGCTCGCTAGAG | 12 |
| CCTAGTGATGACCGGC | 13 |
| GTCTGAGGGCAACCTC | 14 |
| CTAGCTGGCTACGCAG | 15 |
| GCCATCCGCTTGGAGC | 16 |

In other examples where the capture molecule includes at least one nucleic acid capture probe, having a sequence that is complementary to at least a portion of an NPPF amplicon, such as complementary to all or a portion of a flanking region of an NPPF amplicon. For example, the nucleic acid capture probe can include a region that is complementary to the NPPF amplicon, and may include a region that is not (such as a region that permits attachment of the probe to a surface). The nucleic acid capture probe can be directly attached to a surface. For example, the nucleic acid capture probe can include an amine for covalent attachment to a surface. In some examples, an nucleic acid capture probe is an oligonucleotide of at least 8 nucleotides in length, such as at least 10, at least 15, at least 20, at least 30, at least 50, or at least 100 nucleotides in length (for example, about 8 to 100, 15 to 100, 20 to 80, 25 to 75, or 25 to 50, such as about 15, 20, 25, 30, 35, 40, 45, 50, 55, 60, 65, 70, 75, 80, 85, 90, 95, 100, 110, 120, 130, 140, or 150 nucleotides). One skilled in the art will appreciate that the region of the nucleic acid capture probe complementary to a region of the NPPF amplicon need not be 100% complementary, as long as hybridization can occur between the nucleic acid capture probe and appropriate NPPF amplicons. In some examples, the region of the nucleic acid capture probe complementary to a region of the NPPF amplicon is at least 8 nucleotides in length, such as at least 8, at least 10, at least 15, at least 20, at least 30, at least 50, or at least 100 nucleotides in length (for example, about 8 to 100, 15 to 100, 20 to 80, 25 to 75, or 25 to 50, such as about 15, 20, 25, 30, 35, 40, 45, 50, 55, 60, 65, 70, 75, 80, 85, 90, 95, 100, 110, 120, 130, 140, or 150 nucleotides in length).

In some examples, the sample containing NPPF amplicons is denatured prior to contacting with the surface of the array (for example by heating to 95° C. for 5 minutes and rapidly chilling the sample on ice). In some examples, the sample containing NPPFs is adjusted prior to contacting with the surface (for example to adjust the concentration of salt or formamide). The sample containing NPPF amplicons is incubated with the surface (for example, an array or beads) for a sufficient period of time for the NPPF amplicons to specifically bind (for example, hybridize) to the capture molecule. In some examples, the incubation of the sample with the surface at about 37° C. to about 65° C. (for example, about 45° C. to about 60° C., or about 50° C. to about 60° C., such as 50° C.) for at least 1 hours (for example 1 to 8 hours, 1 to 36 hours, 12 to 24 hours, or 16 to 24 hours, or overnight) to allow the NPPF amplicons to hybridize to the capture molecule ("NPPF capture"). The capture time can be shorted, for example if using microfluidic or macrofluidic devices, lateral flow devices, or by reducing diffusion and using active flow or mixing.

Some of the surfaces (or substrates) which can be used in the disclosed methods are readily available from commercial suppliers. In some embodiments, the surface is a 96-, 384-, or 1536-well microtiter plate, such as modified plates sold by Corning Costar. In other embodiments, a substrate includes one or more beads (such as a population of beads that can be differentiated by size or color, for example by flow cytometry). Alternatively, a surface comprising wells which, in turn, comprise indentations or "dimples" can be formed by micromachining a substance such as aluminum or steel to prepare a mold, then microinjecting plastic or a similar material into the mold to form a structure. Alternatively, a structure comprised of glass, plastic, ceramic, or the like, can be assembled. The separator can be, for example, a piece of material, e.g., silicone, with holes spaced throughout, so that each hole will form the walls of a test well when the three pieces are joined. The subdivider can be, for example, a thin piece of material, e.g., silicone, shaped in the form of a screen or fine meshwork. The divider on the surface separating different reactions can also be a coated surface to which solutions will not adhere, or a nanostructure, or simply be individual drops, or capillaries or microfluidic channels or locations. In some examples, the base is a flat piece of material (for example glass or plastic), in, for example, the shape of the lower portion of a typical microplate used for a biochemical assay. The top surface of the base can be flat, or can be formed with indentations that will align with the subdivider shape to provide full subdivisions, or wells, within each sample well. The three pieces can be joined by standard procedures, for example the procedures used in the assembly of silicon wafers.

Suitable materials for the surface include, but are not limited to: glass, silica, gold, silver, a gel or polymer, nitrocellulose, polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, ethyleneacrylic acid, thylene methacrylic acid, and blends of copolymers thereof (see U.S. Pat. No. 5,985,567), or comprised of nanomaterials including carbon.

In general, suitable characteristics of the material that can be used to form the surface include: being amenable to surface activation such that upon activation, the surface of the support is capable of covalently attaching a biomolecule such as an oligonucleotide (e.g., anchor) thereto; amenability to "in situ" synthesis of biomolecules; being chemically inert such that at the areas on the support not occupied by oligonucleotides or proteins are not amenable to non-specific binding, or when non-specific binding occurs, such materials can be readily removed from the surface without removing the oligonucleotides or proteins. The surfaces can be permeable, partially permeable, or impermeable.

A wide variety of array formats for arrangement of the anchors can be employed in accordance with the present disclosure. One suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate.

Oligonucleotide anchors, bifunctional linkers, and other capture molecules (as well as NPPFs, CFSs, and PCR probes/primers) can be synthesized by conventional technology, for example, with a commercial oligonucleotide synthesizer and/or by ligating together subfragments that have been so synthesized. Nucleic acids which are too long to be reliably synthesized by such methods can be generated by amplification procedures, using conventional procedures.

In one embodiment, preformed nucleic acid anchors (e.g., oligonucleotide anchors) or nucleic acid capture probes having a sequence complementary to at least a portion of an NPPF amplicon (e.g., oligonucleotide probes), can be situated on or within the surface of a test region by any of a variety of conventional techniques, including photolithographic or silkscreen chemical attachment, disposition by ink jet technology, capillary, screen or fluid channel chip, electrochemical patterning using electrode arrays, contacting with a pin or quill, or denaturation followed by baking or UV-irradiating onto filters (see, e.g., Rava et al. (1996). U.S. Pat. No. 5,545,531; Fodor et al. (1996). U.S. Pat. No. 5,510,270; Zanzucchi et al. (1997). U.S. Pat. No. 5,643,738; Brennan (1995). U.S. Pat. No. 5,474,796; PCT WO 92/10092; PCT WO 90/15070). Oligonucleotide anchors or probes can be placed on top of the surface of a test region or can be, for example in the case of a polyacrylamide gel pad, imbedded within the surface in such a manner that some of the anchor or probe protrudes from the gel structure into aqueous portions within the gel and gel surface and is available for interactions with a linker or NPPF. This is true for permeable surfaces and partially permeable surfaces, such as a surface where the first portion, such as the area of the surface in contact with the solutions containing bifunctional linkers or NPPFs is permeable but a second portion, such as at some distance into the surface, is not permeable. In one embodiment, preformed oligonucleotide anchors or probes are derivatized at the 5' end with a free amino group; dissolved at a concentration routinely determined empirically (e.g., about 1 μM) in a buffer such as 50 mM phosphate buffer, pH 8.5 and 1 mM EDTA; and distributed with a Pixus nanojet dispenser (Cartesian Technologies) in droplets of about 10.4 nanoliters onto specific locations within a test well whose upper surface is that of a fresh, dry DNA Bind plate (Corning Costar). Depending on the relative rate of oligonucleotide attachment and evaporation, it may be required to control the humidity in the wells during preparation. In another embodiment, oligonucleotide anchors or probes can be synthesized directly on the surface of a test region, using conventional methods such as, for example, light-activated deprotection of growing oligonucleotide chains (for example, in conjunction with the use of a site directing "mask") or by patterned dispensing of nanoliter droplets of deactivating compound using a nanojet dispenser. Deprotection of all growing oligonucleotides that are to receive a single nucleotide can be done, for example, and the nucleotide then added across the surface. In another embodiment, oligonucleotide anchors or probes are attached to the surface via the 3' ends of the oligonucleotides, using conventional methodology.

F. Detection of NPPs Utilizing Alternative Methods

In some embodiments, following hybridization, nuclease treatment, and amplification, the NPPF amplicons are detected utilizing alternative methods, such as high-throughput platforms. In some examples, NPPF amplicons are detected utilizing gel electrophoresis, chromatography, mass spectrometry, sequencing, conventional microarray analysis, detected during the PCR amplification step, or hybrid capture. In some embodiments, the NPPF amplicons do not include a detectable label and indirect detection methods are utilized. Such methods are known to one of skill in the art and include, but are not limited to, those described herein.

In one example, NPPF amplicons are detected utilizing a bead-based assay, such as a bead array. One example of a bead-based assay utilizes X-MAP® beads (Luminex, Austin, Tex.), such as a QBEAD assay. In some examples, the NPPs are captured on X-MAP® beads or other beads by hybridization to an oligonucleotide associated with the beads (for example about 1 hour at about 50° C.). The detectable label included in the NPPF amplicons can be detected, for example by flow cytometry (such as utilizing a Luminex 200, Flexmap 3D, or other suitable instrument).

In another example, NPPF amplicons are detected utilizing a standard microarray. One example of such an array is a Nimblegen microarray (Nimblegen, Madison, Wis.). In some examples, the NPPF amplicons are hybridized to an array including oligonucleotides that specifically bind to the NPPF amplicons. The detectable label included in the NPPF amplicons can be detected.

In some examples, NPPF amplicons are detected with a "bar code" assay. One example of such as assay is nCounter® Analysis System (Nanostring Technologies, Seattle, Wash.). In some examples, the NPPF amplicons are hybridized to a probe including one or more color coded tags (a "bar-code"). Detection of the color coded tags provides identification of the NPPF amplicon. See, e.g., WO 07/0761282; WO 07/076129; WO 07/139766.

F. Sequencing of Amplicons

In some examples, the resulting NPPF amplicons are sequenced, for example by sequencing the entire NPPF amplicon, or a portion thereof (such as an amount sufficient to permit identification of the target nucleic acid molecule). The disclosure is not limited to a particular sequencing method. In some examples, multiple different NPPF amplicons are sequenced in a single reaction. In one example, an experiment tag of the NPPF amplicon, which can be designed to correspond to a particular target sequence, can be sequenced. Thus, if the 3' end of the NPPF amplicon has a sequence at the terminal 2 to 25 nucleotides (such as the terminal 2 to 5 or 2 to 7, for example the terminal 2, 3, 4, 5, 6, 7, 8, 9, or 10 nucleotides) which represent a unique sequence for each target measured, then this is all of the NPPF amplicon that needs to be sequenced to identify the target, and by counting the number of such experiment tags sequenced, the amount of each target in the sample can be determined.

In one example, the resulting NPPF amplicons, such as one composed of DNA, is sequenced using the chain termination method. This technique uses sequence-specific termination of a DNA synthesis reaction using modified nucleotide substrates. In chain terminator sequencing, extension is initiated at a specific site on the NPPF amplicon by using an oligonucleotide primer complementary to a portion of the NPPF amplicon. The oligonucleotide primer is extended using a polymerase, such as a RNA or DNA polymerase. Included with the primer and polymerase are the four deoxynucleotide bases (or ribonucleotide), along with a low concentration of a chain terminating nucleotide (commonly a di-deoxynucleotide). Limited incorporation of the chain terminating nucleotide by the polymerase results in a series of related nucleic acid fragments that are terminated only at positions where that particular nucleotide is used. The fragments are then size-separated, for example by electrophoresis in a slab polyacrylamide gel, or in a narrow glass tube (capillary) filled with a viscous polymer.

An alternative method is dye terminator sequencing. Using this approach permits complete sequencing in a single reaction, rather than the four needed with the chain termination method. This is accomplished by labeling each of the dideoxynucleotide chain-terminators with a separate fluorescent dye, which fluoresces at a different wavelength.

In another example pyrosequencing is used, such as the methods commercialized by Biotage (for low throughput sequencing) and 454 Life Sciences (for high-throughput sequencing). In the array-based method (e.g., 454 Life Sciences), single-stranded nucleic acid (such as DNA) is annealed to beads and amplified via EmPCR. These nucleic acid-bound beads are then placed into wells on a fiber-optic chip along with enzymes which produce light in the presence of ATP. When free nucleotides are washed over this chip, light is produced as ATP is generated when nucleotides join with their complementary base pairs. Addition of one (or more) nucleotide(s) results in a reaction that generates a light signal that is recorded, for example by a CCD camera The signal strength is proportional to the number of nucleotides, for example, homopolymer stretches, incorporated in a single nucleotide flow.

In another example, the NPPF amplicons are sequenced using a Illumina® (e.g., HiSeq) or Ion Torrent®, 454®, Helicos, PacBio®, Solid® (Applied Vioasystems) or any number of other commercial sequencing systems. Sequencing adapters (such as a poly-A or poly T tails present on the NPPF amplicons, for example introduced using PCR) are used for capture. Sequencing by 454® or Illumina® typically involves library preparation, accomplished by random fragmentation of DNA, followed by in vitro ligation of common adaptor sequences. For the disclosed methods, the step of random fragmentation of the nucleic acid to be sequenced can be eliminated, and the in vitro ligation of adaptor sequences can be to the NPPF amplicons, such as an experiment tag present in the NPPF amplicons, though these can also be incorporated by use of the flanking regions and PCR, avoiding the need for ligation. Once captured through sequencing adaptors to the sequencing chip/bead, bridge amplification is performed to form colonies of each probe for sequencing. In these methods, the NPPF amplicons end up spatially clustered, either to a single location on a planar substrate (Illumina®, in situ colonies, bridge PCR), or to the surface of micron-scale beads (454®, emulsion PCR), which can be recovered and arrayed (emulsion PCR). The sequencing method includes alternating cycles of enzyme-driven biochemistry and imaging-based data acquisition. These platforms rely on sequencing by synthesis, that is, serial extension of primed templates. Successive iterations of enzymatic interrogation and imaging are used to build up a contiguous sequencing read for each array feature. Data are acquired by imaging of the full array at each cycle (e.g., of fluorescently labeled nucleotides incorporated by a polymerase). each cycle (e.g., of fluorescently labeled nucleotides incorporated by a polymerase). More than one sequencing primer can be used on the colonies formed on the flow cell, permitting either dual-end sequencing, or sequencing of one or more other portions of the amplicon, such as a barcode or index tag, or experimental tag.

For 454®, a sequencing primer is hybridized to the NPPF after amplification on the sequencing chip/bead amplicon. Sequencing is performed by pyrosequencing. Amplicon-bearing beads are pre-incubated with *Bacillus stearothermophilus* (Bst) polymerase and single-stranded binding protein, and then deposited on to a microfabricated array of picoliter-scale wells, one bead per well, rendering this biochemistry compatible with array-based sequencing. Smaller beads are also added, bearing immobilized enzymes also required for pyrosequencing (ATP sulfurylase and luciferase). During the sequencing, one side of the semi-ordered array functions as a flow cell for introducing and removing sequencing reagents. The other side is bonded to a fiber-optic bundle for CCD-based signal detection. At each cycle, a single species of unlabeled nucleotide is introduced. For sequences where this introduction results in incorporation, pyrophosphate is released via ATP sulfurylase and luciferase, generating a burst of light detected by the CCD for specific array coordinates. Across multiple cycles, the pattern of detected incorporation events reveals the sequence of templates represented by individual beads.

For methods that use bridge PCR (e.g., Illumina®), amplified sequencing features are generated by bridge PCR. Both forward and reverse PCR primers are tethered to a solid substrate by a flexible linker, such that all amplicons arising from any single template molecule during the amplification remain immobilized and clustered to a single physical location on an array. In some examples, bridge PCR uses alternating cycles of extension with Bst polymerase and denaturation (e.g., with formamide). The resulting 'clusters' each consist of about 1,000 clonal amplicons. Several million clusters can be amplified to distinguishable locations within each of eight independent 'lanes' that are on a single flow-cell (such that eight independent experiments can be sequenced in parallel during the same instrument run). After cluster generation, the amplicons are linearization and a sequencing primer is hybridized to a universal adaptor sequence flanking the region of interest. Each cycle of sequence interrogation consists of single-base extension with a modified DNA polymerase and a mixture of four nucleotides. These nucleotides are 'reversible terminators', in that a chemically cleavable moiety at the 3' hydroxyl position allows only a single-base incorporation to occur in each cycle, and one of four fluorescent labels, also chemically cleavable, corresponds to the identity of each nucleotide. After single-base extension and acquisition of images in four channels, chemical cleavage of both groups sets up for the next cycle. Read-lengths up to 36 bp are currently routinely performed.

In one example, the Helicos® or PacBio® single molecule sequencing method is used.

It will be appreciated that the NPPF can be designed for sequencing by any method, on any sequencer developed currently or in the future. The NPPF itself does not limit the method of sequencing used, nor the enzyme used. Other methods of sequencing are or will be developed, and one skilled in the art can appreciate that the generated NPPF amplicons (or DNA hybridized to the NPPF) will be suitable for sequencing on these systems.

G. Controls

In some embodiments, the method includes the use of one or more positive and/or negative controls subject to the same reaction conditions as the actual experimental NPPFs. The use of tagging permits actual different samples to be used as controls but processed for sequencing and run in the same sequencing lane as test samples. DNA can be measured as a control for the number of cells when measuring target RNA.

In some examples, a "positive control" includes an internal normalization control for variables such as the number of cells lysed for each sample, the recovery of DNA or RNA, or the hybridization efficiency, such as one or more NPPFs, CFSs, corresponding linkers, and the like, which are specific for one or more basal level or constitutive housekeeping genes, such as structural genes (e.g., actin, tubulin, or others) or DNA binding proteins (e.g., transcription regulation factors, or others). In some examples, a positive control includes glyceraldehyde-3-phosphate dehydrogenase (GAPDH), peptidylproylyl isomerase A (PPIA), large ribosomal protein (RPLP0), ribosomal protein L19 (RPL19), or other housekeeping genes discussed below. Other positive controls can be spiked into the sample to control for the assay process, independent of sample.

In other examples, a positive control includes an NPPF specific for an DNA or RNA that is known to be present in the sample (for example a nucleic acid sequence likely to be present in the species being tested, such as a housekeeping gene). For example, the corresponding positive control NPPF can be added to the sample prior to or during hybridization with the plurality of test NPPFs. Alternatively, the positive control NPPF is added to the sample after nuclease treatment.

In some examples, a positive control includes an nucleic acid molecule known to be present in the sample (for example a nucleic acid sequence likely to be present in the species being tested, such as a housekeeping gene). The corresponding positive control nucleic acid molecule (such as in vitro transcribed nucleic acid or nucleic acid isolated from an unrelated sample) can be added to the sample prior to or during hybridization with the plurality of NPPFs.

In some examples, a "negative control" includes one or more NPPFs, CFSs, corresponding linkers, or the like, whose complement is known not to be present in the sample, for example as a control for hybridization specificity, such as a nucleic acid sequence from a species other than that being tested, e.g., a plant nucleic acid sequence when human nucleic acids are being analyzed (for example, *Arabidopsis thaliana* AP2-like ethylene-responsive transcription factor (ANT)), or a nucleic acid sequence not found in nature.

In some embodiments, the signal from each NPPF amplicon is normalized to the signal of at least one housekeeping nucleic acid molecule, for example to account for differences in cellularity between samples. Exemplary housekeeping genes include one or more of GAPDH (glyceraldehyde 3-phosphate dehydrogenase), SDHA (succinate dehydrogenase), HPRT1 (hypoxanthine phosphoribosyl transferase 1), HBS1L (HBS1-like protein), β-actin (ACTB), β-2 microglobulin (B2m), and AHSP (alpha hemoglobin stabilizing protein). One of skill in the art can select additional housekeeping genes for use in normalizing signals in the disclosed methods, including, but not limited to ribosomal protein S13 (RPS13), ribosomal protein S20 (RPS20), ribosomal protein L27 (RPL27), ribosomal protein L37 (RPL37), ribosomal protein 38 (RPL38), ornithine decarboxylase antizyme 1 (OAZ1), polymerase (RNA) II (DNA directed) polypeptide A, 220 kDa (POLR2A), yes-associated protein 1 (YAP1), esterase D (ESD), proteasome (prosome, macropain) 26S subunit, ATPase, 1 (PSMC1), eukaryotic translation initiation factor 3, subunit A (EIF3A), or 18S rRNA (see, e.g., de Jonge et al., *PLoS One* 2:e898, 2007; Saviozzi et al., *BMC Cancer* 6:200, 2006; Kouadjo et al., *BMC Genomics* 8:127, 2007; each of which is incorporated herein by reference). The normalized values can be directly compared between samples or assays (for example, between two different samples in a single assay or between the same sample tested in two separate assays).

IV. Nuclease Protection Probes with Flanking Sequences (NPPFs)

The disclosed methods permit detection and/or sequencing of one or more target nucleic acid molecules, for example simultaneously or contemporaneously. Based on the target nucleic acid, NPPFs can be designed for use in the disclosed methods using the criteria set forth herein in combination with the knowledge of one skilled in the art. In some examples, the disclosed methods include generation of one or more appropriate NPPFs for detection of particular target nucleic acid molecules. The NPPF, under a variety of conditions (known or empirically determined), specifically binds (or is capable of specifically binding) to a target nucleic acid or portion thereof, if such target is present in the sample.

The NPPFs include a region that is complementary to a target nucleic acid molecule, such that for each particular target nucleic acid sequence, there is at least one NPPF in the reaction that is specific for the target nucleic acid sequence. For example, if there are 2, 3, 4, 5, 6, 7, 8, 9 or 10 different target nucleic acid sequences to be detected or sequenced, the method will correspondingly use at least 2, 3, 4, 5, 6, 7, 8, 9 or 10 different NPPFs (wherein each NPPF corresponds to a particular target). Thus in some examples, the methods use at least two NPPFs, wherein each NPPF is specific for a different target nucleic acid molecule. However, one will appreciate that several different NPPFs can be generated to a particular target nucleic acid molecule, such as many different regions of a single target nucleic acid sequence. In one example, an NPPF includes a region that is complementary to a sequence found only in a single gene in the transcriptome. NPPFs are designed to be specific for a target nucleic acid molecule and to have similar Tm's (if to be used in the same reaction).

Thus, a single sample may be contacted with one or more NPPFs. A set of NPPFs is a collection of two or more NPPFs each specific for a different target and/or a different portion of a same target. A set of NPPFs can include at least, up to, or exactly 2, 3, 4, 5, 6, 7, 8, 9, 10, 12, 15, 20, 25, 30, 50, 100, 500, 1000, 2000, 3000, 5000 or 10,000 different NPPFs. In some examples, a sample is contacted with a sufficient amount of NPPF to be in excess of the target for such NPPF, such as a 100-fold, 500-fold, 1000-fold, 10,000-fold, 100,000-fold or $10^6$-fold excess. In some examples, if a set of NPPFs is used, each NPPF of the set can be provided in excess to its respective target (or portion of a target) in the sample. Excess NPPF can facilitate quantitation of the amount of NPPF that binds a particular target. Some method embodiments involve a plurality of samples (e.g., at least, up to, or exactly 10, 25, 50, 75, 100, 500, 1000, 2000, 3000, 5000 or 10,000 different samples) simultaneously or contemporaneously contacted with the same NPPF or set of NPPFs.

FIG. 1 shows an exemplary NPPF 100 having a region 102 that includes a sequence that specifically binds to or hybridizes to the target nucleic acid sequence, as well as flanking sequences 104, 106 at the 5'- and 3'-end of the NPPF, wherein the flanking sequences bind or hybridize to their complementary sequences (referred to herein as CFSs). The NPPFs (as well as CFSs that bind to the NPPFs) can be composed of natural (such as ribonucleotides (RNA), or deoxyribonucleotides (DNA)) or unnatural nucleotides (such as locked nucleic acids (LNAs, see, e.g., U.S. Pat. No. 6,794,499), peptide nucleic acids (PNAs)), and the like. The NPPFs can be single- or double-stranded. In some examples, the NPPFs include one or more synthetic bases or alternative bases (such as inosine). Modified nucleotides, unnatural nucleotides, synthetic, or alternative nucleotides can be used in NPPFs at one or more positions (such as 1, 2, 3, 4, 5, or more positions). In some examples, use of one or more modified or unnatural nucleotides in the NPPF can increase the $T_m$ of the NPPF relative to the $T_m$ of a NPPF of the same length and composition which does not include the modified nucleic acid. One of skill in the art can design probes including such modified nucleotides to obtain a probe with a desired $T_m$. In one example, an NPPF is composed of DNA or RNA, such as single stranded (ssDNA) or branched DNA (bDNA). In one example, an NPPF is an aptamer.

Methods of empirically determining the appropriate size of a NPPF for use with particular targets or samples (such as fixed or crosslinked samples) are routine. In specific embodiments, a NPPF can be up to 500 nucleotides in length, such as up to 400, up to 250, up to 100, or up to 75 nucleotides in length, including, for example, in the range of 20-500, 20-250, 25-200, 25-100, 25-75, or 25-50 nucleotides in length. In one non-limiting example, an NPPF is at least 35 nucleotides in length, such as at least 40, at least 45, at least 50, at least 75, at least 100, at least 150, or at least 200 nucleotides in length, such as 50 to 200, 50 to 100 or 75 to 200, or 36, 72, or 100 nucleotides in length. Particular NPPF embodiments may be longer or shorter depending on desired functionality. In some examples, the NPPF is appropriately sized (e.g., sufficiently small) to penetrate fixed and/or crosslinked samples. Fixed or crosslinked samples may vary in the degree of fixation or crosslinking; thus, an ordinarily skilled artisan may determine an appropriate NPPF size for a particular sample condition or type, for example, by running a series of experiments using samples with known, fixed target concentration(s) and comparing NPPF size to target signal intensity. As NPPF length increases, in such an experiment, at some point target signal intensity should begin to decrease. In some examples, the sample (and, therefore, at least a proportion of target) is fixed or crosslinked, and the NPPF is sufficiently small that signal intensity remains high and does not substantially vary as a function NPPF size.

The sequence 102 that specifically binds to the target nucleic acid sequence is complementary in sequence to the target nucleic acid sequence to be detected or sequenced. One skilled in the art will appreciate that the sequence 102 need not be complementary to an entire target nucleic acid (e.g., if the target is a gene of 100,000 nucleotides, the sequence 102 can be a portion of that, such as at least 10, at least 15, at least 20, at least 25, at least 30, at least 40, at least 50, at least 100, or more consecutive nucleotides complementary to a particular target nucleic acid molecule). The specificity of a probe increases with length. Thus for example, a sequence 102 that specifically binds to the target nucleic acid sequence which includes 25 consecutive nucleotides will anneal to a target sequence with a higher specificity than a corresponding sequence of only 15 nucleotides. Thus, the NPPFs disclosed herein can have a sequence 102 that specifically binds to the target nucleic acid sequence which includes at least 10, at least 15, at least 20, at least 25, at least 30, at least 40, at least 50, at least 100, or more consecutive nucleotides complementary to a particular target nucleic acid molecule (such as about 6 to 50, 10 to 40, 10 to 60, 15 to 30, 18 to 23, 19 to 22, or 20 to 25 consecutive nucleotides complementary to a target DNA or a target RNA). Particular lengths of sequence 102 that specifically binds to the target nucleic acid sequence that can be part of the NPPFs used to practice the methods of the present disclosure include 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous nucleotides complementary to a target nucleic acid molecule. In some examples where the target nucleic acid molecule is an miRNA (or siRNA), the length of the sequence 102 that specifically binds to the target nucleic acid sequence can be shorter, such as 20-30 nucleotides in length (such as 20, 21, 22, 23, 24, 25, 26, 27, 28 29, or 30 nucleotides) to match the miRNA (or siRNA) length. However, one skilled in the art will appreciate that the sequence 102 that specifically binds to the target need not be 100% complementary to the target nucleic acid molecule. Depending on the reaction conditions and the corresponding selectivity of the nuclease used, more than one mismatch may be required (such as at least two adjacent mismatches) for nuclease digestion to occur. In some examples, the NPPF is degenerate at one or more positions (such as 1, 2, 3, 4, 5, or more positions), for example, a mixture of nucleotides (such as 2, 3, or 4 nucleotides) at a specified position in the sequence 104 that specifically binds to the target.

The sequence 102 also specifically binds to a programming or bifunctional linker (wherein a region of the bifunctional linker is complementary to sequence 102). In some embodiments, following hybridization and nuclease treatment, the sample is contacted with a surface (such as one that includes multiple spatially discrete regions), including at least capture molecule, such as an anchor associated with a programming linker or a nucleic acid capture probe that includes a sequence complementary to a portion of the NPPF amplicon (such as a flanking sequence or portion thereof). As shown in FIG. 3, the bifunctional linker 216 includes a first portion which specifically binds to (for example, is complementary to) the anchor 214 and a second portion which specifically binds to (for example, is complementary to) a region of the NPPF amplicon 210. In some examples, the NPPF amplicon has at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous nucleotides complementary to the bifunctional linker.

The sequence of the flanking sequence 104, 106 can provide a universal amplification point that is complementary to at least a portion of an amplification primer. The flanking sequence thus permits multiplexing, as the same amplification primers can be used to amplify NPPFs specific for different target nucleic acid molecules. The flanking sequence is not similar to a sequence found in the target genome. For example, if the target nucleic acid is a human sequence, the sequence of the flanking sequence is not similar to a sequence found in the target genome. This helps to reduce binding of non-target sequences that may be present in the target genome from binding to the NPPFs. Methods of analyzing a sequence for its similarity to a genome are well known in the art.

The flanking sequence 104, 106 can also be used to permit capture of an NPPF amplicon, for example capture to a substrate. For example, an NPPF containing a flanking sequence that includes a sequence complementary to a nucleic acid capture probe present on a surface (such as directly conjugated to a surface), can hybridize to the nucleic acid capture probe permitting capture or binding of the NPPF amplicon to the surface. Thus, in some examples, the flanking sequence includes (or permits addition of, for example during amplification) of an experimental tag, such as one that permits capture of the NPPF amplicon. One will appreciate that other experimental tags can be used, such as those used to uniquely identify an NPPF or populations of NPPFs, and that such experimental tags can be part of the NPPF, or can be added later, for example by using a primer complementary to the flanking sequence and which also includes a sequence complementary to the tag to be added to the resulting amplicon. The flanking sequences also permit labeling of the NPPF, for example during amplification of the NPPF, or by using a labeled probe that is complementary to the flanking sequence, and allowing the probe to bind to the NPPF. In some examples, the flanking sequence includes (or permits addition of, for example during amplification) of a sequencing adapater, such as a poly-A or poly-T sequence needed for some sequencing platforms.

One will appreciate than an NPPF can include one or two flanking sequences (e.g., one at the 5'-end, one at the 3'-end, or both), and that the flanking sequences can be the same or different. As illustrated in FIGS. 6A and B, the NPPF can include a single flanking sequence. FIGS. 6A and 6B show the flanking sequence at the 5'-end, but one will appreciate it can also be at the 3'-end instead. FIG. 6A shows an example where all of the NPPFs in the reaction have the same flanking sequence F1. Amplification with an F1-specific primer (such as a labeled primer) could be used to add the same 5'- or 3'-tag (e.g., sequencing adaptor or experimental tag) to each NPPF. For example, the same sequencing adapter could be added to all of the NPPFs, permitting sequencing of the NPPFs in the same sequencing platform. FIG. 6B shows an example where each NPPF (or each subpopulation of NPPFs) in the reaction have a different flanking sequence, F1 to F3. For example, F1, F2, and F3 could be complementary to a capture nucleic acid probe 1, 2, and 3, respectively on a surface. This eliminates the need for bifunctional linkers (e.g., see bottom of FIG. 3). In another example, amplification with T1-F1-, T2-F2-, and T3-F3-specific primers can be used to add a different experimental tag to each different NPPF (or populations of NPPFs).

As illustrated in FIGS. 6C-6F, the NPPF can in some examples include two flanking sequences, one at the 5'-end the other at the 3'-end of the NPPF. FIG. 6C shows an example where all of the NPPFs in the reaction have the same flanking sequence, F1, at both ends. FIG. 6D shows an example wherein all of the flanking sequences on the 5'-end are the same (e.g., F1), and all of the flanking sequences on the 3'-end are the same (e.g., F(a)), but the 5'-end and 3'-end flanking sequences differ. In such an example, this permits the inclusion of for example of the same experimental tag on one end of the NPPFs, and the inclusion of for example of the same sequencing adaptor to the other side of the NPPFs. As there will be no primer hybridization bias each NPPF should be tagged with the same fidelity. FIG. 6E shows an example wherein all of the flanking sequences on one end are the same (e.g., F1 on the 5'-end), but all of the flanking sequences on the other end differ from one another (e.g., F(a), F(b), and F(c)). In such an example, this permits the use of a single capture probe to capture all of the NPPFs (e.g., using a capture probe having at least a portion of its sequence complementary to F1). The flanking sequences on the other end, F(a), F(b) & F(c), could be used for example to differentially label each NPPF (such as using different experiment tags). Alternatively, F(a), F(b) & F(c) could be complementary to capture probes 1, 2, and 3, respectively, and F1 could be used a to label all of the NPPFs in the same way. FIG. 6F shows an example wherein all of the flanking sequences are different, irrespective of their position (e.g., F(a), F(b), F(c), F1, F2, and F3). In this example, each flanking sequence can be used for a different experiment tag or for combinations of different experiment tags and different sequencing adapters.

Thus, an NPPF sequence can be represented by 1-2-3 where 1 and 3 are flanking sequences on either side of sequence 2 (which is complementary to the target nucleic acid). Each of these regions can hybridized at some point in the method to its complementary sequence. For example, A can be complementary to flanking sequence 1 of the NPPF (e.g., A can be a CFS complementary to sequence 1), B can be complementary to sequence 2 of the NPPF (e.g., a target sequence complementary to sequence 2), and C can be complementary to the flanking sequence 3 of the NPPF (e.g., C can be a CFS complementary to sequence 3). This is what occurs during the hybridization of the target nucleic acid molecules and CFSs, to their corresponding NPPF. For example:

1-2-3
A-B-C

In some examples, the, experimental tags (such as those that distinguish experiments or patients from one another) and sequencing adapters, represented by D and E respectively, are added using the flanking sequences, for example during amplification (such that the amplification primer is complementary to the flanking sequence and includes a sequence complementary to the tag or adapter to be added to the resulting NPPF amplicon). For example, amplification of the NPPF with such primers would result in a sequence as follows: E-1-2-3-D or D-1-2-3-E.

The table below also shows five exemplary combinations of 5'-tags (such as experimental tags or sequencing adpaters), 5'-flanking sequences, target-specific sequences, 3'-flanking sequences, and 3'-tags. The 5'-tags and 3'-tags are added during amplification. The 5'-flanking sequences and 3'-flanking sequences are sequences that are part of the original NPPF (and thus part of the flanking sequence itself).

|  | 5'-Tag | 5'-Flanking Sequence | Target-specific Sequence | 3'-Flanking Sequence | 3'-Tag |
|---|---|---|---|---|---|
| Ex. 1 | None | Sequencer Adapter |  | Sequencer Adapter | None |
| Ex. 2 | Sequencing Adapter | Sequence-specific identifier |  | Sequence-specific identifier | Sequencing Adapter |
| Ex. 3 | Experimental tag (short sequence or modified bases, identifer for one/several reactions to be independently discerned: by (i.e.) patient, sample, cell type, time | Experimental tag (short sequence or modified bases, identifer for one/several reactions to be independently discerned: by (i.e.) patient, sample, cell |  | Experimental tag (short sequence or modified bases, identifer for one/several reactions to be independently discerned: by (i.e.) patient, sample, cell type, time | Experimental tag (short sequence or modified bases, identifer for one/several reactions to be independently discerned: by (i.e.) patient, sample, cell |

-continued

| | 5'-Tag | 5'-Flanking Sequence | Target-specific Sequence | 3'-Flanking Sequence | 3'-Tag |
|---|---|---|---|---|---|
| | course timepoint, treatment) | type, time course timepoint, treatment) | | course timepoint, treatment) | type, time course timepoint, treatment) |
| Ex. 4 | Biotin or other detection (e.g., hapten) tag/capture sequence | Biotin or other detection (e.g., hapten) tag/capture sequence | | Biotin or other detection (e.g., hapten) tag/capture sequence | Biotin or other detection (e.g., hapten) tag/capture sequence |
| Ex. 5 | Site for cleavage (enzymatic/ modified base) | Site for cleavage (enzymatic/ modified base) "Buffer" (e.g., spacer or universal) sequence | | Site for cleavage (enzymatic/ modified base) "Buffer" (e.g., spacer or universal) sequence | Site for cleavage (enzymatic/ modified base) |

In specific examples, each flanking sequence does not specifically bind to any other NPPF sequence (e.g., sequence 102 or other flanking sequence) or to any component of the sample. In some examples, if there are two flanking sequences, the sequence of each flanking sequence 104, 106 is different. Ideally, if there are two different flaking sequences (for example two different flaking sequences on the same NPPF and/or to flaking sequences of other NPPFs in a set of NPPFs), each flanking sequence 104, 106 has a similar melting temperature ($T_m$), such as a $T_m$+/−about 10° C. or +/−5° C. of one another, such as +/−4° C., 3° C., 2° C., or 1° C.

In particular examples, the flanking sequence 104, 106 is at least 12 nucleotides in length, such as at least 15, at least 20, at least 25, at least 30, at least 40, or at least 50 nucleotides in length, such as 12-50 or 12-30 nucleotides, for example, 20, 21, 22, 23, 24, 25, 26, 27, 28, 29 or 30 nucleotides in length, wherein the contiguous nucleotides not found in a nucleic acid molecule present in the sample to be tested. The flanking sequences are protected from degradation by the nuclease by hybridizing molecules to the flanking sequences which have a sequence complementary to the flanking sequences (CFSs).

Factors that affect NPPF-target and NPPF-CFS hybridization specificity include length of the NPPF and CFS, melting temperature, self-complementarity, and the presence of repetitive or non-unique sequence. See, e.g., Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999. Conditions resulting in particular degrees of hybridization (stringency) will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. In some examples, the NPPFs utilized in the disclosed methods have a $T_m$ of at least about 37° C., at least about 42° C., at least about 45° C., at least about 50° C., at least about 55° C., at least about 60° C., at least about 65° C., at least about 70° C., at least about 75° C., at least about 80° C., such as about 42° C.-80° C. (for example, about 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80° C.). In one non-limiting example, the NPPFs utilized in the disclosed methods have a $T_m$ of about 42° C. Methods of calculating the $T_m$ of a probe are known to one of skill in the art (see e.g., Sambrook et al., *Molecular Cloning: A Laboratory Manual*, 3d ed., Cold Spring Harbor Press, 2001, Chapter 10). In some examples, the NPPFs for a particular reaction are selected to each have the same or a similar $T_m$ in order to facilitate simultaneous detection or sequencing of multiple target nucleic acid molecules in a sample, such as $T_m$s+/− about 10° C. of one another, such as +/−10° C., 9° C., 8° C., 7° C., 6° C., 5° C., 4° C., 3° C., 2° C., or 1° C. of one another.

A. Flanking Sequences

One or both of the flanking sequences of the NPP (e.g., 104 or 106 of FIG. 1) include a sequence that provides a universal amplification point. Such a sequence is complimentary to at least a portion of an amplification primer. This allows the primer to hybridize to the NPPF, and amplify the NPPF. As flanking sequences can be identical between NPPFs specific for different target nucleic acid molecules, this permits the same primer to be used to amplify any number of different NPPFs. For example, an NPPF can include a 5'-flanking sequence, and a 3'-flanking sequence, wherein the 5'- and the 3'-flanking sequences are different from one another, but are the same for a plurality of NPPFs for different targets. Thus an amplification primer that includes a sequence complementary to the 5'-flanking sequence, and an amplification primer that includes a sequence complementary to the 3'-flanking sequence, can both be used in a single reaction to amplify multiple NPPFs, even if the NPPFs are specific for different target sequences.

In some examples, the flanking sequence does not include an experiment tag sequence and/or a sequencing adapter sequence. In some examples, a flanking sequence includes or consists of an experiment tag sequence and/or sequencing adapter sequence. In other examples, the primers used to amplify the NPPFs include an experiment tag sequence and/or sequencing adapter sequence, thus permitting incorporation of the experiment tag and/or sequencing adapter into the NPPF amplicon during amplification of the NPPF.

In one example, a flanking sequence is designed such that the sequence forms a loop on itself. Thus, one region of a flanking sequence is complementary to a second region of the same flanking sequence, such that the first and second regions hybridize to one another, forming a loop or hairpin. This would eliminate the need for CFSs, as the second region would protect the first region during the nuclease step.

B. Primers that Bind the Flanking Sequences

The amplification primers that specifically bind or hybridize to the flanking sequences can be used to initiate amplification, such as PCR amplification. In addition, the amplification primers can be used to introduce nucleic acid tags (such as experiment tags or sequencing adapters) and/or detectable labels to NPPFs. For example, in addition to the amplification primer having a region complementary to the flanking sequence, it can also include a second region having a nucleic acid sequence that results in addition of an experiment tag, sequencing adapter, detectable label, or combinations thereof, to the resulting NPPF amplicon. An experiment tag or sequencing adapter can be introduced at the NPPF 5'- and/or 3'-end. In some examples, two or more experiment tags and/or sequencing adaptors are added to a single end or both ends of the NPPF amplicon, for example using a single primer having a nucleic acid sequence that results in addition of two or more experiment tags and/or sequencing adapters. Experiment tags can be used, for example, to differentiate one sample or sequence from another, or to permit capture of an NPPF amplicon by a substrate. Sequence tags permit capture of the resulting NPPF amplicon by a particular sequencing platform.

A detectable label can be introduced at any point of the NPPF, including the 5'- and/or 3'-end. In one example, the label is introduced to an NPPF amplicon by hybridization of a labeled probe complementary to the NPPF amplicon. In one example, the label is introduced to an NPPF amplicon by use of a labeled primer during amplification of the NPPF, thereby generating a labeled NPPF amplicon. Detectable labels permit detection of the NPPF amplicons.

In some examples, such primers are at least 12 nucleotides in length, such as at least 15, at least 20, at least 30, at least 40 or at least 50 nucleotides (for example 25 nucleotides). In some examples the primers include a detectable label (and such primers can be referred to as probes), such as biotin, that gets incorporated into the NPPF amplicons.

C. Addition of Experiment Tags

Experimental tags can be part of the NPPF when generated (for example be part of the flanking sequence). In another example, the experiment tag is added later, for example during amplification of the NPPF, resulting in an NPPF amplicon containing an experimental tag. The presence of the universal flanking sequences on the NPPF permit the use of universal primers, which can introduce other sequences onto the NPPFs, for example during amplification.

Experiment tags, such as one that differentiates one sample from another, can be used to identify the particular target sequence associated with the NPPF, or permit capture of an NPPF amplicon by a substrate (wherein the experiment tag is complementary to a capture probe on the substrate, permitting hybridization between the two). In one example, the experiment tag is the first three, five, ten, twenty, or thirty nucleotides of the 5'- and/or 3'-end of the NPPF or NPPF amplicon.

In one example an experiment tag is used to differentiate one sample from another. For example, such a sequence can function as a barcode, to allow one to correlate a particular sequence detected with a particular sample, patient, or experiment (such as a particular reaction well, day or set of reaction conditions). This permits a particular NPPF that is detected or sequenced to be associated with a particular patient or sample or experiment for instance. The use of such tags provides a way to lower cost per sample and increase sample throughput, as multiple NPPF amplicons can be tagged and then combined (for example from different experiments or patients), for example in a single sequencing run or detection array. This allows for the ability to combine different experimental or patient samples into a single run, within the same instrument channel. For example, such tags permitting 100's or 1,000's of different experiments to be sequenced in a single run, within a single channel. For example, pooling 100 samples per channel, 8,000 samples can be tested in a single run of an 8-channel sequencer. In addition, if the method includes the step of gel purifying the completed amplification reaction (or other method of purification or clean up that does not require actual separation) only one gel (or clean up or purification reaction or process) is needed to be run per detection or sequencing run. The sequenced NPPF amplicons can then be sorted, for example by the experiment tags.

In one example the experiment tag is used to identify the particular target sequence associated with the NPPF. In this case, using an experimental tag to correspond to a particular target sequence can shorten the time or amount of sequencing needed, as sequencing the end of the NPPF instead of the entire NPPF can be sufficient. For example, if such an experiment tag is present on the 3'-end of the NPPF amplicon, the entire NPPF amplicon sequence itself does not have to be sequenced to identify the target sequence which hybridized to the NPPF. Instead, only the 3'-end of the NPPF amplicon containing the experiment tag needs to be sequenced. This can significantly reduce sequencing time and resources, as less material needs to be sequenced.

In one example the experiment tag is used to permit capture NPPFs, such as to concentrate NPPFs or NPPF amplicons from a sample. For example, the experiment tag can have a sequence that is complementary to the sequence of at least a portion of a capture probe on a substrate surface, thereby permitting hybridization of the NPPF to the capture probe. For instance, following amplification, NPPF amplicons containing an experimental tag (such as a population of NPPF amplicons containing the same experimental tag) can be isolated from other materials by incubating the sample with a substrate (such as magnetic beads) containing a plurality of capture probes with sequences complementary to the experimental tag. After their capture, the NPPF amplicons can be detected or sequenced, or can be released from the substrate for further analysis. In one example, the substrate is magnetic beads, the PCR reaction containing NPPF amplicons is incubated with the beads. The beads are then held in a magnetic field while the sample solution (containing non-desired nucleic acid molecules and other materials) is removed. The captured NPPFs can be eluted into a smaller volume by reversing hybridization, such as by addition of base and heating. One will appreciate that similar methods can be used with other NPPFs and other substrates (such as by using a solid substrate and a flow through device), resulting in the captured NPPFs being eluted into a smaller volume. If a haptan is added during amplification, it can be used for capture. One advantage of such a method is that the NPPFs or NPPF amplicons can be isolated from a large sample, such as 1 ml plasma, and eluted into a smaller volume used for assays, such as 20 µl.

Experimental tags can also be used for amplification, such as nested amplification, or two stage amplification.

In particular examples, the experiment tag is at least 3 nucleotides in length, such as at least 5, at least 10, at least 15, at least 20, at least 25, at least 30, at least 40, or at least 50 nucleotides in length, such as 3-50, 3-20, 12-50 or 12-30 nucleotides, for example, 3, 5, 10, 20, 21, 22, 23, 24, 25, 26, 27, 28, 29 or 30 nucleotides in length.

D. Addition of Sequencing Adapters

Sequencing adapters can be part of the NPPF when generated (for example be part of the flanking sequence). In another example, the sequencing adapter is added later, for example during amplification of the NPPF, resulting in an NPPF amplicon containing a sequencing adapter. The presence of the universal flanking sequences on the NPPF permit the use of universal primers, which can introduce other sequences onto the NPPFs, for example during amplification.

A sequencing adapter can be used add a sequence to an NPPF ampilcon needed for a particular sequencing platform. For example, some sequencing platforms (such as the 454 and Illumina platforms) require the nucleic acid molecule to be sequenced to include a particular sequence at its 5'- and/or 3'-end, for example to capture the molecule to be sequenced. For example, the appropriate sequencing adapter is recognized by a complementary sequence on the sequencing chip or beads, and the NPPF captured by the presence of the sequencing adapter.

In one example, a poly-A (or poly-T), such as a poly-A or poly-T at least 10 nucleotides in length is added to the NPPF during PCR amplification. In a specific example, the poly-A (or poly-T) is added to the 3'-end of the NPPF. In some examples, this added sequence is poly-adenylated at its 3' end using a terminal deoxynucleotidyl transferase (Tdt).

In particular examples, the sequencing tag added is at least 12 nucleotides (nt) in length, such as at least 15, at least 20, at least 25, at least 30, at least 40, or at least 50 nt in length, such as 12-50 or 12-30 nt, for example, 20, 21, 22, 23, 24, 25, 26, 27, 28, 29 or 30 nt in length.

E. Detectable Labels

In some examples, the disclosed NPPFs, PCR primers, or both, include one or more detectable labels. Detectable labels are well known in the art. A detectable label is a molecule or material that can be used to produce a detectable signal that indicates the presence or concentration of an NPPF or NPPF amplicon (e.g., the bound or hybridized probe) in a sample. Thus, a labeled NPPF provides an indicator of the presence or concentration of a target nucleic acid sequence (e.g., a target DNA or a target RNA) in a sample. The disclosure is not limited to the use of particular labels, although examples are provided.

In some examples, the label is incorporated into the NPPF during synthesis of the NPPF. In some examples, the label is incorporated into the NPPF during amplification, for example using labeled primers (thus generating labeled NPPF amplicons). In yet other examples, the NPPF is labeled by using a labeled probe that is complementary to, and thus hybridizes to, a portion of the NPPF (such as an NPPF amplicon), such as a flanking region of the NPPF.

In some examples, each of the NPPFs included in a plurality of NPPFs utilized in the disclosed methods are labeled with the same detectable label. In other examples at least one NPPF is labeled with a different detectable label than at least one other NPPF in the plurality of NPPs. For example, at least one NPPF included in the plurality of NPPFs can be labeled with a fluorophore (such as Cy-3™) and at least one NPPF included in the plurality of NPPs can be labeled with a different fluorophore (such as Cy-5™). In some examples, the plurality of NPPFs can include at least 2, 3, 4, 5, 6, or more different detectable labels. Similarly, amplification primers used in the methods provided herein can be labeled with the same or different detectable labels.

A label associated with one or more nucleic acid molecules (such as an NPPF or amplification primer) can be detected either directly or indirectly. A label can be detected by any known or yet to be discovered mechanism including absorption, emission and/or scattering of a photon (including radio frequency, microwave frequency, infrared frequency, visible frequency and ultra-violet frequency photons). Detectable labels include colored, fluorescent, electroluminescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens, and paramagnetic and magnetic molecules or materials. Additional detectable labels include Raman (light scattering) labels (e.g., Nanoplex® biotags, Oxonica, Bucks, UK). Other exemplary detectable labels include digoxin, the use of energy transfer and energy quenching pairs (such as FRET), IR, and absorbance/colorimetric labels.

In non-limiting examples, NPPFs or primers are labeled with dNTPs covalently attached to hapten molecules (such as a nitro-aromatic compound (e.g., dinitrophenyl (DNP)), biotin, fluorescein, digoxigenin, etc.). Methods for conjugating haptens and other labels to dNTPs (e.g., to facilitate incorporation into labeled probes) are well known in the art. For examples of procedures, see, e.g., U.S. Pat. Nos. 5,258, 507, 4,772,691, 5,328,824, and 4,711,955. A label can be directly or indirectly attached to a dNTP at any location on the dNTP, such as a phosphate (e.g., $\alpha$, $\beta$ or $\gamma$ phosphate) or a sugar. In some examples, detection of labeled nucleic acid molecules can be accomplished by contacting the hapten-labeled NPP with a primary anti-hapten antibody. In one example, the primary anti-hapten antibody (such as a mouse anti-hapten antibody) is directly labeled with an enzyme. In another example, a secondary anti-antibody (such as a goat anti-mouse IgG antibody) conjugated to an enzyme is used for signal amplification. In other examples, the hapten is biotin and is detected by contacting the hapten-labeled NPPF with avidin or streptavidin conjugated to an enzyme, such as horseradish peroxidase (HRP) or alkaline phosphatase (AP).

Additional examples of detectable labels include fluorescent molecules (or fluorochromes). Numerous fluorochromes are known to those of skill in the art, and can be selected, for example from Life Technologies (formerly Invitrogen), e.g., see, The Handbook—A Guide to Fluorescent Probes and Labeling Technologies). Examples of particular fluorophores that can be attached (for example, chemically conjugated) to a nucleic acid molecule (such as an NPPF) are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2′7′-dimethoxy-4′5′-dichloro-6-carboxyfluorescein (JOE), fluorescein, fluorescein isothiocyanate (FITC), and QFITC (XRITC); 2′,7′-difluorofluorescein (OREGON GREEN®); fluorescamine; IR144; IR1446; Malachite Green isothiocyanate; 4-methylumbelliferone; ortho cresolphthalein; nitrotyro sine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N′,N′-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Invitrogen; Molecular Probes (Eugene, Oreg.)) and including the ALEXA FLUOR® series of dyes (for example, as described in U.S. Pat. Nos. 5,696,157, 6,130,101 and 6,716,979), the BODIPY series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT™ (obtained, for example, from Life Technologies (QuantumDot Corp, Invitrogen Nanocrystal Technologies, Eugene, Oreg.); see also, U.S. Pat. Nos. 6,815,064; 6,682,596; and 6,649,138). Semiconductor nanocrystals are microscopic particles having size-dependent optical and/or electrical properties. When semiconductor nanocrystals are illuminated with a primary energy source, a secondary emission of energy occurs of a frequency that corresponds to the bandgap of the semiconductor material used in the semiconductor nanocrystal. This emission can be detected as colored light of a specific wavelength or fluorescence. Semiconductor nanocrystals with different spectral characteristics are described in e.g., U.S. Pat. No. 6,602,671. Semiconductor nanocrystals that can be coupled to a variety of biological molecules (including dNTPs and/or nucleic acids) or substrates by techniques described in, for example, Bruchez et al., *Science* 281:2013-2016, 1998; Chan et al., *Science* 281:2016-2018, 1998; and U.S. Pat. No. 6,274,323.

Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. 99/26299 (published May 27, 1999). Separate populations of semiconductor nanocrystals can be produced that are identifiable based on their different spectral characteristics. For example, semiconductor nanocrystals can be produced that emit light of different colors based on their composition, size or size and composition. For example, quantum dots that emit light at different wavelengths based on size (565 nm, 655 nm, 705 nm, or 800 nm emission wavelengths), which are suitable as fluorescent labels in the probes disclosed herein are available from Life Technologies (Carlsbad, Calif.).

Additional labels include, for example, radioisotopes (such as $^3$H), metal chelates such as DOTA and DPTA chelates of radioactive or paramagnetic metal ions like $Gd^{3+}$, and liposomes.

Detectable labels that can be used with nucleic acid molecules (such as an NPPF or amplification primer) also include enzymes, for example HRP, AP, acid phosphatase, glucose oxidase, β-galactosidase, β-glucuronidase, or β-lactamase. Where the detectable label includes an enzyme, a chromogen, fluorogenic compound, or luminogenic compound can be used in combination with the enzyme to generate a detectable signal (numerous of such compounds are commercially available, for example, from Life Technologies, Carlsbad, Calif.). Particular examples of chromogenic compounds include diaminobenzidine (DAB), 4-nitrophenylphosphate (pNPP), fast red, fast blue, bromochloroindolyl phosphate (BCIP), nitro blue tetrazolium (NBT), BCIP/NBT, AP Orange, AP blue, tetramethylbenzidine (TMB), 2,2′-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet.

Alternatively, an enzyme can be used in a metallographic detection scheme. Metallographic detection methods include using an enzyme, such as alkaline phosphatase, in combination with a water-soluble metal ion and a redox-inactive substrate of the enzyme. The substrate is converted to a redox-active agent by the enzyme, and the redox-active agent reduces the metal ion, causing it to form a detectable precipitate. (See, for example, U.S. Patent Application Publication No. 2005/0100976, PCT Publication No. 2005/003777 and U.S. Patent Application Publication No. 2004/0265922). Metallographic detection methods also include using an oxido-reductase enzyme (such as horseradish peroxidase) along with a water soluble metal ion, an oxidizing agent and a reducing agent, again to form a detectable precipitate. (See, for example, U.S. Pat. No. 6,670,113).

In some embodiments, the detectable label is attached to or incorporated in the NPPF or primer at the 5′ end or the 3′ end (e.g., the NPPF or primer is an end-labeled probe). In other examples the detectable label is incorporated in the NPPF or primer at an internal position, such as 1, 2, 3, 4, 5, 6, 7, 8, 9, 10, 11, 12, 13, 14, 15, or more bases from the 5′ end of the NPPF or primer, or 1, 2, 3, 4, 5, 6, 7, 8, 9, 10, 11, 12, 13, 14, 15, or more bases from the 3′ end of the NPPF or primer.

In one example, one of the flanking regions of the NPPF contains an acceptor or emitter (such as an acceptor fluorophore), while the amplification primer complementary to the flanking region contains the converse (such as a donor fluorophore). Thus the primer-NPPF duplex emits detectable signal, but single stranded primers, or single stranded NPPFs, do not. The appearance of signal is a measure of the amount of NPPF in the sample, and can be measured without separation of the labeled excess primers from the amplified adducts. Examples of FRET acceptor-donor pairs are known in the art and can include FAM as a donor fluorophore for use with JOE, TAMRA, and ROX, 3-($\epsilon$-carboxy-pentyl)-3'-ethyl-5,5'-dimethyloxacarbocyanine (CYA) can serve as a donor fluorophore for rhodamine derivatives (such as R6G, TAMRA, and ROX) which can be used as acceptor fluorophores. Grant et al. (*Biosens Bioelectron.* 16:231-7, 2001) provide particular examples of FRET pairs that can be used in the methods disclosed herein.

V. Samples

A sample is any collective comprising one or more targets, such as a biological sample or biological specimen. The sample can be collected or obtained using methods well known to those ordinarily skilled in the art The samples of use in the disclosed methods can include any specimen that includes nucleic acid (such as genomic DNA, cDNA, viral DNA or RNA, rRNA, tRNA, mRNA, miRNA, oligonucleotides, nucleic acid fragments, modified nucleic acids, synthetic nucleic acids, or the like). In one example, the sample includes unstable RNA. In some examples, the nucleic acid molecule to be detected or sequenced is cross-linked in the sample (such as a cross-linked DNA, mRNA, miRNA, or vRNA) or is soluble in the sample. In some examples, the sample is a fixed sample, such as a sample that includes an agent that causes target molecule cross-linking. In some examples, the target nucleic acid in the sample is not extracted, solubilized, or both, prior to detecting or sequencing the target nucleic acid molecule.

In some examples, the disclosed methods include obtaining the sample prior to analysis of the sample. In some examples, the disclosed methods include selecting a subject having a tumor, and then in some examples further selecting one or more target DNAs or RNAs to detect based on the subject's tumor, for example, to determine a diagnosis or prognosis for the subject or for selection of one or more therapies. In some examples, nucleic acid molecules in a sample to be analyzed are first isolated, extracted, concentrated, or combinations thereof, from the sample.

In some examples, RNA in the sample reverse transcribed prior to performing the methods provided herein. However, the disclosed methods do not require reverse transcription, as the target RNA sequence is effectively converted into a complementary probe sequence through hybridization and nuclease activity. It is sometimes desirable to sequence RNA molecules rather than the gene sequences which encode the RNA, since RNA molecules are not necessarily co-linear with their DNA template. And some organisms are RNA, such as RNA viruses.

In some examples, the sample is lysed. The lysis buffer is designed to inactivate enzymes and prevent the degradation of RNA, but after a limited dilution into a hybridization dilution buffer it permits nuclease activity and facilitates hybridization with stringent specificity. A dilution buffer can be added to neutralize the inhibitory activity of the lysis and other buffers, such as inhibitory activity for other enzymes (e.g., polymerase). Alternatively, the composition of the lysis buffer and other buffers can be changed to a composition that is tolerated, for example by a polymerase.

In some examples, the methods include analyzing a plurality of samples simultaneously or contemporaneously. For example, the methods can analyze at least two different samples (for example from different patients) simultaneously or contemporaneously. In one example, the methods can detect or sequence at least two different target nucleic acid molecules (such as 2, 3, 4, 5, 6, 7, 8, 9 or 10 different targets) in at least two different samples (such as at least 5, at least 10, at least 100, at least 500, at least 1000, or at least 10,000 different samples) simultaneously or contemporaneously.

Exemplary samples include, without limitation, cells, cell lysates, blood smears, cytocentrifuge preparations, cytology smears, bodily fluids (e.g., blood and fractions thereof such as serum and plasma, saliva, sputum, urine, spinal fluid, gastric fluid, sweat, semen, etc.), cytological smears, buccal cells, extracts of tissues, cells or organs, tissue biopsies (e.g., tumor biopsies), fine-needle aspirates, punch biopsies, circulating tumor cells, fresh tissue, frozen tissue, fixed tissue, fixed and wax- (e.g., paraffin-)embedded tissue, bone marrow, and/or tissue sections (e.g., cryostat tissue sections and/or paraffin-embedded tissue sections). The biological sample may also be a laboratory research sample such as a cell culture sample or supernatant.

Methods of obtaining a sample from a subject are known in the art. For example, methods of obtaining tissue or cell samples are routine. Exemplary samples may be obtained from normal cells or tissues, or from neoplastic cells or tissues. Neoplasia is a biological condition in which one or more cells have undergone characteristic anaplasia with loss of differentiation, increased rate of growth, invasion of surrounding tissue, and which cells may be capable of metastasis. In particular examples, a biological sample includes a tumor sample, such as a sample containing neoplastic cells.

Exemplary neoplastic cells or tissues may be included in or isolated from solid tumors, including lung cancer (e.g., non-small cell lung cancer, such as lung squamous cell carcinoma), breast carcinomas (e.g. lobular and duct carcinomas), adrenocortical cancer, ameloblastoma, ampullary cancer, bladder cancer, bone cancer, cervical cancer, cholangioma, colorectal cancer, endometrial cancer, esophageal cancer, gastric cancer, glioma, granular call tumor, head and neck cancer, hepatocellular cancer, hydatiform mole, lymphoma, melanoma, mesothelioma, myeloma, neuroblastoma, oral cancer, osteochondroma, osteosarcoma, ovarian cancer, pancreatic cancer, pilomatricoma, prostate cancer, renal cell cancer, salivary gland tumor, soft tissue tumors, Spitz nevus, squamous cell cancer, teratoid cancer, and thyroid cancer. Exemplary neoplastic cells may also be included in or isolated from hematological cancers including leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia.

For example, a sample from a tumor that contains cellular material can be obtained by surgical excision of all or part of the tumor, by collecting a fine needle aspirate from the tumor, as well as other methods known in the art. In some examples, a tissue or cell sample is applied to a substrate and analyzed to determine presence of one or more target DNAs or RNAs. A solid support useful in a disclosed method need only bear the biological sample and, optionally, permit the convenient detection of components (e.g., proteins and/or nucleic acid sequences) in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE™ chips.

The disclosed methods are sensitive and specific and allow detection of target nucleic acid molecules in a sample containing even a limited number of cells. Samples that include small numbers of cells, such as less than 250,000 cells (for example less than 100,000, less than 50,000, less than 10,000, less than 1,000, less than 500, less than 200, less than 100 cells, or less than 10 cells, include but are not limited to, FFPE samples, fine needle aspirates (such as those from lung, prostate, lymph, breast, or liver), punch biopsies, needle biopsies, small populations of (e.g., FACS) sorted cells or circulating tumor cells, lung aspirates, small numbers of laser captured or macrodissected cells or circulating tumor cells, exosomes and other subcellular particles, or body fluids (such as plasma, serum, spinal fluid, saliva, and breast aspirates). For example, a target DNA or target RNA can be detected in as few as 1000 cells (such as a sample including 1000 or more cells, such as 1000, 2000, 3000, 4000, 5000, 6000, 7000, 8000, 9000, 10,000, 15,000, 20,000, 50,000, or more cells). In some examples, expression of a target DNA or target RNA can be detected in about 1000 to 100,000 cells, for example about 1000 to 50,000, 1000 to 15,000, 1000 to 10,000, 1000 to 5000, 3000 to 50,000, 6000 to 30,000, or 10,000 to 50,000 cells). In some examples, expression of a target DNA or target RNA can be detected in about 100 to 250,000 cells, for example about 100 to 100,000, 100 to 50,000, 100 to 10,000, 100 to 5000, 100 to 500, 100 to 200, or 100 to 150 cells. In other examples, expression of a target DNA or target RNA can be detected in about 1 to 1000 cells (such as about 1 to 500 cells, about 1 to 250 cells, about 1 to 100 cells, about 1 to 50 cells, about 1 to 25 cells, or about 1 cell).

Samples may be treated in a number of ways known to those of ordinary skill in the art prior to (or contemporaneous with) contacting the sample with a target-specific reagent (such as a NPPF). One relatively simple treatment is suspension of the sample in a buffer, e.g., lysis buffer, which conserves all components of the sample in a single solution. Many traditional methods for detecting targets require more complex sample processing (e.g., involving multiple steps and/or various types of specialized instruments) to make the target accessible to a target-specific reagent(s). For example, certain detection methods require partial or complete isolation (e.g., extraction) of a target (e.g., DNA or mRNA) from the sample. A target (such as, DNA or RNA) has been isolated or extracted when it is purified away from other non-target biological components in a sample. Purification refers to separating the target from one or more extraneous components also found in a sample. For example, prior to PCR-based detection of mRNA with paired target-specific primers, total or soluble mRNA (including the target mRNA) often is separated from cell proteins and other nucleic acids in the sample. Components that are isolated, extracted or purified from a mixed specimen or sample typically are enriched by at least 50%, at least 60%, at least 75%, at least 90%, or at least 98% or even at least 99% compared to the unpurified or non-extracted sample.

Isolation of biological components from a sample is time consuming and bears the risk of loss of the component that is being isolated, e.g., by degradation and/or poor efficiency or incompleteness of the process(es) used for isolation. Moreover, with some samples, such as fixed tissues, targets (such as DNA or RNA (e.g., mRNA or miRNA)) are notoriously difficult to isolate with high fidelity (e.g., as compared to fresh or frozen tissues) because, it is thought that, at least some proportion of the targets are cross-linked to other components in the fixed sample and, therefore, cannot be readily isolated or solubilized and may be lost upon separation of soluble and insoluble fractions. Accordingly, in some examples, methods of detecting a target nucleic acid do not require or involve purification, extraction or isolation of a target from a sample prior to contacting the sample with one or more NPPFs, and/or involve only suspending the sample in a solution, e.g., lysis buffer, that retains all components of the sample prior to contacting the sample with a target-specific reagent.

In some examples, cells in the sample are lysed or permeabilized in an aqueous solution (for example using a lysis buffer). The aqueous solution or lysis buffer includes detergent (such as sodium dodecyl sulfate) and one or more chaotropic agents (such as formamide, guanidinium HCl, guanidinium isothiocyanate, or urea). The solution may also contain a buffer (for example SSC). In some examples, the lysis buffer includes about 15% to 25% formamide (v/v) about 0.01% to 0.1% SDS, and about 0.5-6×SSC (for example, about 3×SSC). The buffer may optionally include tRNA (for example, about 0.001 to about 2.0 mg/ml) or a ribonuclease; DNAase; proteinase K; enzymes (e.g. collagenase or lipase) that degrade protein, matrix, carbohydrate, lipids, or one species of oligonucleotides, or combinations thereof. The lysis buffer may also include a pH indicator, such as Phenol Red. In a particular example, the lysis buffer includes 20% formamide, 3×SSC (79.5%), 0.05% SDS, 1 µg/ml tRNA, and 1 mg/ml Phenol Red. Cells are incubated in the aqueous solution (optionally overlayed with oil to prevent evaporation or to serve as a sink for paraffin) for a sufficient period of time (such as about 1 minute to about 60 minutes, for example about 5 minutes to about 20 minutes, or about 10 minutes) and at a sufficient temperature (such as about 22° C. to about 110° C., for example, about 80° C. to about 105° C., about 37° C. to about 105° C., or about 90° C. to about 100° C.) to lyse or permeabilize the cell. In some examples, lysis is performed at about 95° C. In some examples, the lysis step includes incubating the sample at about 95° C. for about 5-15 minutes to denature RNA in the sample, but not genomic DNA. In other examples, the lysis step includes incubating the sample at about 105° C. for about 5-15 minutes to denature both RNA and genomic DNA in the sample. In one example Proteinase K is included with the lysis buffer.

In some examples, the crude cell lysis is used directly without further purification. The cells may be lysed in the presence or absence of one or more of the disclosed NPPFs. If the cells are lysed in the absence of probe, the one or more probes can be subsequently added to the crude lysate. In other examples, nucleic acids (such as DNA and/or RNA) are isolated from the cell lysate prior to contacting the lysate prior to contacting with one or more NPPFs.

In other examples, tissue samples are prepared by fixing and embedding the tissue in a medium or include a cell suspension is prepared as a monolayer on a solid support (such as a glass slide), for example by smearing or centrifuging cells onto the solid support. In further examples, fresh frozen (for example, unfixed) tissue or tissue sections may be used in the methods disclosed herein. In particular examples, FFPE tissue sections are used in the disclosed methods.

In some examples an embedding medium is used. An embedding medium is an inert material in which tissues and/or cells are embedded to help preserve them for future analysis. Embedding also enables tissue samples to be sliced into thin sections. Embedding media include paraffin, celloidin, OCT™ compound, agar, plastics, or acrylics. Many embedding media are hydrophobic; therefore, the inert material may need to be removed prior to analysis, which utilizes primarily hydrophilic reagents. The term deparaffinization or dewaxing is broadly used herein to refer to the partial or complete removal of any type of embedding medium from a biological sample. For example, paraffin-embedded tissue sections are dewaxed by passage through organic solvents, such as toluene, xylene, limonene, or other suitable solvents. In other examples, paraffin-embedded tissue sections are utilized directly (e.g., without a dewaxing step).

Tissues can be fixed by any suitable process, including perfusion or by submersion in a fixative. Fixatives can be classified as cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation). Additives may also be included in the fixative, such as buffers, detergents, tannic acid, phenol, metal salts (such as zinc chloride, zinc sulfate, and lithium salts), and lanthanum.

The most commonly used fixative in preparing tissue or cell samples is formaldehyde, generally in the form of a formalin solution (4% formaldehyde in a buffer solution, referred to as 10% buffered formalin). In one example, the fixative is 10% neutral buffered formalin, and thus in some examples the sample is formalin fixed.

In some examples, the sample is an environmental sample (such as a soil, air, or water sample, or a sample obtained from a surface (for example by swabbing)), or a food sample (such as a vegetable, fruit, dairy or meat containing sample) for example to detect pathogens that may be present.

VI. Target Nucleic Acids

A target nucleic acid molecule is a nucleic acid molecule that is capable of detection, or of interest, or useful to detect with the disclosed methods. Targets include single-, double- or other multiple-stranded nucleic acid molecules (such as, DNA (e.g., genomic, mitochondrial, or synthetic), RNA (such as mRNA, miRNA, tRNA, siRNA, long non-coding (nc) RNA, biologically occurring anti-sense RNA, Piwi-interacting RNAs (piRNAs), or small nucleolar RNAs (snoRNAs)), whether from eukaryotes, prokaryotes, viruses, fungi, bacteria or other biological organism. Genomic DNA targets may include one or several parts of the genome, such as coding regions (e.g., genes or exons), non-coding regions (whether having known or unknown biological function, e.g., enhancers, promoters, regulatory regions, telomeres, or "nonsense" DNA). In some embodiments, a target may contain or be the result of a mutation (e.g., germ line or somatic mutation) that may be naturally occurring or otherwise induced (e.g., chemically or radiation-induced mutation). Such mutations may include (or result from) genomic rearrangements (such as translocations, insertions, deletions, or inversions), single nucleotide variations, and/or genomic amplifications. In some embodiments, a target may contain one or more modified or synthetic monomers units (e.g., peptide nucleic acid (PNA), locked nucleic acid (LNA), methylated nucleic acid, post-translationally modified amino acid, cross-linked nucleic acid or cross-linked amino acid).

The portion of a target nucleic acid molecule to which a NPPF may specifically bind also may be referred to as "target," again, as context dictates, but more specifically may be referred to as target portion, complementary region (CR), target site, protected target region or protected site, or similar. A NPPF specifically bound to its complementary region forms a complex, which complex may remain integrated with the target as a whole and/or sample, or be separate (or be or become separated) from the target as a whole and/or the sample. In some embodiments, a NPPF/CR complex is separated (or becomes disassociated) from the target as a whole and/or the sample, e.g., by the action of a nuclease, such as S1 nuclease.

All types of target nucleic acid molecules can be analyzed using the disclosed methods. In one example, the target is a ribonucleic acid (RNA) molecule, such as a messenger RNA (mRNA), a ribosomal RNA (rRNA), a transfer RNA (tRNA), micro RNA (miRNA), an siRNA, anti-sense RNA, or a viral RNA (vRNA). In another example, the target is a deoxyribonucleic (DNA) molecule, such as genomic DNA (gDNA), mitochondrial DNA (mtDNA), chloroplast DNA (cpDNA), viral DNA (vDNA), cDNA, or a transfected DNA. In a specific example, the target is an antisense nucleotide. In some examples, the whole transcriptome of a cell or a tissue can be analyzed using the disclosed methods. In one example, the target nucleic acid molecule is a rare nucleic acid molecule, for example only appearing less than about 100,000 times, less than about 10,000 times, less than about 5,000 times, less than about 100 times, less than 10 times, or only once in the sample, such as a nucleic acid molecule only appearing 1 to 10,000, 1 to 5,000, 1 to 100 or 1 to 10 times in the sample).

A plurality of targets can be detected or sequenced in the same sample or assay, or even in multiple samples or assays, for example simultaneously or contemporaneously. Similarly, a single target can be detected or sequenced in a plurality of samples, for example simultaneously or contemporaneously. In one example the target nucleic acid molecule is an miRNA and an mRNA. Thus, in such an example, the method would include the use of at least one NPPF specific for the miRNA and at least one NPPF specific for the mRNA. In one example the target nucleic acid molecules are two different DNA molecules. Thus, in such an example, the method would include the use of at least one NPPF specific for the first target DNA and at least one NPPF specific for the second target DNA. In one example the target nucleic acid molecules are two different RNA molecules. Thus, in such an example, the method would include the use of at least one NPPF specific for the first target RNA and at least one NPPF specific for the second target RNA.

In some examples, the disclosed methods permit detection or sequencing of DNA or RNA single nucleotide polymorphisms (SNPs) or variants (sNPVs), splice junctions, methylated DNA, gene fusions or other mutations, protein-bound DNA or RNA, and also cDNA, as well as levels of expression (such as DNA or RNA expression, such as cDNA expression, mRNA expression, miRNA expression, rRNA expression, siRNA expression, or tRNA expression). Any nucleic acid molecule to which a nuclease protection probe can be designed to hybridize can be quantified and identified by the disclosed methods, even though the target nucleic acid molecules themselves need not be sequenced and are even in some examples destroyed.

In one example, DNA methylation is detected by using an NPPF that includes a base mis-match at the site where methylation has or has not occurred, such that upon treatment of the target sample, methylated bases are converted to a different base, complementary to the base in the NPPF.

One skilled in the art will appreciate that the target can include natural or unnatural bases, or combinations thereof.

In specific non-limiting examples, a target nucleic acid (such as a target DNA or target RNA) associated with a neoplasm (for example, a cancer) is selected. Numerous chromosome abnormalities (including translocations and other rearrangements, reduplication or deletion) or mutations have been identified in neoplastic cells, especially in cancer cells, such as B cell and T cell leukemias, lymphomas, breast cancer, colon cancer, neurological cancers and the like.

In some examples, a target nucleic acid molecule includes GAPDH (e.g., GenBank Accession No. NM_002046), PPIA (e.g., GenBank Accession No. NM_021130), RPLP0 (e.g., GenBank Accession Nos. NM_001002 or NM_053275), RPL19 (e.g., GenBank Accession No. NM_000981), ZEB1 (e.g., GenBank Accession No. NM_030751), Zeb2 (e.g., GenBank Accession Nos. NM_001171653 or NM_014795), CDH1 (e.g., GenBank Accession No. NM_004360), CDH2 (e.g., GenBank Accession No. NM_007664), VIM (e.g., GenBank Accession No. NM_003380), ACTA2 (e.g., GenBank Accession No. NM_001141945 or NM_001613), CTNNB1 (e.g., GenBank Accession No. NM_001904, NM_001098209, or NM_001098210), KRT8 (e.g., GenBank Accession No. NM_002273), SNAI1 (e.g., GenBank Accession No. NM_005985), SNAI2 (e.g., GenBank Accession No. NM_003068), TWIST1 (e.g., GenBank Accession No. NM_000474), CD44 (e.g., GenBank Accession No. NM_000610, NM_001001389, NM_00100390, NM_001202555, NM_001001391, NM_001202556, NM_001001392, NM_001202557), CD24 (e.g., GenBank Accession No. NM_013230), FN1 (e.g., GenBank Accession No. NM_212474, NM_212476, NM_212478, NM_002026, NM_212482, NM_054034), IL6 (e.g., GenBank Accession No. NM_000600), MYC (e.g., GenBank Accession No. NM_002467), VEGFA (e.g., GenBank Accession No. NM_001025366, NM_001171623, NM_003376, NM_001171624, NM_001204384, NM_001204385, NM_001025367, NM_001171625, NM_001025368, NM_001171626, NM_001033756, NM_001171627, NM_001025370, NM_001171628, NM_001171622, NM_001171630), HIF1A (e.g., GenBank Accession No. NM_001530, NM_181054), EPAS1 (e.g., GenBank Accession No. NM_001430), ESR2 (e.g., GenBank Accession No. NM_001040276, NM_001040275, NM_001214902, NM_001437, NM_001214903), PRKCE (e.g., GenBank Accession No. NM_005400), EZH2 (e.g., GenBank Accession No. NM_001203248, NM_152998, NM_001203247, NM_004456, NM_001203247), DAB2IP (e.g., GenBank Accession No. NM_032552, NM_138709), B2M (e.g., GenBank Accession No. NM_004048), and SDHA (e.g., GenBank Accession No. NM_004168).

In some examples, a target miRNA includes hsa-miR-205 (MIR205, e.g., GenBank Accession No. NR_029622), hsa-miR-324 (MIR324, e.g., GenBank Accession No. NR_029896), hsa-miR-301a (MIR301A, e.g., GenBank Accession No. NR_029842), hsa-miR-106b (MIR106B, e.g., GenBank Accession No. NR_029831), hsa-miR-877 (MIR877, e.g., GenBank Accession No. NR_030615), hsa-miR-339 (MIR339, e.g., GenBank Accession No. NR_029898), hsa-miR-10b (MIR10B, e.g., GenBank Accession No. NR_029609), hsa-miR-185 (MIR185, e.g., GenBank Accession No. NR_029706), hsa-miR-27b (MIR27B, e.g., GenBank Accession No. NR_029665), hsa-miR-492 (MIR492, e.g., GenBank Accession No. NR_030171), hsa-miR-146a (MIR146A, e.g., GenBank Accession No. NR_029701), hsa-miR-200a (MIR200A, e.g., GenBank Accession No. NR_029834), hsa-miR-30c (e.g., GenBank Accession No. NR_029833, NR_029598), hsa-miR-29c (MIR29C, e.g., GenBank Accession No. NR_029832), hsa-miR-191 (MIR191, e.g., GenBank Accession No. NR_029690), or hsa-miR-655 (MIR655, e.g., GenBank Accession No. NR_030391).

In one example the target is a pathogen nucleic acid, such as viral RNA or DNA. Exemplary pathogens include, but are not limited to, viruses, bacteria, fungi, and protozoa. In one example, the target is a viral RNA. Viruses include positive-strand RNA viruses and negative-strand RNA viruses. Exemplary positive-strand RNA viruses include, but are not limited to: Picornaviruses (such as Aphthoviridae [for example foot-and-mouth-disease virus (FMDV)]), Cardioviridae; Enteroviridae (such as Coxsackie viruses, Echoviruses, Enteroviruses, and Polioviruses); Rhinoviridae (Rhinoviruses)); Hepataviridae (Hepatitis A viruses); Togaviruses (examples of which include rubella; alphaviruses (such as Western equine encephalitis virus, Eastern equine encephalitis virus, and Venezuelan equine encephalitis virus)); Flaviviruses (examples of which include Dengue virus, West Nile virus, and Japanese encephalitis virus); and Coronaviruses (examples of which include SARS coronaviruses, such as the Urbani strain). Exemplary negative-strand RNA viruses include, but are not limited to: Orthomyxoviruses (such as the influenza virus), Rhabdoviruses (such as Rabies virus), and Paramyxoviruses (examples of which include measles virus, respiratory syncytial virus, and parainfluenza viruses). In one example the target is viral DNA from a DNA virus, such as Herpesviruses (such as Varicella-zoster virus, for example the Oka strain; cytomegalovirus; and Herpes simplex virus (HSV) types 1 and 2), Adenoviruses (such as Adenovirus type 1 and Adenovirus type 41), Poxviruses (such as Vaccinia virus), and Parvoviruses (such as Parvovirus B19). In another example, the target is a retroviral nucleic acid, such as one from human immunodeficiency virus type 1 (HIV-1), such as subtype C, HIV-2; equine infectious anemia virus; feline immunodeficiency virus (FIV); feline leukemia viruses (FeLV); simian immunodeficiency virus (SW); and avian sarcoma virus. In one example, the target nucleic acid is a bacterial nucleic acid. In one example the bacterial nucleic acid is from a gram-negative bacteria, such as *Escherichia coli* (K-12 and O157:H7), *Shigella dysenteriae*, and *Vibrio cholerae*. In another example the bacterial nucleic acid is from a gram-positive bacteria, such as *Bacillus anthracis, Staphylococcus aureus*, pneumococcus, gonococcus, and streptococcal meningitis. In one example, the target nucleic acid is a nucleic acid from protozoa, nemotodes, or fungi.

Exemplary protozoa include, but are not limited to, *Plasmodium, Leishmania, Acanthamoeba, Giardia, Entamoeba, Cryptosporidium, Isospora, Balantidium, Trichomonas, Trypanosoma, Naegleria*, and *Toxoplasma*. Exemplary fungi include, but are not limited to, *Coccidiodes immitis* and *Blastomyces dermatitidis*.

One of skill in the art can identify additional target DNAs or RNAs and/or additional target miRNAs which can be detected utilizing the methods disclosed herein.

VII. Assay Output

In some embodiments, the disclosed methods include determining presence or an amount of one or more target nucleic acid molecules in a sample. In other or additional embodiments, the disclosed methods include determining the sequence of one or more target nucleic acid molecules in a sample, which can include quantification of sequences detected. The results of the methods can be provided to a user (such as a scientist, clinician or other health care worker, laboratory personnel, or patient) in a perceivable output that provides information about the results of the test. In some examples, the output can be a paper output (for example, a written or printed output), a display on a screen, a graphical output (for example, a graph, chart, or other diagram), or an audible output. In one example, the output is a table or graph including a qualitative or quantitative indicator of presence or amount (such as a normalized amount) of a target nucleic acid molecule detected (or not detected) in the sample. In other examples the output is a map or image of signal present on a substrate (for example, a digital image of fluorescence from an array). In other examples, the embodiments, the output is the sequence of one or more target nucleic acid molecules in a sample, such a report indicting the presence of a particular mutation in the target molecule.

In some examples, the output is a numerical value, such as an amount of a target nucleic acid molecule in a sample. In additional examples, the output is a graphical representation, for example, a graph that indicates the value (such as amount or relative amount) of a target nucleic acid molecule in the sample on a standard curve. In additional examples, the output is a graphical representation, for example, a graph that indicates the sequence of a target nucleic acid molecule in the sample (for example which might indicate where a mutation is present). In some examples, the output is communicated to the user, for example by providing an output via physical, audible, or electronic means (for example by mail, telephone, facsimile transmission, email, or communication to an electronic medical record).

The output can provide quantitative information (for example, an amount of a particular target nucleic acid molecule or an amount of a particular target nucleic acid molecule relative to a control sample or value) or can provide qualitative information (for example, a determination of presence or absence of a particular target nucleic acid molecule). In additional examples, the output can provide qualitative information regarding the relative amount of a target nucleic acid molecule in the sample, such as identifying an increase or decrease relative to a control or no change relative to a control.

As discussed herein the NPPF amplicons can include one or more experiment tags, which can be used for example to identify a particular patient, sample, experiment, or target sequence. The use of such tags permits the detected or sequenced NPPF amplicon to be "sorted" or even counted, and thus permits analysis of multiple different samples (for example from different patients), multiple different targets (for example at least two different nucleic acid targets), or combinations thereof, in a single reaction. In one example, Illumina and Bowtie software can be used for such analysis.

In one example, the NPPFs include an experiment tag unique for each different target nucleic acid molecule. The use of such a tag allows one to merely sequence or detect this tag, without sequencing the entire NPPF, to identify the NPPF as corresponding to a particular nucleic acid target. In addition, if multiple nucleic acid targets are to be analyzed, the use of a unique experiment tag for each target simplifies the analysis, as each detected or sequenced experiment tag can be sorted, and if desired counted. This permits for quantification of the target nucleic acid that was in the sample, as the NPPF amplicons are in stoichiometric proportion to the target in the sample. For example if multiple target nucleic acids are detected or sequenced in a sample, the methods permit the generation of a table or graph showing each target sequence and the number of copies detected or sequenced, by simply detecting or sequencing and then sorting the experimental tag.

In another example, the NPPFs include an experiment tag unique for each different sample (such as a unique tag for each patient sample). The use of such a tag allows one to associate a particular detected NPPF amplicon with a particular sample. Thus, if multiple samples are analyzed in the same reaction (such as the same well or same sequencing reaction), the use of a unique experiment tag for each sample simplifies the analysis, as each detected or sequenced NPPF can be associated with a particular sample. For example if a target nucleic acid is detected or sequenced in samples, the methods permit the generation of a table or graph showing the result of the analysis for each sample.

One skilled in the art will appreciate that each NPPF amplicon can include a plurality of experiment tags (such as at least 2, 3, 4, 5, 6, 7, 8, 9 or 10 experiment tags), such as a tag representing the target sequence, and another representing the sample. Once each tag is detected or sequenced, appropriate software can be used to sort the data in any desired format, such as a graph or table. For example, this permits analysis of multiple target sequences in multiple samples simultaneously or contemporaneously.

In some examples, the detected or sequenced NPPF amplicon is compared to a reference database of known sequences for each target nucleic acid sequence. In some examples, such a comparison permits detection of mutations, such as SNPs. In some examples, such a comparison permits for a comparison of a reference NPPF's abundance to the abundance of an NPPF probe in a region known to contain SNP's.

The disclosure is further illustrated by the following non-limiting Examples.

EXAMPLE 1

Simultaneous Sequencing of a Plurality of NPPFs

This example describes methods used to generate and sequence NPPFs.

Seven different NPPFs were generated. Each NPPF included a region that was specific for a particular target nucleic acid molecule 25 nucleotides in length with a median Tm of 62° C., as well as flanking sequences on both ends. Although the 5'- and 3'-flanking sequences differed, they were the same for each of the seven different NPPFs. The 5'-flanking sequence was 25 nucleotides with a Tm of 61° C. and the 3'-flanking sequence was 25 nucleotides with a Tm of 63° C.

The seven different NPPFs were pooled at known ratios (1:1.5:2:4:5) and PCR amplified as follows. The NPPFs were incubated with PCR primers. One primer included a sequence that was complementary to the 5'-flanking sequence and the second primer included a sequence that was complementary to the 3'-flanking sequence. The second primer also included a sequence to allow for incorporation of a six nucleotide experiment tag into the resulting amplicon, so that each NPPF amplified using this primer had the same six nucleotide experiment tag. Several such reactions were carried out, each with a different tag. The first primer was 49 bases in length. Twenty of these bases were identical to the 5'-flanking sequence. These 20 bases had a Tm of 54° C. and the overall Tm of the entire primer was 70° C. The second primer complementary to the 3'-flanking sequence was 57 nucleotides total with a Tm of about 70° C. The first 19 nucleotides of the second primer were exactly complementary to the 3'-flanking region and had a Tm of 54° C.

Eight separate PCR reactions were run, so that variances could be identified. The resulting amplicons were cleaned up using either gel purification or standard column-based purification (Qiagen QIAQuick spin columns). The amplicons containing the NPPF and an experimental tag were then sequenced using Illumina platform. Each amplicon sequenced was sorted based on the experiment tag sequence—each tag represented one replicate pool of the seven NPPFs. Within each experiment tag group, the number of amplicons identified for each of the seven tags was counted.

128 million amplicons were sequenced, and of those, 110 million (87%) resulted in a perfectly sequenced experiment tag. The amplicons were compared to the expected sequences using Bowtie, resulting in about 80% prefect-match sequences. This is a good percentage of perfect-match sequences for the Illumina system, based on their published error and quality specs. FIG. 5 shows the number of amplicons detected for each of the seven unique NPPFs corresponding to the original ratio of NPPF pooled prior to PCR. The probes were measured in eight separate experiments, each of which had a different experimental tag added during amplification. These were all pooled into a single channel of the sequencer and sequenced. The error bars indicate the reproducibility (1 SD) of the eight experiments FIG. 6, a replot of the data shown in FIG. 5, shows the eight individual experimental results for each probe, the average (without error bars, same average as depicted in FIG. 5 with error bars), and the expected (based on the amount of NPPF added to the sample). The ratios observed for each of the seven NPPFs matched those expected (based on the original amount of NPPF added to the PCR reaction).

EXAMPLE 2

Simultaneous Detection of a Plurality of NPPFs

This example describes methods used to generate and detect NPPFs using an array, and quantification of the degree of amplification achieved.

Three different NPPFs were generated (one containing a sequence complementary to the human BAX gene, one containing an EML4-ALK fusion gene complementary sequence, and one containing an EML4 complementary sequence). Thus, each NPPF included a region that was specific for a particular target nucleic acid molecule, as well as flanking sequences on both ends. The 5'-end of each NPPF had a biotin label. The NPPFs were 25 nucleotides, having a Tm of 63° C. to 65° C. Although the 5'- and 3'-flanking sequences differed, they were the same for each of the seven different NPPFs. The 5'-flanking sequence was 25 nucleotides with a Tm of 61° C. and the 3'-flanking sequence was 25 nucleotides with a Tm of 63° C.

In one experiment, the unamplified NPPFs were hybridized to an array following qNPA. The array included an anchor probe bound to bifunctional linkers. One half of the bifunctional linker is complementary to the anchor, and the other half is complementary to the gene-specific part of the NPPF. The linker thus forms a bridge between the anchor and the NPPF. The three different NPPFs were pooled at known ratios, and hybridized to synthetic RNAs containing the target sequences of interest, as well to CFSs complementary to the flanking regions on the NPPFs. Following S1-mediated digestion of unhybridized RNA, NPPFs, and CFSs, the reaction was split. One fraction was incubated with the array under conditions to permit the NPPFs to bind to their appropriate bifunctional linker. Binding of the NPPF to the array was detected by the biotin label present on the NPPF using fluorescent streptavadin-phycoerythrin.

In another experiment, another fraction of the pooled reaction was PCR amplified prior to hybridization to an array, and the product was diluted 1:10 or 1:100 before hybridization to the array. For PCR amplification the reaction containing NPPFs were incubated with PCR primers. One primer included a sequence that was identical to the 5'-flanking sequence (and included a biotin label) and the second primer included a sequence that was complementary to the 3'-flanking sequence. The first primer complementary to the 5'-flanking sequence was 22 nucleotides and had a Tm of 59° C., and the second primer complementary to the 3'-flanking sequence was 22 nucleotides and had a Tm of 56° C. The advantage of using the NPPFs which have the same flanking sequences (but different target-specific regions) is that the flanking sequences permit the use of universal PCR primers, such that only a single 5'-primer sequence and a single 3'-primer sequence are needed to amplify a plural of different NPPF sequences. The NPPF amplicons were diluted 1:10 or 1:100 then hybridized to the array and detected as described above.

As shown in FIG. 7, the use of PCR amplification, prior to hybridization capture, increases the sensitivity by at least 150-fold (taking into account the dilution of the amplicons following the PCR step).

EXAMPLE 3

Simultaneous Sequencing of a Plurality of NPPFs Designed to Measure mRNAs or miRNAs This example describes methods used to generate and sequence NPPFs.

Two sets of NPPFs were generated. In the first set, forty-six different NPPFs were generated. Each NPPF included a region that was specific for a particular target nucleic acid molecule 25 nucleotides in length with a median Tm of 56° C., as well as flanking sequences on both ends. For the second set, thirteen different NPPFs were generated. Each NPPF included a region that was specific for a particular miRNA target nucleic acid molecule 18-25 nucleotides in length with a median Tm of 51° C., as well as flanking sequences on both ends.

For all NPPFs, regardless of target, although the 5'- and 3'-flanking sequences differed, they were the same for each of the different NPPFs. The 5'-flanking sequence (5'-AGTTCA-GACGTGTGCTCTTCCGATC 3'; SEQ ID NO: 17) was 25 nucleotides with a Tm of 61° C. and the 3'-flanking sequence (5' GATCGTCGGACTGTAGAACTCTGAA 3'; SEQ ID NO: 18) was 25 nucleotides with a Tm of 63° C.

qNPA was performed on lysates from two cell lines at different concentrations, using these NPPFs as probes. FIG. 10 shows the qNPA reactions, the samples used as input material, and the experiment tags added prior to sequencing. Reactions were performed in triplicate for each cell concentration. Some experiment tags were not recognized by the sequencer software and thus the reactions tagged with those experiment tags were not considered in this analysis. The different NPPFs were pooled, and hybridized to the RNA of a cell lysate, as well as to CFSs complementary to the flanking regions on the NPPFs. Hybridization was performed at 50° C. for the forty-six NPPFs from set 1, but performed at 37° C. for the thirteen NPPFs from set 2. The difference in temperature takes into account the shorter length of the miRNA NPPFs and their corresponding lower Tms.

Following S1-mediated digestion of unhybridized RNA, NPPFs, and CFSs, the reaction was neutralized by addition of 1M Tris pH 9.0 and the S1 nuclease was inactivated by heating to 95° C. for 20 minutes. Each resulting reaction, which contained NPPFs as representatives of the original transcripts in the sample, was then incubated with PCR primers. One primer included a sequence that was complementary to the 5'-flanking sequence and the second primer included a sequence that was complementary to the 3'-flanking sequence. The second primer also included a sequence to allow for incorporation of a six nucleotide experiment tag into the resulting amplicon, so that each NPPF amplified using this primer had the same six nucleotide experiment tag.

The first primer (5'-AATGATACGGCGACCACCGA-CAGGTTCAGAGTTCTACAGTCCGACGATC 3'; SEQ ID NO: 19) was 49 bases in length. Twenty of these bases were identical to the 5'-flanking sequence. These 20 bases had a Tm of 54° C. and the overall Tm of the entire primer was 70° C. The second primer, (5'-CAAGCAGAAGACGGCATAC-GAGATnnnnnnGTGACTGGAGTTCAGACGTG TGCTCTT 3'; SEQ ID NO: 20) complementary to the 3'-flanking sequence was 57 nucleotides total with a Tm of about 70° C. The first 19 nucleotides of the second primer were exactly complementary to the 3'-flanking region and had a Tm of 54° C. The six bases marked with "nnnnnn" above were one of the following 24 sequences in Table 2. The resulting sequence is shown in the right column, with its SEQ ID NO: in parenthesis.

TABLE 2

Sequence of Primers and Barcodes

| Barcode sequence (nnnnnn in SEQ ID NO: 20) | Resulting Primer Sequence with Barcode (SEQ ID NO:) |
|---|---|
| ATCACG | CAAGCAGAAGACGGCATACGAGATTCACGGTGACTGGAGTTCAGACGTGTGCTCTT (21) |
| CGATGT | CAAGCAGAAGACGGCATACGAGATCGATGTGTGACTGGAGTTCAGACGTGTGCTCTT (22) |
| TTAGGC | CAAGCAGAAGACGGCATACGAGATTTAGGCGTGACTGGAGTTCAGACGTGTGCTCTT (23) |
| TGACCA | CAAGCAGAAGACGGCATACGAGATTGACCAGTGACTGGAGTTCAGACGTGTGCTCTT (24) |
| ACAGTG | CAAGCAGAAGACGGCATACGAGATACAGTGGTGACTGGAGTTCAGACGTGTGCTCTT (25) |
| GCCAAT | CAAGCAGAAGACGGCATACGAGATGCCAATGTGACTGGAGTTCAGACGTGTGCTCTT (26) |
| CAGATC | CAAGCAGAAGACGGCATACGAGATCAGATCGTGACTGGAGTTCAGACGTGTGCTCTT (27) |
| ACTTGA | CAAGCAGAAGACGGCATACGAGATACTTGAGTGACTGGAGTTCAGACGTGTGCTCTT (28) |
| GATCAG | CAAGCAGAAGACGGCATACGAGATGATCAGGTGACTGGAGTTCAGACGTGTGCTCTT (29) |
| TAGCTT | CAAGCAGAAGACGGCATACGAGATTAGCTTGTGACTGGAGTTCAGACGTGTGCTCTT (30) |
| GGCTAC | CAAGCAGAAGACGGCATACGAGATGGCTACGTGACTGGAGTTCAGACGTGTGCTCTT (31) |
| CTTGTA | CAAGCAGAAGACGGCATACGAGATCTTGTAGTGACTGGAGTTCAGACGTGTGCTCTT (32) |
| AGTCAA | CAAGCAGAAGACGGCATACGAGATAGTCAAGTGACTGGAGTTCAGACGTGTGCTCTT (33) |
| AGTTCC | CAAGCAGAAGACGGCATACGAGATAGTTCCGTGACTGGAGTTCAGACGTGTGCTCTT (34) |
| ATGTCA | CAAGCAGAAGACGGCATACGAGATATGTCAGTGACTGGAGTTCAGACGTGTGCTCTT (35) |
| CCGTCC | CAAGCAGAAGACGGCATACGAGATCCGTCCGTGACTGGAGTTCAGACGTGTGCTCTT (36) |

TABLE 2-continued

Sequence of Primers and Barcodes

| Barcode sequence (nnnnnn in SEQ ID NO: 20) | Resulting Primer Sequence with Barcode (SEQ ID NO:) |
|---|---|
| GTAGAG | CAAGCAGAAGACGGCATACGAGATGTAGAGGTGACTGGAGTTCAGACGTGTGCTCTT (37) |
| GTCCGC | CAAGCAGAAGACGGCATACGAGATGTCCGCGTGACTGGAGTTCAGACGTGTGCTCTT (38) |
| GTGAAA | CAAGCAGAAGACGGCATACGAGATGTGAAAGTGACTGGAGTTCAGACGTGTGCTCTT (39) |
| GTGGCC | CAAGCAGAAGACGGCATACGAGATGTGGCCGTGACTGGAGTTCAGACGTGTGCTCTT (40) |
| GTTTCG | CAAGCAGAAGACGGCATACGAGATGTTTCGGTGACTGGAGTTCAGACGTGTGCTCTT (41) |
| CGTACG | CAAGCAGAAGACGGCATACGAGATCGTACGGTGACTGGAGTTCAGACGTGTGCTCTT (42) |
| GAGTGG | CAAGCAGAAGACGGCATACGAGATGAGTGGGTGACTGGAGTTCAGACGTGTGCTCTT (43) |
| GGTAGC | CAAGCAGAAGACGGCATACGAGATGGTAGCGTGACTGGAGTTCAGACGTGTGCTCTT (44) |

Each triplicate reaction was amplified in a separate PCR reaction, and had a separate experimental tag, so that variance could be identified (see FIG. 10). The resulting amplicons were cleaned up using either gel purification or standard column-based purification (Qiagen QIAQuick spin columns). The amplicons containing the NPPF and an experimental tag were then sequenced using an Illumina platform. While the experimental tag can be located in several places, in this example, it was located at the 3'-end of the amplicon, immediately downstream of a region complimentary to an index-read sequencing primer. Illumina sequencing was thus done in two steps, an initial read of the sequence followed by a second read of the experimental tag using a second sequencing primer. Using two sequencing primers in this manner is one standard method for multiplexing samples on the Illumina platform.

Each amplicon sequenced was sorted based first on the experiment tag (barcode), and then within each experiment tag group, the number of amplicons identified for each of the different tags was counted. The amplicons were compared to the expected sequences using Bowtie.

Figure 11:
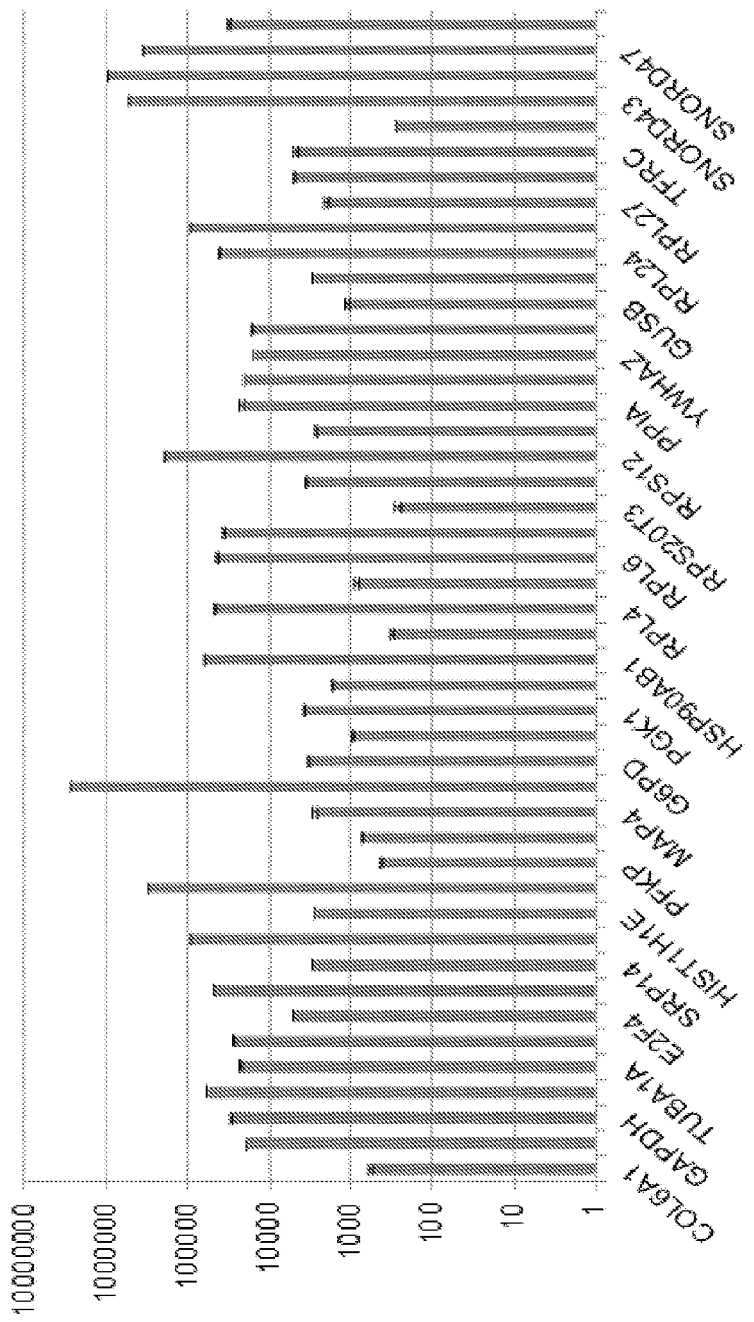
FIG. 11 is a bar graph showing the sequencing counts of forty-six NPPFs from a triplicate sequencing experiment using THP1 cell lysates. The error bars represent 1 standard deviation from the mean.

FIG. 11 shows the results from triplicate qNPA reactions on THP1 cells, using the 46 mRNA NPPFs. Excellent reproducibility was observed between replicates and CVs are low. The graph represents the number of amplicons detected for each of the forty-six unique NPPFs corresponding to the original ratio of NPPF pooled prior to PCR. Error bars represent 1 standard deviation from the mean. The probes were measured in three separate experiments, each of which had a different experimental tag added during amplification. These were all pooled into a single channel of the sequencer and sequenced. The error bars indicate the reproducibility (1 SD) of the three experiments.

Figure 12A:
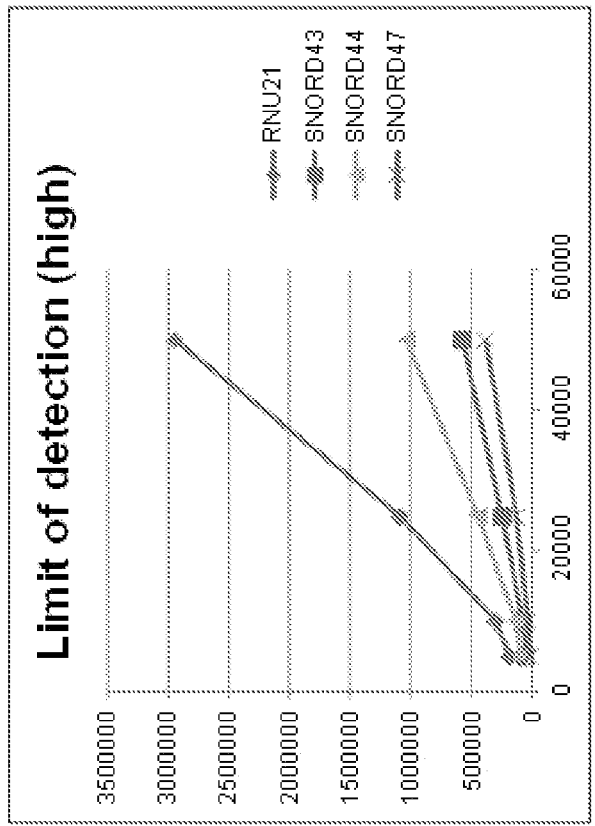
FIGS. 12A and 12B are line plots of sequencing counts of NPPFs from titration sequencing. This experiment looked at output linearity over an input range, as well as the range and limits of detection of the qNPS counting method. Four concentrations of THP1 cell lysate were used as input material. (A) shows the eight NPPFs with the lowest counts, (B) shows the four NPPFs with the highest counts. This experiment was performed in triplicate; this plot shows the result from only one replicate.
Figure 12B:
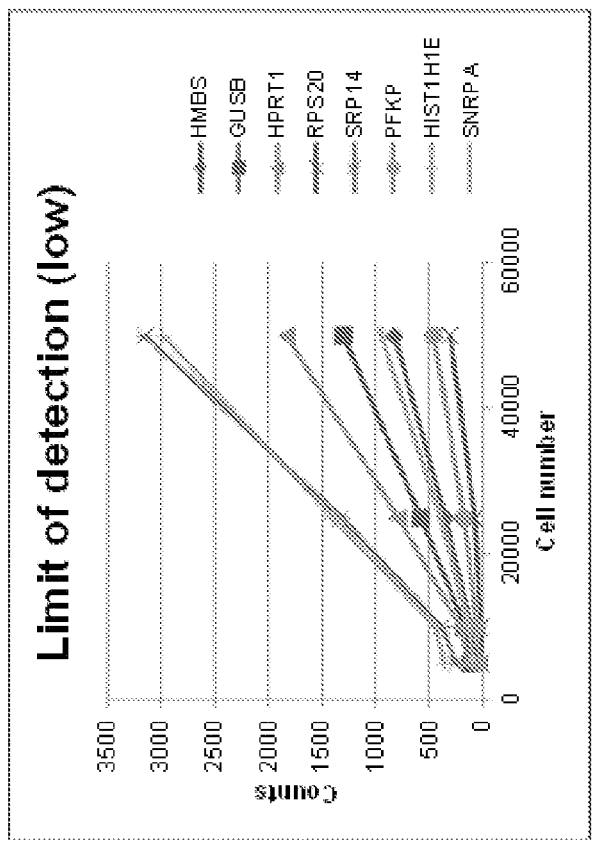

FIGS. 12A and 12B show the plot counts obtained for 12 of the 46 mRNA NPPFs from reactions run on a four-point THP1 cell titration. The data shown represent the lowest (A) and highest (B) abundance NPPFs, and demonstrate the large range of detection obtainable using sequencing. It also demonstrates the linearity of the qNPS reaction for both high and low abundance probes (representing high and low expression of the corresponding RNA in the sample).

Figure 13:
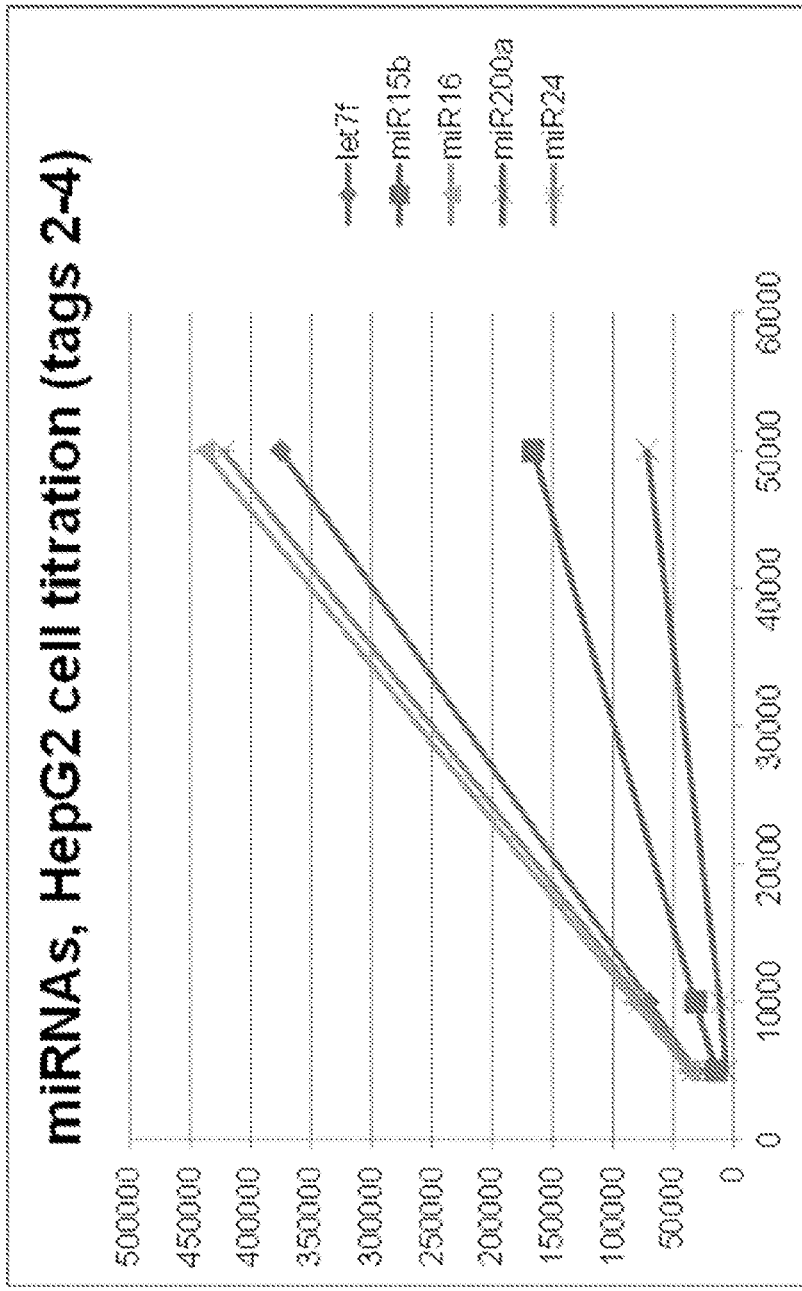
FIG. 13 is a line plot of sequencing counts of NPPFs to measure miRNAs. Three concentrations of HepG2 cell lysate were used as input material. Counts for five representative NPPFs are shown. This experiment was performed in triplicate; this plot shows the result from only one replicate.

FIG. 13 plots the results for five of the thirteen miRNA NPPFs from reactions run on a three-point HepG2 cell titration (5000 cells-50000 cells). These five were chosen because they had similar levels and could be clearly seen on the same plot. The plot demonstrates that miRNAs are detectable in cell lysates using the disclosed methods, and show good linearity over the sample sizes tested.

EXAMPLE 4

Detection of a Plurality of NPPFs Designed to Measure mRNA Using Sequencing and Capture of the NPPFs on an Array This example describes methods used to generate and sequence NPPFs.

Nine different NPPFs were generated. Each NPPF included a region that was specific for a particular target nucleic acid molecule 25 nucleotides in length with a median Tm of 57° C., as well as flanking sequences on both ends. Although the 5'- and 3'-flanking sequences differed, they were the same for each of the different NPPFs. The 5'-flanking sequence (5'-AGTTCAGACGTGTGCTCTTCCGATC-3'; SEQ ID NO: 17) was 25 nucleotides with a Tm of 61° C. and the 3'-flanking sequence (5' GATCGTCGGACTGTA-GAACTCTGAA-3'; SEQ ID NO: 18) was 25 nucleotides with a Tm of 63° C. A biotin label was included on the 5' flanking sequence of each NPPF.

qNPA was performed on samples comprised of dilutions of synthetic RNAs (in vitro transcribed RNAs) in qNPA lysis buffer. Reactions were performed in triplicate for each sample concentration. The different NPPFs were pooled at 166 pM each, and hybridized to the samples described above, as well as to CFSs complementary to the flanking regions on the NPPFs. CFSs were included in the reaction at a 10-fold molar ratio (1.6 nM each CFS). Hybridization was performed at 50° C. for at least 16 hours in a total reaction volume of 30 µl. Following hybridization, 20 µl of S1 reaction buffer was added to the reaction. This buffer is comprised of: 100 mM NaOAc pH 5.0, 250 mM KCl, 22.5 nM ZnSO4, and 25 U of S1 nuclease. The S1 reaction was allowed to proceed for 90 minutes at 50° C. Following S1-mediated digestion of unhybridized RNA, NPPFs, and CFSs, the reaction was neutralized by addition of 1.5µl of 1M Tris pH 9.0 and the S1 nuclease was inactivated by heating to 95° C. for 20 minutes. Each resulting reaction contained NPPFs as representatives of the original transcripts in the sample. At this point, the reaction was split into two parts.

One part of the unamplified NPPFs was hybridized to an array following qNPA. The array included an anchor probe bound to bifunctional linkers. One half of the bifunctional linker is complementary to the anchor, and the other half is complementary to the gene-specific part of the NPPF. The linker thus forms a bridge between the anchor and the NPPF. The NPPFs from the above reaction were supplemented with a salt replacement buffer to adjust the reaction to conditions used for array hybridization (salt replacement buffer is: 3.225 M NaCl; 67.5 mM EDTA pH 8.0; 3×SSC; 500 mM HEPES pH 7.5) and were incubated with the array for 16 hours at 50° C. Binding of the NPPF to the array was detected by the biotin label present on the NPPF using fluorescent streptavadin-phycoerythrin.

The other part of the reaction was prepared for sequencing. The reaction was first incubated with PCR primers. One primer included a sequence that was complementary to the 5'-flanking sequence and the second primer included a sequence that was complementary to the 3'-flanking sequence. The second primer also included a sequence to allow for incorporation of a six nucleotide experiment tag into the resulting amplicon, so that each NPPF amplified using this primer had the same six nucleotide experiment tag.

The first primer was 49 bases in length. Twenty of these bases were identical to the 5'-flanking sequence. These 20 bases had a Tm of 54° C. and the overall Tm of the entire primer was 70° C. The second primer, complementary to the 3'-flanking sequence was 57 nucleotides total with a Tm of about 70° C. The first 19 nucleotides of the second primer were exactly complementary to the 3'-flanking region and had a Tm of 54° C.

Each triplicate reaction was amplified in a separate PCR reaction, with a separate tag, so that variance could be identified. The resulting amplicons were cleaned up using either gel purification or standard column-based purification (Qiagen QIAQuick spin columns). The amplicons containing the NPPF and an experimental tag were then sequenced using an Illumina platform, using the second index read technique to sequence the experiment tag, as described in Example 3.

The PCR reactions were also set up to determine the impact of cycle number on the sequencing results. Briefly, each triplicate reaction was amplified in three separate PCR reactions, each reaction, with a separate tag, so that variance could be identified. These three PCR reactions underwent 10, 12, or 15 cycles of PCR the resulting amplicons were cleaned up using either gel purification or standard column-based purification (Qiagen QIAQuick spin columns). The amplicons containing the NPPF and an experimental tag were then sequenced using an Illumina platform, using the second index read technique to sequence the experiment tag, as described in Example 3.

Each amplicon sequenced was sorted based first on the experiment tag (barcode), and then within each experiment tag group, the number of amplicons identified for each of the different tags was counted. The amplicons were compared to the expected sequences using Bowtie.

FIG. 14 shows that low PCR cycle numbers (10, 12, and 15) do not unduly influence sequencing results. The bar graph shows the counts generated for each NPPF following sequencing. The number of cycles and the amount of input material in the original sample are indicated. The data were normalized to allow for comparison of the different cycles and input levels. While it is clear that any of these cycles could be used with the disclosed methods, the increase in material in the samples following 15 PCR cycles made subsequent clean up of the sequencing library easier. Greater than 15 cycles produces spurious products larger and smaller than the desired size of amplicon. Thus, in some examples, the disclosed method use 10 to 15 PCR cycles, such as 10, 11, 12, 13, 14, or 15 cycles.

Figure 15A:
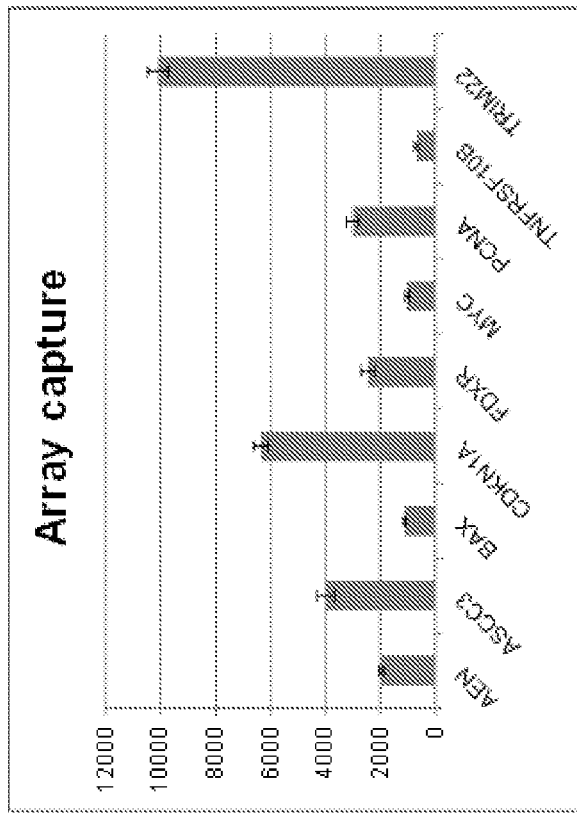
FIGS. 15A and 15B are bar graphs representing the NPPFs in a triplicate reactions that was split and either (A) hybridized to an array or (B) sequenced and counted. Triplicate reactions were averaged and error bars represent one standard deviation from the mean.
Figure 15B:
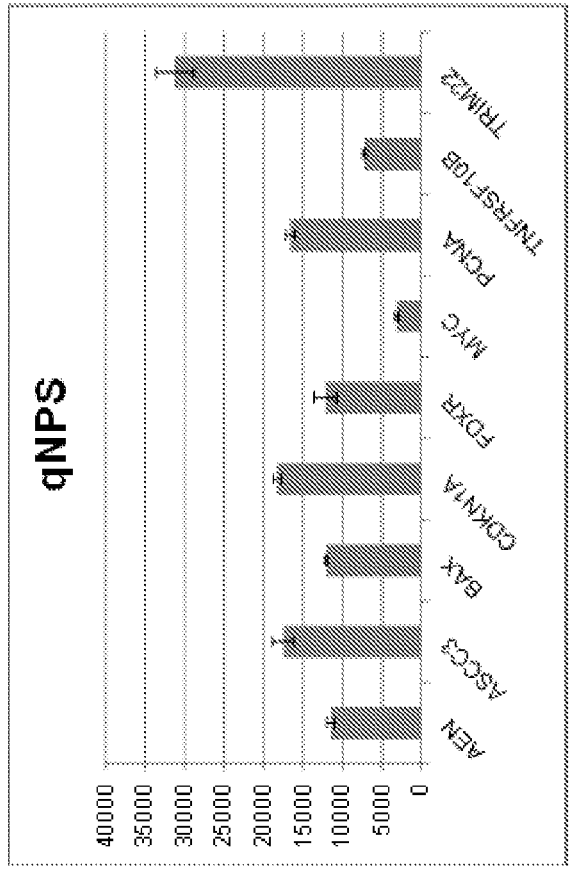

FIGS. 15A and 15B show the results from the same triplicate qNPA reactions after splitting. NPPFs were detected by hybridization to an array (FIG. 15A) or by counting sequenced NPPFs (FIG. 15B). The bars shown are averages of the triplicates, and error bars represent one standard deviation from the mean.

In view of the many possible embodiments to which the principles of the disclosed invention may be applied, it should be recognized that the illustrated embodiments are only examples of the disclosure and should not be taken as limiting the scope of the disclosure. Rather, the scope of the invention is defined by the following claims. We therefore claim as our invention all that comes within the scope and spirit of these claims.

We claimed:

1. A method of determining a sequence of at least one target nucleic acid molecule in a sample, comprising:
   contacting the sample with at least one nuclease protection probe comprising a flanking sequence (NPPF) under conditions sufficient for the NPPF to specifically bind to the target nucleic acid molecule,
   wherein the NPPF comprises:
      a 5'-end and a 3'-end,
      a sequence complementary to a region of the target nucleic acid molecule, permitting specific binding between the NPPF and the target nucleic acid molecule,
      a flanking sequence located 5', 3', or both, to the sequence complementary to the target nucleic acid molecule, wherein the flanking sequence comprises at least 12 contiguous nucleotides not found in a nucleic acid molecule present in the sample, providing a universal amplification sequence, and wherein the flanking sequence is complementary to at least a portion of an amplification primer;
   contacting the sample with a nucleic acid molecule comprising a sequence complementary to the flanking sequence (CFS) under conditions sufficient for the flanking sequence to specifically bind to the CFS;
   contacting the sample with a nuclease specific for single-stranded nucleic acid molecules under conditions sufficient to remove unbound nucleic acid molecules, thereby generating a digested sample comprising NPPFs hybridized to the target nucleic acid molecule and to the CFS(s);
   amplifying NPPFs in the digested sample with the amplification primer, thereby generating NPPF amplicons; and
   sequencing at least a portion of the NPPF amplicons, thereby determining the sequence of the at least one target nucleic acid molecule in the sample.

2. The method of claim 1, wherein the NPPF comprises a DNA molecule.

3. The method of claim 1, wherein:
   the NPPF comprises 35-150 nucleotides:,
   the sequence complementary to a region of the target nucleic acid molecule is 10-60 nucleotides in length;
   the flanking sequence is 12 to 50 nucleotides in length;
   or combinations thereof.

4. The method of claim 1, wherein the NPPF comprises a flanking sequence at the 5'-end and the 3'-end, wherein the flanking sequence at the 5'-end differs from the flanking sequence at the 3'-end.

5. The method of claim 1, wherein the at least one amplification primer further comprises a sequence that permits attachment of an experimental tag or sequencing adapter to the NPPF amplicon during the amplification step.

6. The method of claim 1, wherein the flanking sequence further comprises an experimental tag, sequencing adapter, or both.

7. The method of claim 5, wherein:
   the experimental tag comprises a nucleic acid sequence that permits identification of a sample, subject, treatment or target nucleic acid sequence;
   the sequencing adapter comprises a nucleic acid sequence that permits capture onto a sequencing platform;
   the experimental tag or sequence tag is present on the 5'-end or 3'-end of the NPPF amplicon;
   or combinations thereof.

8. The method of claim 1, wherein one or more target nucleic acid molecules are fixed, cross-linked, or insoluble.

9. The method of claim 1, wherein the NPPF is a DNA and the nuclease comprises an exonuclease, an endonuclease, or a combination thereof.

10. The method of claim 1, wherein the nuclease specific for single-stranded nucleic acid molecules comprises S1 nuclease.

11. The method of claim 1, wherein the method sequences at least one target nucleic acid molecule in a plurality of samples simultaneously.

12. The method of claim 1, wherein the method sequences at least two target nucleic acid molecules, and wherein the sample is contacted with at least two different NPPFs, each NPPF specific for a different target nucleic acid molecule.

13. The method of claim 1, wherein the method is performed on a plurality of samples and at least two target nucleic acid molecules are detected in each of the plurality of samples.

14. The method of claim 1, wherein at least one NPPF is specific for a miRNA target nucleic acid molecule and at least one NPPF is specific for an mRNA target nucleic acid molecule.

15. The method of claim 1, further comprising lysing the sample.

16. The method of claim 1, further comprising:
   comparing an NPPF sequence obtained to a reference sequence database; and
   determining a number of each identified NPPF sequences.

17. The method of claim 1, wherein the NPPF amplicons are labeled with biotin.

18. The method of claim 17, wherein detecting the NPPF amplicons comprises contacting the NPPF amplicons with avidin or streptavidin conjugated to horseradish peroxidase or alkaline phosphatase.

19. The method of claim 1, wherein the at least one NPPF comprises at least 10 NPPFs.

20. The method of claim 1, wherein the sample is formalin fixed.

* * * * *

UNITED STATES PATENT AND TRADEMARK OFFICE
CERTIFICATE OF CORRECTION

PATENT NO.       : 8,741,564 B2
APPLICATION NO.  : 14/115032
DATED            : June 3, 2014
INVENTOR(S)      : Seligmann et al.

Page 1 of 1

It is certified that error appears in the above-identified patent and that said Letters Patent is hereby corrected as shown below:

In the Claims

Column 81, line 52, claim 3, "nucleotides:," should be --nucleotides;--.

Signed and Sealed this
First Day of December, 2015

Michelle K. Lee
*Director of the United States Patent and Trademark Office*